US007998460B2

(12) United States Patent
Monje et al.

(10) Patent No.: US 7,998,460 B2
(45) Date of Patent: Aug. 16, 2011

(54) PREVENTION OF DEFICITS IN NEUROGENESIS WITH ANTI-INFLAMMATORY AGENTS

(75) Inventors: Michelle L. Monje, Boston, MA (US); Theo D. Palmer, Stanford, CA (US)

(73) Assignee: The Board of Trustees of the Leland Stanford Junior University, Palo Alto, CA (US)

(*) Notice: Subject to any disclaimer, the term of this patent is extended or adjusted under 35 U.S.C. 154(b) by 741 days.

(21) Appl. No.: 11/473,196

(22) Filed: Jun. 21, 2006

(65) Prior Publication Data
US 2007/0135393 A1    Jun. 14, 2007

Related U.S. Application Data

(63) Continuation-in-part of application No. 10/826,472, filed on Apr. 16, 2004.

(60) Provisional application No. 60/519,562, filed on Nov. 12, 2003, provisional application No. 60/463,769, filed on Apr. 17, 2003.

(51) Int. Cl.
*A61K 49/00* (2006.01)
*A61K 38/00* (2006.01)
*A61K 35/30* (2006.01)

(52) U.S. Cl. .................... 424/9.2; 514/2.1; 424/570

(58) Field of Classification Search .................. None
See application file for complete search history.

(56) References Cited

U.S. PATENT DOCUMENTS
2003/0203844 A1* 10/2003 Delfani et al. .................. 514/12

OTHER PUBLICATIONS

Tada et al. Neurosurgery 41: 209-219, 1997—online publication 1-18 pages.*
Ferencik et al. Bratisl Lek Listy 102(3): 123-32, 2001.*
Efsen et al. Hepatology 33: 713-721, 2001.*
Hull et al. Curr Med Chem 9: 83-89, 2002.*
Richardson et al. (Soc for Neurosc Meeting, Abstract 304.12, 2002).*
Yang et al. NeuroRep 9: 3477-3480, 1998.*
Monje et al. Nat Med 8: 955-962, 2002.*
Kondo et al. Brain Res 791: 352-356, 1998.*
Plevova, Radiol Oncol 36: 33-40, 2002.*
Kyrkanides et al. Mol Brain Res. 104: 159-169, 2002.*
Liu et al. J Neurosc 18: 7768-7778, 1998.*
Price et al. (J Med Primatol 30: 81-87, 2001).*
Emmerling et al (Inflamm res: 47: 145-147, 1998).*
de Jong et al. (Ned Tijdschr Geneeskd 146: abstract, 2002).*
Aboody, K., et al., "Neural stem cells display extensive tropism for pathology in adult brain: evidence from intracranial gliomas," (2000) *PNAS*, 97(23):12846-12851.
Gage, "Mammalian neural stem cells," (2000) *Science*, 287:1433-1438.
Hoehm, B.D., et al., "Neurogenesis in rats after focal cerebral ischemia is enhanced by indomethacin," (2005) *Stroke*, 36:2718-2724.
Monje, M.L., et al., "Inflammatory blockade restores adult hippocampal neurogenesis," (2003) *Science*, 302:1760-1765.
Monje, M.L., et al., "Irradiation induces neural precursor-cell dysfunction," (2002) *Nature Medicine*, 8(9):955-962.
Rogers, J., et al., "Clinical trial of indomethacin in Alzheimer's disease," (1993) *Neurology*, 43:1609-1611.
Sasaki, T., et al., "Implication of cyclooxygenase-2 on enhanced proliferaton of neural progenitor cells in the adult mouse hippocampus after ischemia," (2003) *Journal of Neuroscience Research*, 72:461-471.
Yuzawa, et al., "APC0576: A novel small molecule, immunosuppressive agent effective in primate models," (2003) *Transplantation*, 75(9):1463-1468.
Hoehn et al., "Recovery of Neurogenesis following stroke after anti-inflammatory treatment," 33rd Annual Meeting of the Society of Neuroscience, Society for Neuroscience Abstract Viewer and Itinerary Planner, 2003, Abstract No. 844.12.
Sasaki et al., "Implication of Cyclooxygenase-2 on Enhanced Proliferation of Neural Progenitor Cells in the Adult Mouse Hippocampus After Ischemia," J Neurosci. Res., 2003, 72(4):461-471.

* cited by examiner

*Primary Examiner* — Daniel E Kolker
*Assistant Examiner* — Aditi Dutt
(74) *Attorney, Agent, or Firm* — Bozicevic, Field & Francis LLP; Pamela J. Sherwodd; Elizabeth A. Alcamo

(57) ABSTRACT

Methods are provided for protecting an individual from adverse long-term effects of neuroinflammation. Inflammatory blockade maintains neurogenesis capability after cranial irradiation by reducing the negative effects of activated microglia on neural precursor cells. These findings have broad implications for a variety of diseases of cognition, involving neuroinflammation and precursor cell dysfunction.

6 Claims, 18 Drawing Sheets
(16 of 18 Drawing Sheet(s) Filed in Color)

Figure 1
A
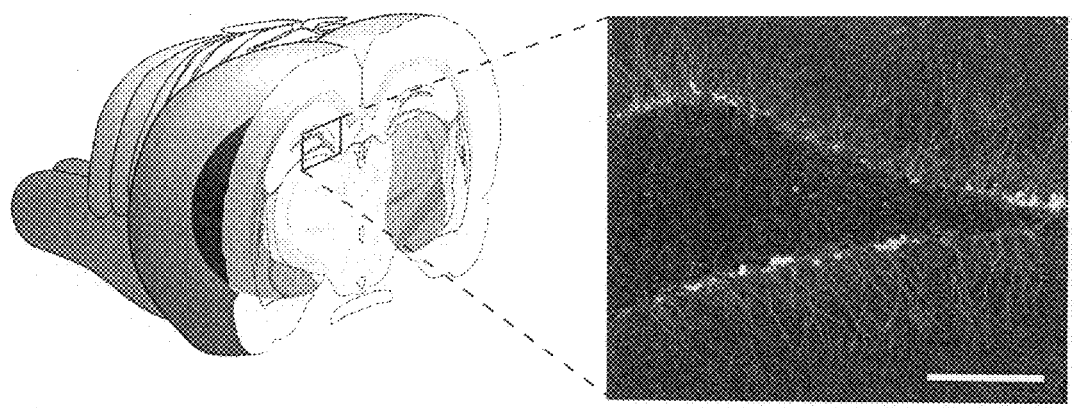
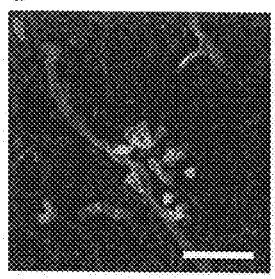 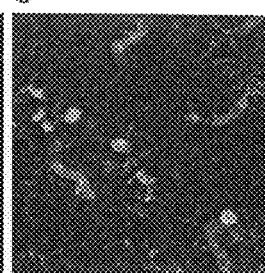 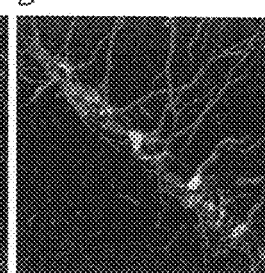 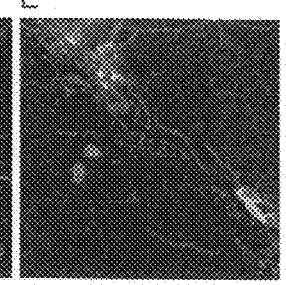
B    C    D    E
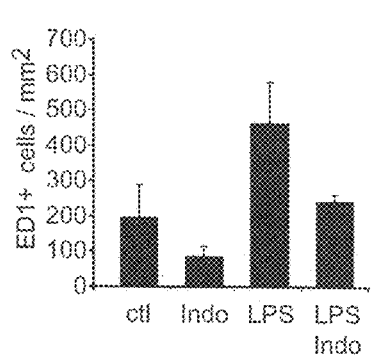 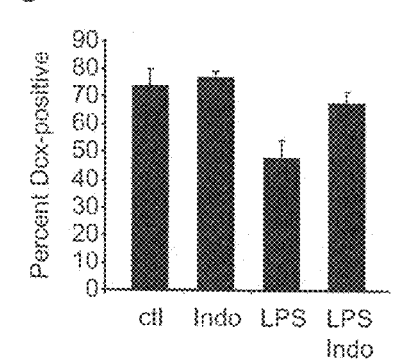 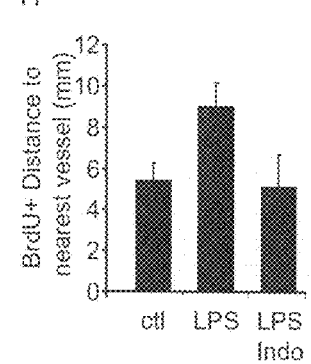
F    G    H Figure 4
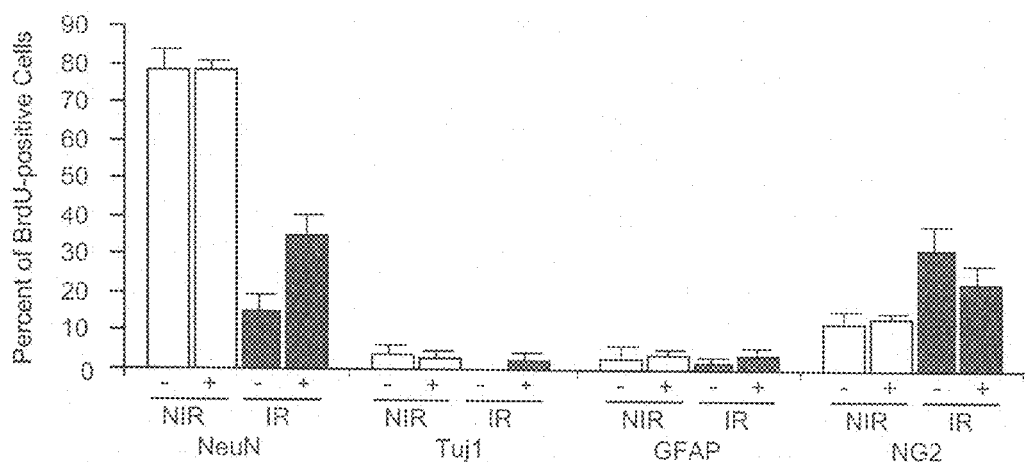
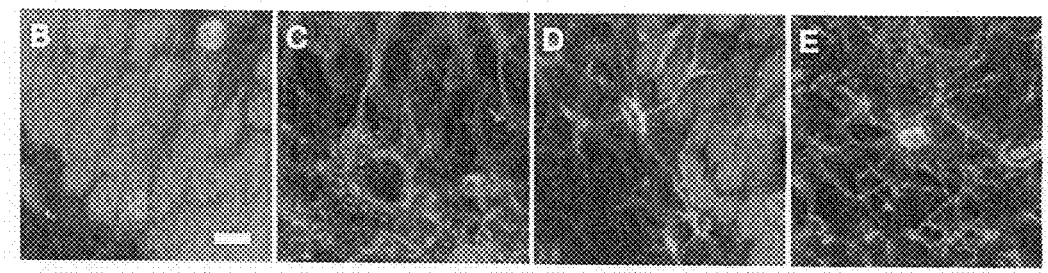
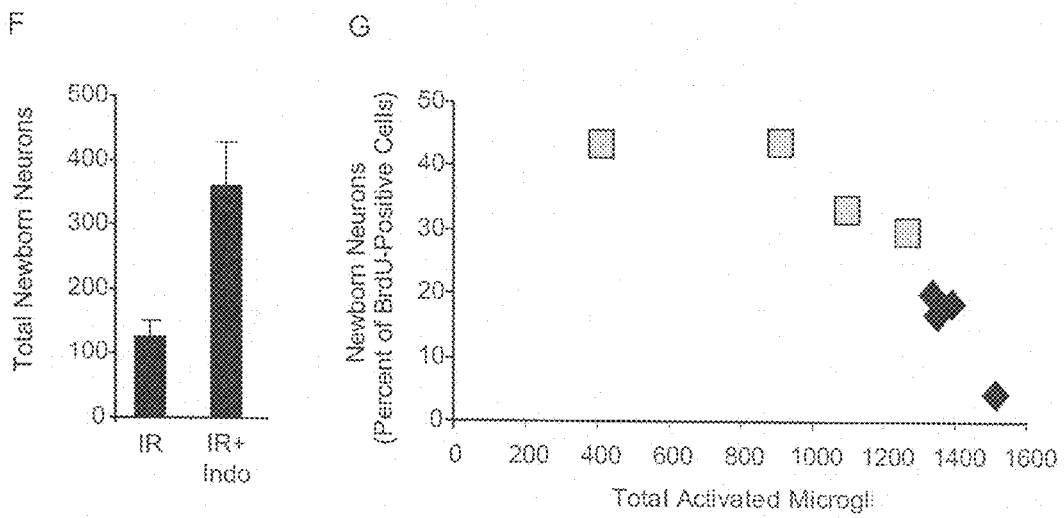

FIGURE 8  A
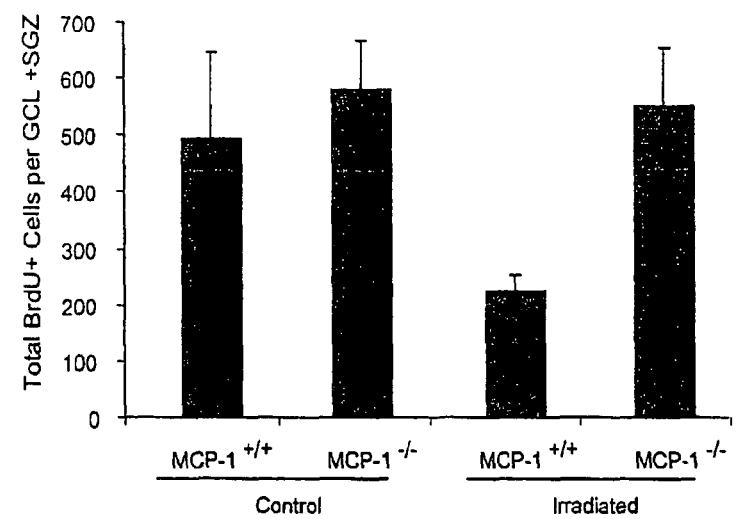
B
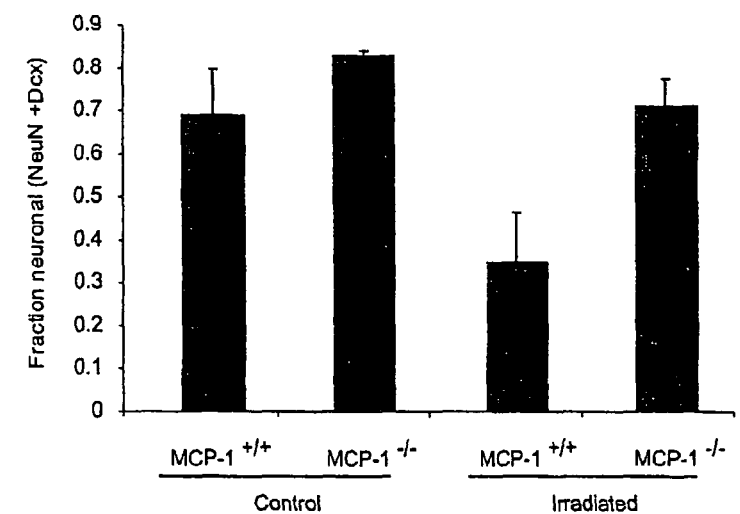
C
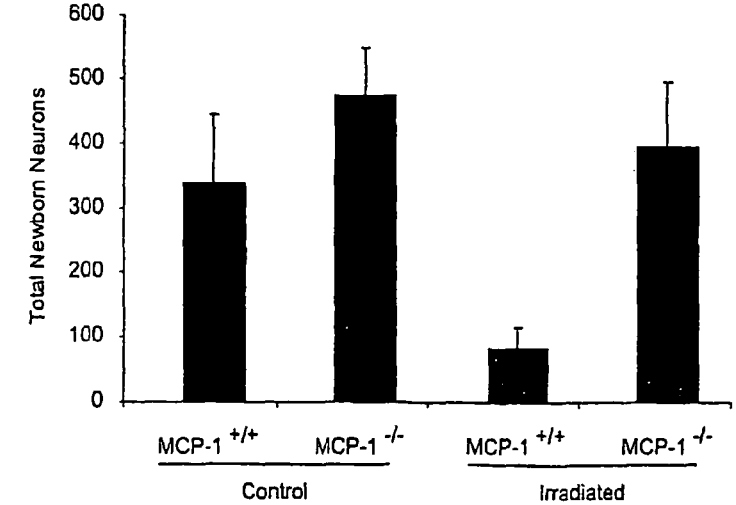

```
                            SEQUENCE LISTING

<160> NUMBER OF SEQ ID NOS: 10

<210> SEQ ID NO 1
<211> LENGTH: 22
<212> TYPE: DNA
<213> ORGANISM: Artificial Sequence
<220> FEATURE:
<223> OTHER INFORMATION: primer

<400> SEQUENCE: 1
aagagagagg ccctcagttg ct                                             22

<210> SEQ ID NO 2
<211> LENGTH: 22
<212> TYPE: DNA
<213> ORGANISM: Artificial Sequence
<220> FEATURE:
<223> OTHER INFORMATION: primer

<400> SEQUENCE: 2
ttgtgaggga gatgctcagt gt                                             22

<210> SEQ ID NO 3
<211> LENGTH: 20
<212> TYPE: DNA
<213> ORGANISM: Artificial Sequence
<220> FEATURE:
<223> OTHER INFORMATION: primer

<400> SEQUENCE: 3
gacaggccct actgggaatg                                                20

<210> SEQ ID NO 4
<211> LENGTH: 24
<212> TYPE: DNA
<213> ORGANISM: Artificial Sequence
<220> FEATURE:
<223> OTHER INFORMATION: primer

<400> SEQUENCE: 4
cgttgtcaag aaacactgaa gaca                                           24

<210> SEQ ID NO 5
<211> LENGTH: 18
<212> TYPE: DNA
<213> ORGANISM: Artificial Sequence
<220> FEATURE:
<223> OTHER INFORMATION: primer

<400> SEQUENCE: 5
cggcttcagc gagtgcat                                                  18

<210> SEQ ID NO 6
<211> LENGTH: 19
<212> TYPE: DNA
<213> ORGANISM: Artificial Sequence
<220> FEATURE:
<223> OTHER INFORMATION: primer

<400> SEQUENCE: 6
cggtgttaac gccctcaca                                                 19
```

```
<210> SEQ ID NO 7
<211> LENGTH: 18
<212> TYPE: DNA
<213> ORGANISM: Artificial Sequence
<220> FEATURE:
<223> OTHER INFORMATION: primer

<400> SEQUENCE: 7
ggaggcggtg cagttcct                                                 18

<210> SEQ ID NO 8
<211> LENGTH: 22
<212> TYPE: DNA
<213> ORGANISM: Artificial Sequence
<220> FEATURE:
<223> OTHER INFORMATION: primer

<400> SEQUENCE: 8
ggagtggtaa agcagcttca tc                                            22

<210> SEQ ID NO 9
<211> LENGTH: 22
<212> TYPE: DNA
<213> ORGANISM: Artificial Sequence
<220> FEATURE:
<223> OTHER INFORMATION: primer

<400> SEQUENCE: 9
ggacagacga gtgcctcagt tc                                            22

<210> SEQ ID NO 10
<211> LENGTH: 24
<212> TYPE: DNA
<213> ORGANISM: Artificial Sequence
<220> FEATURE:
<223> OTHER INFORMATION: primer

<400> SEQUENCE: 10
tcatggcttc aagctcatcc tcct                                          24
```

PREVENTION OF DEFICITS IN NEUROGENESIS WITH ANTI-INFLAMMATORY AGENTS

CROSS-REFERENCE TO RELATED APPLICATIONS

This application is a continuation-in-part of U.S. non-provisional application Ser. No. 10/826,472, filed on Apr. 16, 2004, which claims the benefit of U.S. provisional applications 60/519,562, filed Nov. 12, 2003, and 60/463,769, filed Apr. 17, 2003, each of which are herein incorporated by reference.

BACKGROUND

Hippocampal neurogenesis occurs throughout life and the balance of neuronal loss and birth is essential in generating the plasticity necessary for new memory formation. The generation of new neurons within the hippocampus is mediated by proliferating neural stem/progenitor cells that are exquisitely sensitive to local signaling. Stem cells represent the most immature cell necessary for neurogenesis. These cells gives rise to more restricted precursors or progenitor cells and ultimately these progenitors differentiate into new functional neurons. These cells produce neurons in response to signals received from surrounding cells as well as humoral signals from circulating hormones, cytokines, and growth factors. Gross alterations in local microenvironments may allow ectopic neurogenesis to occur, or even block essential neurogenesis, leading to deficits in neurogenesis-dependent functions, such as learning and memory. Within this relatively new field of study, a paradigm of neural stem/progenitor cell dysregulation is emerging. Stress and the accompanying changes in stress hormones orchestrated by the hypothalamic-pituitary-adrenal (HPA) axis suppress hippocampal neurogenesis and lead to deficits in learning and memory. Glucocorticoids have played a central role in modeling this process but other factors also change with alterations in the HPA axis. Notable among these is the apparent link between pro-inflammatory cytokines and glucocorticoids. Inflammation and subsequent elevations of interleukin-1β (IL-1β) lead to the robust elevation of glucocorticoids via the HPA axis. Inflammation is also accompanied by the central production of pro-inflammatory cytokines. Among these are interleukin-6 and tumor necrosis factor-α (TNFα) which are found to be inhibitory to neurogenesis.

It is well-known that radiation is damaging to cells. Initial deposition of energy in irradiated cells occurs in the form of ionized and excited atoms or molecules distributed at random throughout the cells. It is the ionizations that cause most of the chemical changes in the vicinity of the event, by producing a positively charged or "ionized" molecule. These molecules are highly unstable and rapidly undergo chemical change to produce free radicals, atoms, or molecules containing unpaired electrons. These free radicals are extremely reactive and can lead to permanent damage of the affected molecule. As an immediate consequence of radiation damage, cells can undergo apoptosis, dying in interphase within a few hours of irradiation. Radiation damage can be acute, or can be manifested long after the initial event.

Cranial radiation therapy, a crucial treatment for brain tumors and other cancers, causes a progressive and debilitating decline in learning and memory. Cranial irradiation ablates hippocampal neurogenesis by damaging the neurogenic microenvironment. Endogenous neurogenesis is inhibited after irradiation despite the presence of neural precursor cells that retain the ability to make neurons, and neurogenesis is likewise inhibited for non-irradiated precursor cells transplanted to the irradiated hippocampus.

The investigation and development of methods to prevent this impairment in neurogenesis is of great clinical interest.
Publications The appearance of activated microglia in the brain is a common indicator of the inflammatory process and neuroinflammation and accompanying microglial pathology, which are associated with many diseases of cognition in which memory loss features prominently, such as Alzheimer's Disease, Lewy Body Dementia, and AIDS Dementia Complex. Clinical treatment with indomethacin and other NSAIDs has been demonstrated to ameliorate the risk and progression of memory loss (Rogers et al. (1993) *Neurology* 43:1609-1611; (2001) *N. Engl. J. Med.* 345:1515-1521).

SUMMARY OF THE INVENTION

Methods are provided for preventing defects in neurogenesis following conditions that result in neuroinflammation in the brain. The differentiation of neuronal precursor cells is shown to be adversely affected by the presence of inflammation in the brain. Among the components of inflammation, activated microglial cells are particularly harmful, and directly impair neuronal precursor cell differentiation. Such microglial cells can be resident in the brain, or can be recruited from the pool of circulating leukocytes by altered trafficking signals related to the neuroinflammatory process. Additional alterations within the neuronal precursor or stem cell microenvironment also accompany the activation of microglial cells in the brain. Such inflammatory changes in the microvasculature and other cell populations, such as astrocytes and neighboring neurons, impair the stem cell or progenitor cell's ability to generate neurons.

Methods of prevention reduce one or more of the adverse aspects of neuroinflammation. In one embodiment of the invention, general anti-inflammatory agents, e.g. NSAIDs, are administered. In another embodiment of the invention, agents are administered that block the recruitment and/or entry of circulating monocytes into the brain, including agents that antagonize chemokines, such as MCP-1. In another embodiment of the invention, agents that specifically block harmful cytokines, including IL-6; IL-1β; and TNFα; are administered. Local or systemic block of IL-6 activity is of particular interest, including administration of IL-6 blocking agents or related gp130 signaling modulators. Combinations of such therapies are also of interest.

Conditions giving rise to inflammation and subsequent changes in the stem cell signaling environment include radiation, surgery, trauma, autoimmune disease, neurodegenerative disease and other neuroinflammatory conditions. Transplantation of neuronal stem cells or other cell types intended to influence stem cell or progenitor cells, e.g. for therapeutic purposes, can also give rise to inflammation, and benefits from the methods of the invention. Administration of anti-inflammatory agents, prevents such activation of microglial cells or blocks the effect of cytokines produced by microglial cells and other cellular components of the neuroinflammatory process, such as activated astrocytes. By preventing or diminishing a loss of neurogenesis capacity, patients retain cognitive function that would otherwise be lost. In one embodiment of the invention, an improved method of cranial radiation therapy is provided, where anti-inflammatory agents are administered in conjunction with radiotherapy.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 1A-1H Inflammation inhibits hippocampal neurogenesis. Lipopolysaccharide (LPS, 1 mg/Kg i.p.) was given to induce a systemic inflammatory response, followed by daily injections of BrdU for 6 days to label proliferating cells and sacrifice on the $7^{th}$ day. Some rats were given the anti-inflammatory drug indomethacin twice each day (2.5 mg/kg i.p.) starting concurrently with LPS and continuing for the 1 week paradigm. (A) Schematic depicting the anatomic location of the dentate gyrus of the hippocampus within the rodent brain. The neurogenic region of the hippocampus, the granule cell layer is highlighted in red. To the right, a confocal photomicrograph shows detail of the dentate gyrus stained for the immature neuronal marker doublecortin (Dcx, red) and BrdU (proliferative cells, green). Immature neurons line the subgranule zone at the junction between the granule cell layer and the hilus of the hippocampal dentate gyrus. Scale bar, 100 µm. (B, C) Confocal micrographs of vasculature (tomato lectin, blue), BrdU-labeled cells (green) and activated microglia (ED-1, red). Proliferative cells are clustered in large groups proximal to the vasculature in naïve animals (B) while clustering and proximity to the vasculature is decreased in concert with striking activation of microglia following LPS treatment (C). Scale bar, 30 µm. (D, E) BrdU-labeled newborn neurons (BrdU, green; Dcx, red) are abundant in naïve animals (D) but significantly reduced following systemic LPS exposure (E). (F) Density of activated microglia (ED1+) in the granule cell layer and subgranule zone. Data are expressed as ED-1 positive cells per $mm^2$ in a 40 micron section. Systemic LPS exposure significantly increases the density of activated microglia ($P<0.05$; n=3); treatment with indomethacin decreases this inflammatory response. (G) Neuroinflammation induced by systemic LPS inhibits neurogenesis ($P<0.05$; n=3), as determined by phenotype-specific immunohistochemistry and confocal analysis. Anti-inflammatory therapy with indomethacin restores neurogenesis following LPS exposure ($P<0.05$; n=3). Data are expressed as the percent of non-microglial proliferating cells (BrdU+/CD11b−) that co-express doublecortin (Dcx) at the end of a one-week BrdU labeling paradigm. (H) Inflammation causes dissociation of the normal relationship between proliferating cells and the microvascualture. The average distance from the middle of a BrdU+ nucleus to it nearest tomato lectin stained vessel was significantly increased in the context of inflammation ($P<0.05$; n=6); indomethacin restores the vascular association ($P<0.05$; n=3). Distance measurements were performed on 40 micron sections as measured in the x and y plane. Proliferating microglia (BrdU+/CD11b+) were excluded from the distance measurements.

FIGS. 4A-4G Anti-inflammatory therapy restores neurogenesis following irradiation. Effect of indomethacin on newborn cells within the SGZ and granule cell layer. Non-irradiated NIR, white bars; irradiated, IR, black bars. Indomethacin (+/−2.5 mg/Kg) was administered orally every 12 hours beginning the day before and for 2 months after irradiation. (A) Relative proportion of proliferative cells adopting a recognized cell fate (NeuN=mature neurons; Tuj1=immature neurons; GFAP=astrocytes; NG2+/CD11b–=immature oligodendrocytes). Data are expressed as means+/−S.E.M; n=4 animals per group. Anti-inflammatory therapy with indomethacin increased the relative proportion of the proliferative cells adopting a neuronal phenotype by 2.5 fold (Student's t test; P<0.01). (B-E) Representative confocal micrographs of BrdU-labeled mature neurons (B, NeuN, green; GFAP, blue; BrdU, red); immature neurons (C, type III βtubulin, blue; NG2, green; BrdU, red); astrocytes (D, GFAP, green; NeuN, blue); and oligodendrocytes (E, NG1, green, CD11b, blue; BrdU, red). Scale bars=10 µm. (F) Increase in total number of newborn neurons per GCL+SGZ in irradiated animals treated with indomethacin. Unbiased stereologic quantification of BrdU+ cells adjusted for fraction of BrdU+ cells adopting aneuronal phenotype (NeuN+ plus Tuj1+). IR=irradiated; IR+Indo=irradiated, indomethacin treated. Anti-inflammatory therapy substantially increases the absolute number of newborn neurons per hippocampus (Student's t test; P<0.01). (G) Inflammation negatively correlates with the accumulation of new neurons. The fraction of dividing cells adopting a neuronal phenotype is inversely proportional to total number of activated microglia per dentate gyrus. Each data point represents one irradiated animal. Control irradiated animals (black diamonds), indomethacin-treated irradiated animals (gray squares).

FIGS. 8A-8C Hippocampal neurogenesis following radiation in adult MCP-1 deficient mice. Animals were treated with a single dose of 10 Gy cranial x-irradiation and then allowed to recover for one month. BrdU was then administered once each day for 6 days (beginning week 5 after irradiation) and then animals allowed to survive for an additional three weeks. Hippocampal formations were then evaluated for surviving newborn neurons 8 weeks after irradiation (one month after the initial BrdU injection). A. Total BrdU labeled cells per dentate gyrus of the hippocampus. Irradiation severely inhibits accumulation of BrdU labeled cells in wild type animals but has no significant impact on MCP-1 null animals. B. Fraction of BrdU cells adopting a neuronal phenotype (NeuN or doublecortin, Dcx positive). As for proliferative activity, the production and survival of neurons is severely attenuated in irradiated wild type mice but is completely unaffected in MCP-1 null animals. C. The total number of new born neurons detectable in the hippocampus can be derived by multiplying the fraction of new born cells that are neurons by the total number of newborn cells. As previously observed in rats, wild type mice show a >75% decrease in net neurogenesis after a single dose of 10 Gy x-irradiation. Neurogenesis in MCP-1 null animals is unaffected by x-irradiation.

Figure 2:
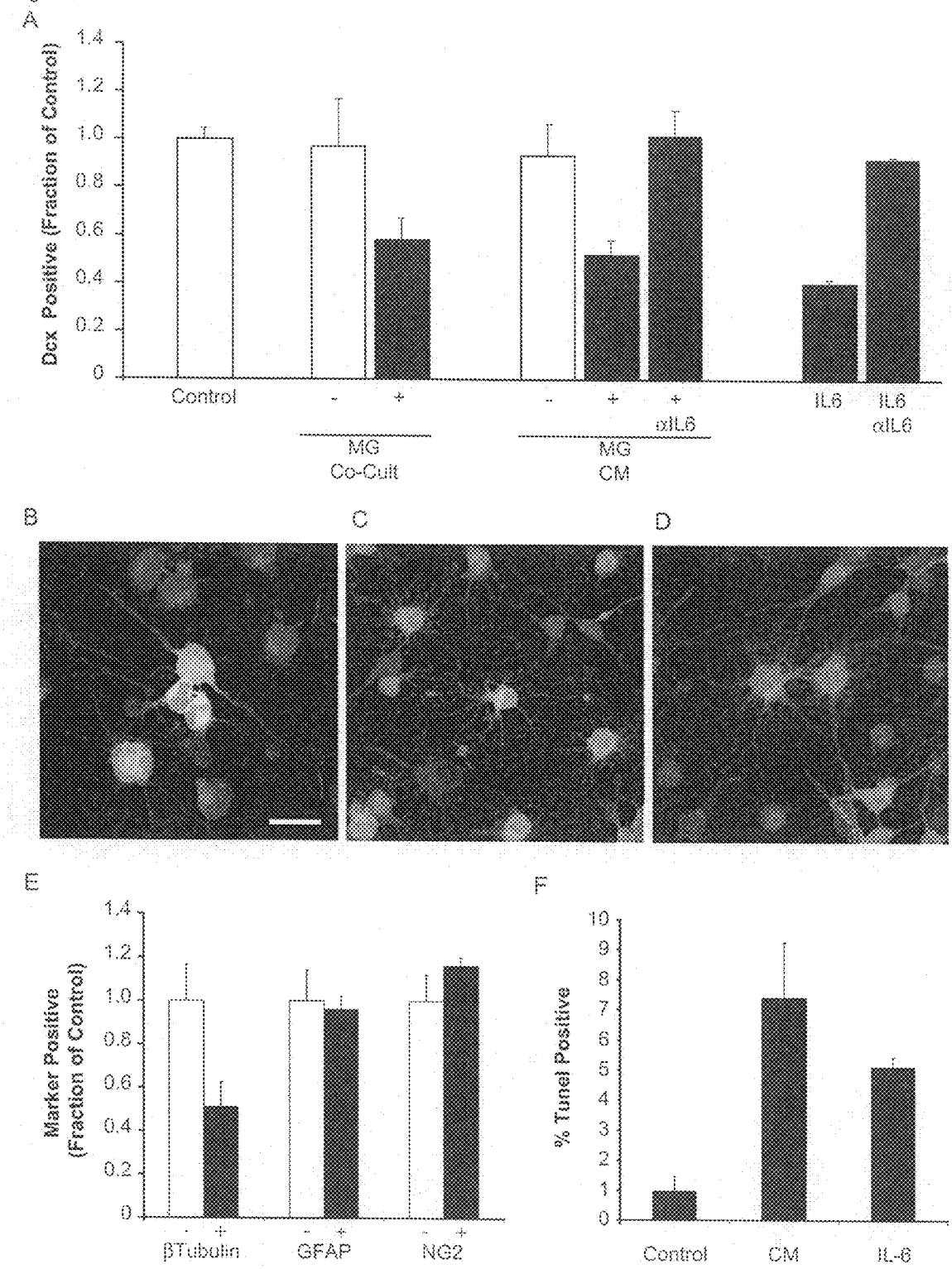
FIGS. 2A-2F Activated microglia inhibit neurogenesis via soluble factors that include IL-6. (A) Co-culture of with microglia (MG), from microglia or exposure to recombinant IL-6 decreases neuronal differentiation in vitro. GFP-positive neural progenitor cells (NPCs) were induced to differentiate for 60 hrs in the presence or absence of microglia (MG) which were cultured under non-stimulated conditions (−) or stimulated with LPS for 24 hrs prior to co-culture (+). NPCs were also treated with conditioned media (CM) from these same microglial cultures, CM from activated microglia that was pre-mixed with a blocking antibody to IL-6 (αIL6) or recombinant IL-6 in the presence or absence of blocking antibody. Data were collected as the fraction of GFP-expressing cells (NPCs) that co-express the early neuronal marker doublecortin. Co-culture with unstimulated microglia (−MG) had no effect on neuronal differentiation (Student's t test; P=0.53). Coculture with LPS-stimulated microglia decreased neurogenesis ($P<0.05$, relative to control or microglial co-culture) as did CM from activated but not resting microglia (Student's t test; $P<0.05$). A blocking antibody to IL-6 abrogates the CM effects and IL-6 alone (50 ng/ml) reproduced effects of activated microglial CM in reducing neurogenesis ($P<0.05$, n=3). Data are expressed as the fraction Dcx-positive cells relative to untreated control cultures. (B-D) Confocal micrographs of representative NPC cultures stained for green fluorescent protein which identifies progenitor cells (green) and neuronal double cortin (red). (B) Naïve cells. (C) Cells exposed to conditioned media from activated microglia. (D) Cells exposed to IL-6 (50 ng/ml). Scale bar, 15 µm. (E) Cell fate profile following IL-6 exposure. NPCs were induced to differentiate for 60 hours in the presence of IL-6 (50 ng/ml), and the percentage of cells expressing lineage-specific markers for neurons (type III β-tubulin, βTubulin), astroctyes (glial fibrillary acidic protein, GFAP) and immature oligodendrocytes (NG2 condroitin sulfate proteoglycans). Data are expressed as the fraction of cells positive for a given marker normalized to untreated controls. IL-6 caused a significant decrease in the proportion of cells adopting a neuronal fate ($P<0.05$; n=3), while astrogliogenesis and oligogliogenesis were unaffected. (F) TUNEL staining in Dcx-positive cells. As in A, cultures were treated with conditioned medium from LPS-stimulated microglia or treated directly with recombinant IL-6 (50 ng/ml). TUNEL was then scored in the total population (see text) as well as within the subset of cells that had adopted a neuronal phenotype (F). Apoptosis increased significantly overall but to a larger extent in neurons relative to non-neuronal cells.

and hilus are indicated. F. The area of the granule cell layer occupied by Iba-1 positive pixels was not different between control and irradiated animals or between wild type and MCP-1−/− animals indicating that irradiation did not increase microglial hypertrophy (see also FIG. 13). G. In contrast, the intensity of FA-11/CD68 staining on microglia increased in wild type but not MCP-1$^{-/-}$ animals following irradiation indicating that the absence of MCP-1 attenuated microglial proliferation and activation.

FIGS. 10A-10F Neurogenesis is normalized in MCP$^{-/-}$ animals following cranial irradiation. A, B, C. Confocal micrographs showing examples of immature, transition state, and mature neurons found within the hippocampal dentate gyrus of a non-irradiated wild type animal. Red=BrdU, Blue=NeuN, White=Dcx. Panels B and C show higher magnifications of areas b and c in panel A. Boxed areas in B and C are separated into individual fluorescent channels to the right. Asterisk in B indicates a BrdU-positive immature neuron that expressed only Dcx. Arrow in B indicates a transition-state neuron that expresses both Dcx and NeuN. Arrow in C indicates a mature neuron that no longer expresses Dcx .D. Stereological evaluation of the total number of BrdU-labeled nuclei per hippocampal dentate gyrus shows that a single 10Gy dose of cranial irradiation (rad) results in a 40-45% decrease in the production and retention of newborn cells one month after irradiation in both wild type (wt) and MCP-1$^{-/-}$ animals. E. The fraction of newborn cells that express the neuronal marker NeuN is reduced in wild type animals but not in MCP-1 null animals. F. Segregation of newborn neurons into immature (Dcx-only), transition state (Dcx+NeuN) or mature (NeuN-only) neurons shows that irradiation causes an accumulation of immature newborn cells that fail to mature. The absence of MCP-1 prevents this blockade.

FIGS. 11A-11E Depletion of newborn neuron arbors within the irradiated dentate gyrus occurs through an indirect mechanism. A Confocal evaluation of Dcx abundance and staining intensity shows that irradiation results in the specific depletion of Dcx-positive arbors within the dentate gyrus of wild type animals. The absence of MCP-1 attenuates this depletion. B, C, Quantification of the area of the dentate gyrus occupied by Dcx-positive arbors and the intensity of staining within Dcx-positive shows that the reduction in Dcx staining is primarily due the failure of cells to arborize rather than to an overall reduction in Dcx expression within positive cells. D, E, Direct application of increasing concentrations of MCP-1 to enriched neural progenitor cell populations in culture does not directly affect the differentiation of progenitors into Dcx-positive neurons nor the extent of neuronal arborization. Doublecortin (Dcx) expression is shown in cells treated with no rmMCP-1 (D) vs. 100 ug/ml rmMCP-1 (E). Quantification of the % of cells expressing Dcx after 5 days of differentiation and comparison of wild type cells to cells lacking either endogenous MCP-1 or its receptor CCR2 showed no differences in response to exogenously added rmMCP-1.

FIGS. 12A-12E The disruption of neurogenesis is not due to acute recruitment of peripheral macrophages into the neurogenic niche. A, B, Flow cytometric analysis of CD45 intensity within monocyte lineage cells isolated from control and irradiated brains one week after irradiation shows that there is no radiation-induced increase in the CD45-high fraction of peripheral monocytes present within the brains of either wild type or MCP-1−/− animals. C, D, E. Prussian blue staining for the presence of iron-labeled macrophages shows that radiation does not recruit a significant number of peripheral monocytes to either wild type or MCP-1−/− brains. In contrast, abundant iron-labeled macrophages are present in control brains following a focal ischemic stroke. A single blue stained macrophage can be seen in the cortex overlying the hippocampus of a wild type irradiated mouse brain (C and higher magnification in D). There were no iron-labeled microglia detected within the hippocampal formation (<0.5 cells/hippocampal section). In contrast to irradiation, an area of rat brain adjacent to a focal ischemic injury shows significant recruitment of iron-labeled peripheral macrophages (E).

Figure 9:
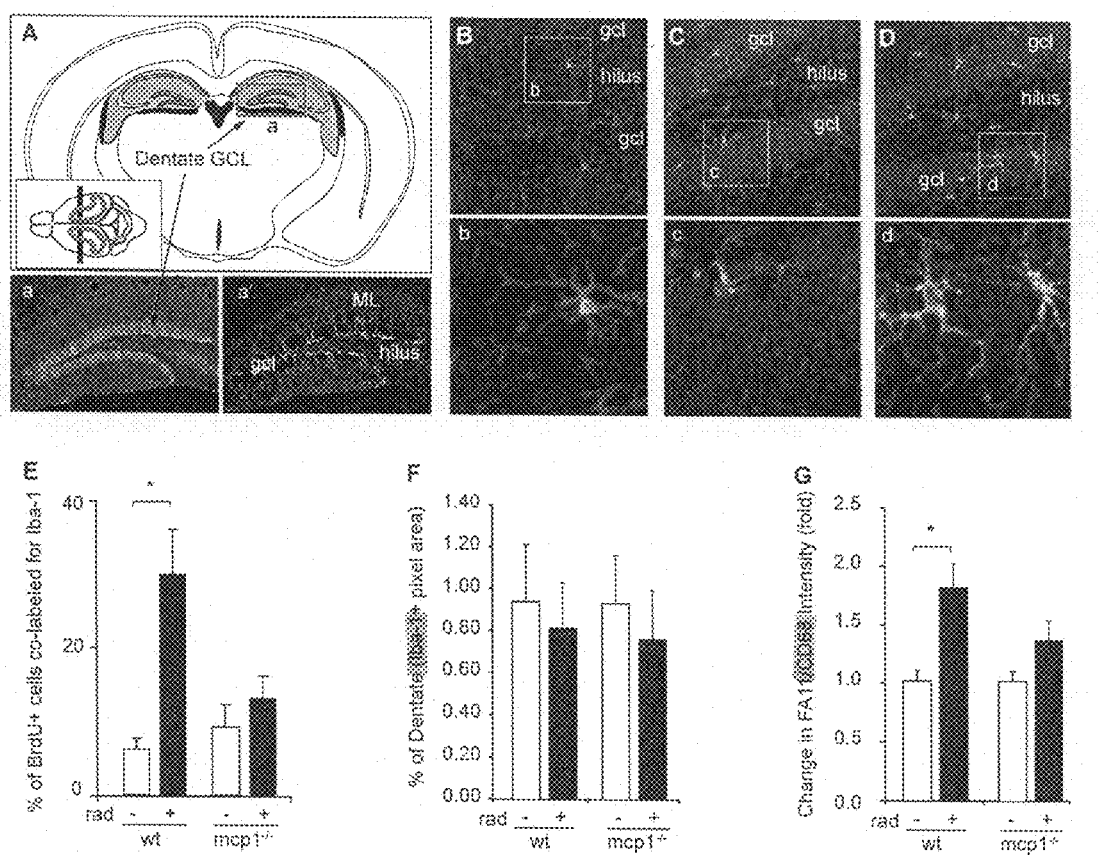
FIGS. 9A-9G Absence of MCP-1 attenuates radiation-induced monocyte proliferation and activation. A. A coronal schematic of the adult mouse brain shows the location of the hippocampal formation (grey) and dentate granule cell layer (blue) where neurogenesis continues throughout adult life. A confocal micrograph taken of the area outlined by the red box highlights the dentate granule cell layer in blue (a, a'). Mature neurons (NeuN-positive) are shown in blue (a), doublecortin-positive immature neurons are shown in green (a) or white (a') and BrdU-positive nuclei of newborn cells are shown in red (a, a'). The coronal section portrayed in A and the tissue section used in subsequent figures is taken at the approximate anterior-posterior level shown by the heavy bar in the sagittal view inset. The hippocampal formations are shown in red. Neural progenitor cells divide at the boundary between the granule cell layer and hilus to form a dense band of immature neurons that arborize extensively within molecular layer (ML in a'). The abundance of these newborn neurons correlates with hippocampus-dependent learning and memory. B, b, E. Irradiation (rad) is accompanied by an inflammatory response that includes increased proliferation of microglia in wild type (wt) animals but not in MCP-1$^{-/-}$ animals. The confocal micrograph in B shows Iba-1 positive microglia (green) adjacent to the granule cell layer (gcl) in an irradiated wild type animal. Many microglia are still proliferative (BrdU-positive, red, B, b) one month after a single 10 Gy dose of X-irradiation. The vascular bed is also shown in green (tomato lectin). Boxed area in B is shown at higher magnification in b. C, c, D, d. The activation of microglia following irradiation is attenuated in MCP-1 null animals. Microglia in control vs. irradiated wild type animals are shown in C and D respectively (Iba-1, green). A marker for microglial activation (FA-11, white) is more abundant following irradiation (D, d). Astrocyte processes are shown in red (GFAP) and cell nuclei are shown in blue (DAPI). Boxed areas of C and D are shown at higher magnification in c and d. The granule cell layer (gcl)

FIGS. 13A-13B Quantification of monocyte arborization and activation within sampled sections of the dentate gyrus. A. Confocal micrographs show grayscale images of NeuN (top row), Iba-1 (middle row) and FA-11/CD68 staining in wild type or MCP-1 mice following irradiation. A representative section from the indicated genotype is presented in each column. Markers for each row are indicated at the left. Confocal settings are identical for all images across each row. Total monocyte number or hypertrophy does not change following irradiation. FA-11 staining increases in wild type animals following irradiation but to a lesser extent in MCP-1−/− animals. B. Quantitative measures of microglial area and activation state shown in FIG. 9 were determined within the neurogenic area of the dentate granule cell layer (the region is outlined in A and cropped images from the wild type irradiated sample are shown in B). Iba-1 positive pixels that stained above background were then identified within this region and the intensity of FA-11 within the Iba-1-positive pixels then quantified. The same method was used to measure Dcx-positive neuron arborization within the granule cell layer in FIG. 11.

FIGS. 14A-14F Magnetic resonance imaging to detect iron-mediated quenching of T2-weighted image intensity. Panels A-D show coronal images of irradiated (A, B) or non-irradiated (C, D) mouse brain. Irradiation was limited to the right hand hemisphere as shown. Panels E, F show coronal image s of a rat brain 7 days after middle cerebral artery occlusion. Right hand panels are prior to intravenous superparamagnetic iron oxide particle (SPIO, Combidex) injection. Left hand panels are from the same animals 24 hrs after SPIO injection. Areas of macrophage recruitment following stroke are hypointense following the extravasation of monocytes that had phagocytized iron in circulation. No areas of iron-hypointensity are detected in the right hand hemispheres of mice exposed to 10 Gy X-irradiation confirming that peripheral monocyte extravasation is minimal in the week following cranial irradiation but may contribute to chronic neurogenic defects in the months following injury.

FIGS. 15A-15J LPS produces flu-like illness that is associated with decreased hippocampal neurogenesis. Adult female C57Bl/6 mice were given a single intraperitoneal (i.p.) injection of e. coli lipopolysaccharide (LPS) at either 0, 5, 7.5 or 10 mg/kg to induce flu-like illness and daily i.p. injections of bromodeoxyuridine (BrdU; 50 mg/kg) for 6 days to label proliferating cells. The mice were perfused on the $7^{th}$ (n=5 or 6 per group) or $28^{th}$ day (n=4 per group) after LPS injection to evaluate the effects of transient illness on hippocampal neurogenesis. LPS-treated mice exhibited sickness behavior (hunching behavior, piloerection, and sweaty fur) within 1-2 h and lost approximately 10% of their body mass within 2 d following LPS injection (p's<0.001 on Days 1-4). Days to recovery increased with higher doses of LPS ($F_{(6,36)}$=11.21; 5 mg/kg=4 d, p's<0.001, 7.5 mg/kg=5 d, p's<0.01, 10 mg/kg=6 d p's<0.01). A) Schematic drawing of a coronal section through the mouse brain at the level of the rostral hippocampal formation (yellow boxed area). Neurogenesis occurs in the dentate gyrus (blue) of the hippocampus. Light micrographs of anatomically matched sections through the dentate gyri show that monocyte/microglial (IBA-1-stained cells) were roughly equivalent in number in vehicle (B) vs. LPS (C) treated animals. Stereological estimates of total IBA-1-positive cell number confirmed this effect ($t_{(6)}=1.16$; p=0.32) (D). However, microglia in LPS treated animals were larger in size (B vs. C) and stained more intensely for FA-11 ($t_{(6)}=1.80$; p=0.06, one-tailed) (E), a marker for activation. Activation level was determined using Photoshop to measure mean FA-11-conjugated fluorophore pixel intensity where IBA-1-conjugated fluorophore pixels were observed on sections scanned using a 10× objective. F, G) Neurogenesis was evaluated by staining hippocampal sections for BrdU (red) doublecortin (Dcx, green, a marker for immature neurons) or Neun (blue) a marker for more mature neurons. Arrows in F show representative NeuN-positive newborn neurons (blue) that are labeled with BrdU (red). Quantification of the number new born cells (H) showed that LPS did not significantly affect the number of BrdU-labeled cells produced and surviving for 7 ($t_{(6)}=0.18$, p=0.82) or 28 ($t_{(6)}=0.56$; p=0.60) days after LPS treatment. However, the fraction of BrdU-labeled cells acquiring a neuronal phenotype was significantly reduced by LPS treatment in mice perfused at both 1 week ($F_{(6,36)}=3.75$) and at 4 weeks ($F_{(2,12)}=3.81$) following injection (I, J, respectively). Within 1 week, LPS treatment significantly depletes the intermediately mature (BrdU/DCX/NeuN-double positive) population of new neurons (p's<0.005), presumably leading to the depletion of mature neurons (BrdU/NeuN-positive) observed 4 weeks after treatment (p=0.02).

FIGS. 16A-16G LPS treatment causes acute weight loss but cognitive function quickly recovers. A) LPS-treated mice exhibited sickness behavior (hunching behavior, piloerection, and sweaty fur) within 1-2 h and lost approximately 10% of their body mass within 2 d following LPS injection (p's<0.001 on Days 1-4). Days to recovery increased with higher doses of LPS ($F_{(6,36)}=11.21$; 5 mg/kg=4 d, p's<0.001, 7.5 mg/kg=5 d, p's<0.01, 10 mg/kg=6 d p's<0.01). Because higher doses of LPS (7.5 and 10 mg/kg doses) only prolonged recovery of body weight but did not increasingly inhibit neurogenesis in a dose dependent manner (FIG. 15I), all other data was derived from mice treated with 5 mg/kg dose. To test the short term effects of inflammation on mouse behavior and cognition, adult C57Bl/6 female were given an i.p. injection of 5 mg/kg LPS or vehicle and were then tested behaviorally one week following LPS treatment (n=12 per group). LPS-treated mice exhibited slightly impaired locomotor activity while recovering from transient illness (Day 4 post-LPS injection) relative to vehicle-treated mice. B) Although LPS-treated mice and vehicle-treated mice (n=12 per group) initiated the same number of exploratory bouts in a novel chamber ($F_{(1,22)}=2.33$; p=0.14), the total distance explored ($F_{(1,22)}=5.56$; p=0.03) and duration spent exploring ($F_{(1,22)}=5.25$; p=0.03) in a session was significantly smaller in LPS-treated mice. The effect of LPS treatment on distance and duration of exploration was most evident in the latter half of the session (p's<0.0001), suggesting that LPS-treated mice tired more easily than vehicle-treated mice, perhaps exhibiting the malaise often reported to accompany viral-induced sickness behavior. However, LPS-treated mice learned the location of a visible platform as well as vehicle-treated mice (C) (Days 5-7; effect of session $F_{(5,110)}=42.72$, p<0.001; interaction effect, $F_{(5,110)}=0.19$; p=0.97), exhibiting similar swim speeds on all trials (vehicle=24.31±1.13 and LPS=26.59±1.32 [mean±SEM]; $F_{(5,110)}=0.20$; p=0.96), suggesting that LPS-induced illness did not impair sensorimotor ability or motivation to escape the aversively motivated maze. Distance swum to a hidden platform in the Morris water maze task decreased similarly across training sessions in both groups ($F_{(7,98)}=11.14$; p<0.001) (D) and both groups remembered the position of the hidden platform equally well as indicated by a preference for swimming in the platform quadrant of the pool after the platform had been removed (E). F,G) When training trials commenced 4 weeks after an LPS challenge, LPS-treated mice spent a significantly smaller amount of time than control mice searching the pool quadrant that house the platform on training trials (G), despite learning the location of the platform as well as control mice on training trials (F).

FIG. 17A-17D Broad spectrum or PPAR-γ-selective selective NSAIDs attenuate the effects of illness on neurogenesis and memory. Animals were started on a preventative course of oral NSAID and then challenged with a single IP injection of LPS (5 mg/kg). All LPS injected animals showed similar overt sickness behavior and weight loss following LPS injection was not significantly affected by the administration of one of three NSAIDs, Indomethacin (Indo), Celebrex (Cele), Rosiglitizone (Rosi) (A). Evaluation of neurogenesis in hippocampi of treated and non-treated animals (B) showed that the fraction of cells born on days 0-6 that adopted a neuronal fate (doublecortin and/or NeuN expression) by day 28 was significantly reduced following LPS injection. Administration of indomethacin (Indo) attenuated this deficit. Celebrex (Cele) had no protective effect while rosiglitizone (Rosi) completely prevented the deficits in neurogenesis. Evaluation of the maturity of 3-4 week old neurons shows that most newborn neurons in control animals matured into NeuN expressing cells(C). Many of these were still retained doublecortin expression along with NeuN (Dcx+NeuN) indicating that they were still maturing. Very few cells remained positive for Dcx alone by 28 days after BrdU labeling. Transient illness significantly altered the ratio of immature (Dcx) to transition-state (Dcx+NeuN) or mature (NeuN) neurons. LPS injection led to a small but significant increase in the fraction of cells that remained immature and a significant decrease in transition-state and mature neurons. Panel D shows a confocal micrograph demonstrating immature, transition-state and mature newborn neurons. Arrows indicate a BrdU-positive (red) NeuN positive (green) mature neuron that is not Dcx positive (blue). The arrowhead shows a BrdU-positive neuron that is still transitioning from immature to mature neuron (i.e., both NeuN and Dcx positive).

Figure 18:
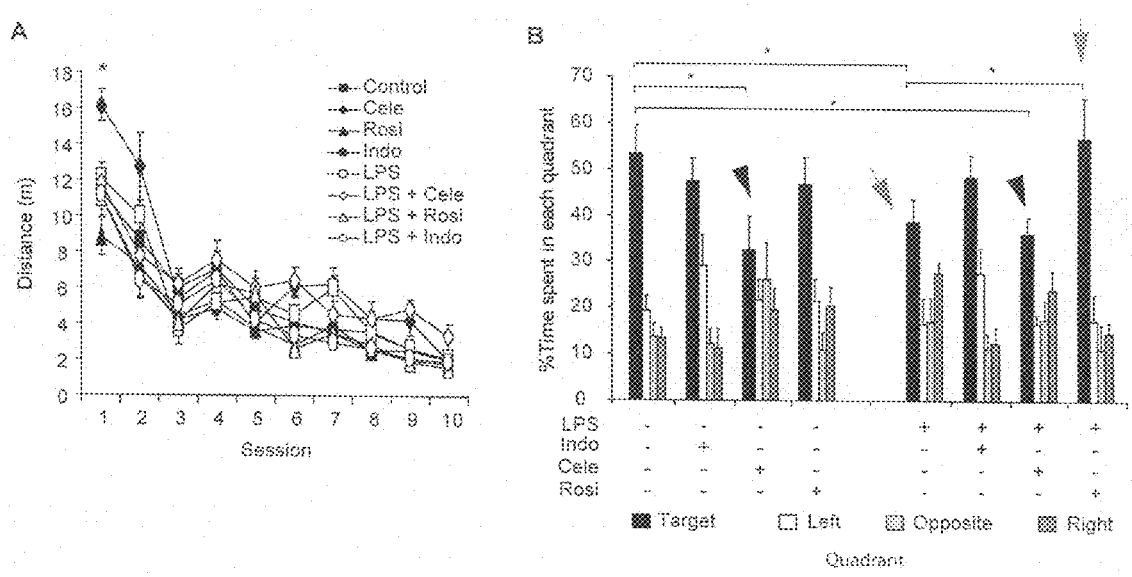

FIG. 18A-18B Analysis of learning and memory in control and LPS-treated animals one starting one month after illness, a time when newborn neurons that were altered by inflammation are integrated and functioning within the hippocampus. A) Distance swum in training trials where animals learn the position of the hidden escape platform show normal learning curves for all animals regardless of LPS or NSAID treatment suggesting that spatial learning in the Morris water maze was unaffected by LPS (with the exception of an slight but significant initial increase in swimming distance in animals that were treated with celebrex alone). B)Transient illness did, however lead to a significant impairment in recall of the platform position in LPS-treated animals vs. controls (red arrow) when animals were tested in the maze but with the platform removed. Black columns indicate time spent in the quadrant where animals had learned that the platform was located (target), white, or grey bars represent time spent in the non-target quadrants. The bigger the difference between black bar and the other bars, the stronger the memory. This inflammation-induced memory impairment was partially attenuated by indomethacin administration and fully protected by the PPARγ agonist rosiglitizone (green arrow). Of particular note, the cox-2 antagonist, although well tolerated, alone significantly impaired memory, even in the absence of inflammatory challenge (arrowheads) and had no significant beneficial effect on restoring memory. Combined, this data demonstrates that inflammation impairs neurogenesis which alters hippocampal memory function, but not acutely after sickness. Only after the newborn neurons have matured sufficiently to be functionally integrated into the hippocampal neural network. Thus, reduced neurogenesis during illness results in a hippocampus that operates on fewer new neurons in the following months. Broad spectrum NSAIDs such as indomethacin are effective if tolerated and PPAR-gamma agonists are particularly effective in protecting neurogenesis and memory following inflammatory challenge.

DETAILED DESCRIPTION OF THE EMBODIMENTS

Methods are provided for protecting an individual from adverse long-term effects of deficits in neurogenesis that can follow acute or chronic neuroinflammation. Inflammatory blockade with a general or specific anti-inflammatory drug prevents a loss of neurogenesis capacity after, for example, cranial irradiation, or other neuroinflammatory conditions, including naturally occurring and induced episodes of inflammation. This inflammatory blockade reduces the direct effects of activated microglia on neural precursor cells and restores the cytokine-interrupted signaling by neighboring cells that is necessary to support neurogenesis. These cells include the essential cellular components of the stem/progenitor cell local microenvironment, e.g. microvascular endothelium, smooth muscle, astrocytes and neurons. These findings have broad implications for a variety of diseases of cognition involving neuroinflammation, inflammatory cytokines and stem cell/precursor cell dysfunction.

In one embodiment of the invention, inflammatory blockade is coupled with cranial radiation therapy. Cranial radiation can cause a progressive decline in cognition that is linked to long-term ablation of hippocampal neurogenesis. Robust microglial inflammation accompanies irradiation-induced, microenvironmental failure and mediates the neurogenic failure. Cranial irradiation increases the production of pro-inflammatory cytokines and chemokines in the brains of both mice and men, in particular the production of MCP-1; IL-6; and TNF-α.

The methods of the invention are useful in prevention of cognitive radiation damage from a variety of sources of ionizing radiation, including X-rays, gamma-rays, beta radiation and alpha radiation. Such radiation may result from exposure to nuclear fusion or fission materials, e.g. nuclear waste, nuclear weapons, or nuclear power plants, from intentional or unintentional exposure to radiation, e.g. X-rays, gamma rays, etc. for medical or other purposes.

The methods are also useful in preventing cognitive damage that results from neuroinflammation, immune cytokines and precursor cell dysfunction in a variety of diseases including Alzheimer's disease, Parkinson's disease, Huntington's disease, lysosomal storage disorders involving inflammatory response, multiple sclerosis or other auto-immune disease, depression, bipolar disorder, or Cushing's disease and other iatrogenic hyperglucocorticoid "Cushingoid" states.

Additional diseases benefit from these methods due to their known recruitment of immune-mediated processes and accompanying deficits in cognition, in which defects in neurogenesis are implicated. These include Lewy Body dementia, Frontotemporal dementia/Pick's disease, AIDS dementia complex, dementia puligistica and chronic cognitive dysfunction following head trauma, prion-associated dementia such as Creutzfeldt-Jacob disease, cognitive dysfunction following chronic seizure disorders or an episode of, status epilepticus, cognitive dysfunction following encephalitis or meningitis, amyotrophic lateral sclerosis (ALS)/parkinsonian/dementia complex of Guam.

In one embodiment, the methods are also useful for attenuating the inflammatory effects on neurogenesis following acute injury, such as traumatic injury, ischemia, cerebral hemorrhage, or stroke. In another embodiment, the methods are useful for attenuating the effects of pre- or peri-natal ischemia/hemorrhage associated with the developmental dysregulation of stem/progenitor cells in early life.

The methods of the invention find use in the treatment of post-trauma or post-surgical control of brain inflammation or other inflammatory processes, which are currently treated with exogenous corticosteroids, as corticosteroids intrinsically inhibit neurogenesis and accentuate the already detrimental effects of neuroinflammation on neurogenesis. In the stress/depression context, post-traumatic stress disorder is expected to have a cytokine/inflammation mediated dysfunction, treatable by the methods of the invention.

The methods are used for augmenting abortive neurogenesis that occurs in response to surgical interventions, injury, or disease but which is attenuated by virtue of an accompanying immune response.

The methods of the invention find use in minimizing the negative influence of inflammation in cell or tissue transplantation to the central nervous system, where such grafts include neural progenitors such as those found in fetal tissues, neural stem cells, embryonic stem cells or other cells and tissues contemplated for neural repair or augmentation. Neural stem/progenitor cells have been described in the art, and their use in a variety of therapeutic protocols has been widely discussed. For example, inter alia, U.S. Pat. No. 6,638,501, Bjornson et al.; U.S. Pat. No. 6,541,255, Snyder et al.; U.S. Pat. No. 6,498,018, Carpenter; U.S. Patent Application 20020012903, Goldman et al.; Palmer et al. (2001) Nature 411(6833):42-3; Palmer et al. (1997) Mol Cell Neurosci. 8(6):389404; Svendsen et al. (1997) Exp. Neurol. 148(1): 135-46 and Shihabuddin (1999) Mol Med Today. 5(11):474-80; each herein specifically incorporated by reference.

Neural stem and progenitor cells can participate in aspects of normal development, including migration along well-established migratory pathways to disseminated CNS regions, differentiation into multiple developmentally- and regionally-appropriate cell types in response to microenvironmental cues, and non-disruptive, non-tumorigenic interspersion with host progenitors and their progeny. Human NSCs are capable of expressing foreign transgenes in vivo in these disseminated locations. A such, these cells find use in the treatment of a variety of conditions, including traumatic injury to the spinal cord, brain, and peripheral nervous system; treatment of degenerative disorders including Alzheimer's disease, Huntington's disease, Parkinson's disease; affective disorders including major depression; stroke; and the like. During the physical manipulation involved in transplantation, physical damage can cause neuroinflammation, which then limits the ability of the transplanted cells to thrive in the recipient environment. By administering anti-inflammatory agents, the deleterious effects of neuroinflammation are reduced, providing enhanced engraftment and neuron growth.

The methods find use in developing ligand-targeted compound or gene delivery systems where detection, diagnosis, and clinical monitoring of immune-mediated stem/progenitor cell dysfunction is desired. Such strategies include the use of anti-inflammatory agents to validate the predictive nature of the detection method(s) in correcting or modifying stem/progenitor cell function.

The similarities between neural stem cells in the central and peripheral nervous system also indicate that these methods are useful in augmenting neural tissue repair in the peripheral nervous system, where local inflammation may prevent optimum healing or restoration of innervation by virtue of neural stem/progenitor cell dysfunction. Such diseases or injury may include nerve injury due to trauma, surgery, cancer, or immune disease such as multiple sclerosis, ALS, or other motor neuron disease where endogenous or grafted progenitor/stem cells are influenced by immune mechanisms.

General anti-inflammatory agents useful in protection of neurogenesis include those drugs generally classified as non-steroidal anti-inflammatory drugs (NSAIDs). By way of example and not limitation, NSAIDs useful in the practice of the invention include fenoprofen calcium, nalfon, flurbiprofen, Ansaid, ibuprofen, ketoprofen, naproxen, anaprox, aflaxen, oxaprozin, diclofenac sodium, diclofenac potassium, cataflam, etodolac, indomethacin, ketorolac tromethamine, nabumetone, sulindac, tolmetin sodium, fenamates, meclofenamate sodium, mefenamic acid, piroxicam, salicylic acid, diflunisal, aspirin, oxyphenbutazone, and phenylbutazone.

A subpopulation of microglia involved in deleterious inflammation are peripheral blood monocytes/microglia, which contribute to chronic neuroinflammatory lesions within the brain by entry across the blood brain barrier resulting from altered patterns of leukocyte trafficking. The altered patterns result from changes in chemokine and/or leukocyte adhesion molecule signaling. In addition to general anti-inflammatory agents, specific agents, e.g. those known in the art, that interrupt the recruitment of leukocytes to the brain are of interest as therapeutic agents. Compound screening can also be performed to identify agents that specifically interfere with the trans-endothelial migration of monocytes/microglia. Anti-inflammatory agents are particularly effective at decreasing this subpopulation of infiltrating, proliferating peripheral monocytes.

Various adhesion and chemokine molecules have been implicated in leukocyte trafficking to the brain. Vries et al. (2002) J Immunol. 168(11):5832-9 states that signal-regulatory protein (SIRP)alpha-CD47 increases monocytetransmigration across brain ECs. CD47 is expressed on cerebral endothelium, while SIRPalpha and CD47 are expressed on monocytes. James et al. (2003) *J Immunol.* 170(1):520-7 found that blockade of alpha$_4$ integrin or VCAM-1 inhibited leukocyte rolling and adhesion to the cerebral vasculature. The chemokines monocyte chemoattractant protein-1 (MCP-1 or CCL2) and IL-8 have also been implicated in brain leukocyte trafficking, as well as SDF-1, MIP-1 alpha (CCL3), MIP-1 beta, RANTES (CCL5), eotaxin (CCL11), and MIP-2.

As shown in the examples, in the absence of MCP-1 the deleterious effects associated with events that create neuroinflammation are abrogated. Therefore, agents of particular interest include antagonists and inhibitors of MCP-1. Many such agents have been described in the art, and may find use in the methods of the invention. Such agents include small molecules; polypeptides; antisense and siRNA; and the like. Small molecule antagonists include, without limitation, 5-(((S)-2,2-dimethylcyclopropanecarbonyl)amino)phenoxy) pyridine (APC0576, described by Yuzawa et al. (2003) Transplantation 75:1463-1468); 2-methyl-2-[[1-(phenylmethyl)-1H-indazol-3yl]methoxy]propanoic acid (Bindarit, described by Sironi et al. (1999) European Cytokine Network 10:437-442); 17β-estradiol (described by Kanda et al. (2003) J Invest Dermatol. 120(6):1058-66); trans-3,4-dichloro-N-methyl-N[2-(1-pyrolidinyl)cyclohexyl]benzeneacetamide methanesulfonate (U50,488, described by Sheng et al. (2003) Biochem Pharmacol. 65(1):9-14); doxazosin, described by Kintscher et al. (2001) J Cardiovasc Pharmacol. 37(5):532-9). Polypeptide antagonists include, without limitation, NH(2)-terminal-truncated MCP-1 (described by Hasegawa et al. (2003) Arthritis Rheum. 48(9):2555-66); 7ND (described by Shimizu et al. (2003) J Am Soc Nephrol. 14(6):1496-505); eotaxin-3 (described by Ogilvie et al. (2003) Blood 102(3): 789-94). RNA based antagonists include high affinity aptamers, e.g. ADR7 and ADR22 as described by Rhodes et al. (2001) FEBS Lett. 506(2):85-90.

Other agents of interest are targeted to specifically block the activity of interleukin-6 (IL-6), as IL-6 is shown herein to suppress hippocampal neurogenesis. IL-6 is a pleiotropic cytokine with a wide range of biological functions. These IL-6 functions are mediated through a receptor system composed of two different molecules on the cell surface. One is an IL-6 binding molecule, IL-6 receptor (IL-6R), and the other is a common signal transducer for IL-6 family cytokines, gp130. Following the binding of IL-6 with IL-6R, the IL-6 signal is transduced into the cells through gp130, which binds the complex of IL-6 and IL-6R. Two types of IL-6R molecules exist in vivo. One is the above-mentioned membrane-bound IL-6R (80 kd), and the other is a soluble form of IL-6R (50 kd, sIL-6R), which is secreted into the serum by the alternative splicing of mRNA and the enzymatic cleavage of 80 kd IL-6R on the cell surface. This sIL-6R can also mediate the IL-6 signal into cells via gp130 in the same way as IL-6R, so that IL-6R functions as an agonist to the IL-6 signal transduction.

Functional blocking of IL-6 activity may be achieved by inhibiting IL-6 production; neutralizing IL-6 protein; blocking IL-6 binding to IL-6R; blocking IL-6/IL-6R complex binding to gp130 molecule, suppressing IL-6R and/or gp130 expression; or blocking intracytoplasmic signal transduction through gp130. In a preferred embodiment, a specific binding agent is used to block IL-6 binding to IL-6R. Humanized antibodies that bind to the IL-6R are known in the art (Yoshizaki et al. (1998) *Springer Semin Immunopathol* 20:247).

In addition to IL-6; other cytokines have been shown to act on the vasculature and/or neuronal stem cells and to reduce neurogenesis. Such cytokines include IL-1β, and TNFα. IL-1β is a pro-inflammatory cytokine that appears in brain and cerebrospinal fluid following peripheral immune challenges and central infections or injury. The cytokine has a systemic effect, and may additionally have a specific effect on vascular endothelial cells. IL-1β has also been credited with inducing expression of MCP-1 and intercellular adhesion molecule-1 (ICAM-1). It may trigger a targeted leukocyte emigration and widespread glial activation (see Proescholdt et al. (2002) *Neuroscience* 112(3):731-49).

Antagonists that block the activity of these cytokines may also find use in the methods of the invention. Many agents that block activity of TNFα are described in the art, for example see U.S. Patent Application 20010022978; U.S. Pat. No. 6,537,540; etc. Both antibody and small molecules inhibitors of IL-1b have been described, for example see U.S. Pat. Nos. 6,541,623; 6,511,665; 6,337,072; 6,133,274; etc.

Also demonstrated by the examples is the efficacy of using agents that are agonists to peroxisome-proliferator-activated receptors (PPARs) to reduce neuroinflammation. Therefore, agents of interest also include compounds that result in the activation of PPARs. The PPARs are members of the nuclear hormone receptor superfamily of ligand-activated transcription factors related to retinoid, steroid and thyroid hormone receptors. Like other nuclear receptors the PPAR is activated by its binding to a ligand, and its subsequent binding to a response sequence existing upstream of a target gene domain activates the trancription of that gene. PPARs form heterodimers with retinoid X receptor (RXR) and bind to their response elements in this heterodimeric form. Of the three known subtypes of PPARs, PPAR-γ plays the most prominent role in the regulation of the inflammatory response (Blanquart et al., J. Stereochem. Mol. Bio., vol. 85, pp. 267-73, 2003). Agonists of PPAR-γ are known to the art. Thiazolidinediones (TZDs) are synthetic PPAR-γ agonists. This class of agonists includes, without limitation, such compounds as pioglitazone, ciglitazone and rosiglitazone (Lehmann et al., J. Biol. Chem., vol. 270, pp. 12953-6). Activation of PPAR-γ has been shown to inhibit the release of inflammatory mediators from activated monocytes and macrophages, to inhibit the production of COX-2 and to downregulate NFKB transcription (See Jiang et al., Nature, vol. 391, pp. 82-6, 1998; Ricote et al., Nature, vol. 391, pp. 79-82, 1998; Guyton et al., Shock, vol. 20, pp. 56-62, 2003). Accordingly, TZDs and compounds with similar activity may find use in the invention. One preferred embodiment of the invention includes introducing agonists of PPAR-γ into a subject to reduce neuroinflammation.

Therapeutic formulations of general and specific anti-inflammatory agents, including MCP-1 blocking agents, IL-6 blocking agents and PPAR-γ agonists, are provided. In one aspect of the invention, the anti-inflammatory agent is administered to individuals having an increased chance of cranial radiation toxicity. The formulations find use as protective agents, for example, in cancer patients treated with ionizing radiation. The agent can be administered locally or systemically against anticipated radiation exposure, e.g. radiation therapy or exposure resulting from workplace radiation, military exposure, and the like. In another embodiment, the agent is administered locally or systemically immediately following accidental or unintentional exposure.

The compounds of the present invention are administered at a dosage that protects the cell population while minimizing any side-effects. It is contemplated that the composition will be obtained and used under the guidance of a physician for in vivo use. The dosage of the therapeutic formulation will vary widely, depending upon the nature of the disease, the frequency of administration, the manner of administration, the clearance of the agent from the host, and the like.

In one embodiment of the invention, the anti-inflammatory agent is administered in conjunction with cranial radiation treatment of a tumor. Tumors for which cranial radiation may be indicated include primary brain tumors, tumors metastatic to the brain, central nervous system involvement of leukemias and lymphomas, and head and neck cancers, or other cancers or neoplasias that involve radiation treatment fields that include the central nervous system. Several methods of interest include the combination administering an anti-inflammatory agent in conjunction with whole body irradiation as administered in bone marrow transplant, cranial irradiation as used to treat diffuse tumors of the head and neck, focal irradiation as delivered by the CyberKnive or equivalent shaped field or restricted beam delivery system such as a proton beam, GliaSite radiation, which irradiates cancerous cells from within the tumor cavity, or ligand-targeted delivery of radioactive agents such as antibody-linked or synthetic molecule linked radio-ablative compounds.

Brain tumors are classified according to the kind of cell from which the tumor seems to originate. Diffuse, fibrillary astrocytomas are the most common type of primary brain tumor in adults. These tumors are divided histopathologically into three grades of malignancy: World Health Organization (WHO) grade II astrocytoma, WHO grade III anaplastic astrocytoma and WHO grade IV glioblastoma multiforme (GBM). Biological subsets of primary brain tumors include adrenocartical carcinoma; brain stem gliomas; pleomorphic xanthoastrocytoma (PXA); pilocytic astrocytoma; subependymal giant cell astrocytomas; desmoplastic cerebral astrocytoma of infancy (DCAI); desmoplastic infantile ganglioglioma; oligodendrogliomas; oligoastrocytomas (mixed gliomas); ependymomas; supratentorial intraventricular tumors; benign cerebellopontine angle tumors; medulloblastomas; meningiomas; schwannomas; hemangioblastomas; and hemangiopericytomas. Brain metastases are one of the most common sites of systemic spread from solid tumors. Metastatic cancers of the brain include, without limitation, non-small cell lung cancer; breast cancer; melanoma; renal and colon cancers; and the like. Primary central nervous system (CNS) lymphoma is a malignant neoplasm of lymphocytic derivation that is localized to the nervous system. The incidence of these tumors is rising relative to other brain lesions due to the occurrence of primary lymphoma in AIDS and transplant patients. Most common supratentorial locations are the frontal lobes, then deep nuclei and periventricular zone.

Surgery is often used in the treatment of brain tumors to remove or reduce as much of its bulk as possible. By reducing the size of tumor mass, radiotherapy can be more effective. Stereotaxy is a useful adjunct to surgery and radiotherapy (stereotactic radiotherapy). The compositions of the invention may be administered using any medically appropriate procedure, e.g., intravascular (intravenous, intraarterial, intracapillary) administration, injection into the cerebrospinal fluid, intracavity or direct injection in the tumor. Intrathecal administration maybe carried out through the use of an Ommaya reservoir, in accordance with known techniques. (F. Balis et al., Am J. Pediatr. Hematol. Oncol. 11, 74, 76 (1989).

The effective amount of a therapeutic composition to be given to a particular patient will depend on a variety of factors, several of which will be different from patient to patient. Utilizing ordinary skill, the competent clinician will be able to optimize the dosage of a particular therapeutic or imaging composition in the course of routine clinical trials. One thiazolidinedione currently used clinically for the treatment of Type II diabetes mellitus, rosiglitazone, is used at a dosage range of about 0.04 to 0.16 mg/kg. For the purposes of the present invention, a higher dose may be contemplated, for example at a dosage range of at least about 0.04, at least about 0.1, at least about 0.5, at least about 1, and not more than about 5, usually not more than about 2 mg/kg.

Anti-inflammatory agents can be incorporated into a variety of formulations for therapeutic administration by combination with appropriate pharmaceutically acceptable carriers or diluents, and may be formulated into preparations in solid, semi-solid, liquid or gaseous forms, such as tablets, capsules, powders, granules, ointments, solutions, suppositories, injections, inhalants, gels, microspheres, and aerosols. As such, administration of the compounds can be achieved in various ways, including oral, buccal, rectal, parenteral, intraperitoneal, intradermal, transdermal, intracheal, etc., administration. The active agent may be systemic after administration or may be localized by the use of regional administration, intramural administration, or use of an implant that acts to retain the active dose at the site of implantation.

One strategy for drug delivery through the blood brain barrier (BBB) entails disruption of the BBB, either by osmotic means such as mannitol or leukotrienes, or biochemically by the use of vasoactive substances such as bradykinin. The potential for using BBB opening to target specific agents to brain tumors is also an option. A BBB disrupting agent can be co-administered with the therapeutic compositions of the invention when the compositions are administered by intravascular injection. Other strategies to go through the BBB may entail the use of endogenous transport systems, including carrier-mediated transporters such as glucose and amino acid carriers, receptor-mediated transcytosis for insulin or transferrin, and active efflux transporters such as p-glycoprotein. Active transport moieties may also be conjugated to the therapeutic or imaging compounds for use in the invention to facilitate transport across the epithelial wall of the blood vessel. Alternatively, drug delivery behind the BBB is by intrathecal delivery of therapeutics or imaging agents directly to the cranium, as through an Ommaya reservoir.

Pharmaceutical compositions can include, depending on the formulation desired, pharmaceutically-acceptable, non-toxic carriers of diluents, which are defined as vehicles commonly used to formulate pharmaceutical compositions for animal or human administration. The diluent is selected so as not to affect the biological activity of the combination. Examples of such diluents are distilled water, buffered water, physiological saline, PBS, Ringer's solution, dextrose solution, and Hank's solution. In addition, the pharmaceutical composition or formulation can include other carriers, adjuvants, or non-toxic, nontherapeutic, nonimmunogenic stabilizers, excipients and the like. The compositions can also include additional substances to approximate physiological conditions, such as pH adjusting and buffering agents, toxicity adjusting agents, wetting agents and detergents.

The composition can also include any of a variety of stabilizing agents, such as an antioxidant for example. When the pharmaceutical composition includes a polypeptide, the polypeptide can be complexed with various well-known compounds that enhance the in vivo stability of the polypeptide, or otherwise enhance its pharmacological properties (e.g., increase the half-life of the polypeptide, reduce its toxicity, enhance solubility or uptake). Examples of such modifications or complexing agents include sulfate, gluconate, citrate and phosphate. The polypeptides of a composition can also be complexed with molecules that enhance their in vivo attributes. Such molecules include, for example, carbohydrates, polyamines, amino acids, other peptides, ions (e.g., sodium, potassium, calcium, magnesium, manganese), and lipids.

Further guidance regarding formulations that are suitable for various types of administration can be found in Remington's Pharmaceutical Sciences, Mace Publishing Company, Philadelphia, Pa., 17th ed. (1985). For a brief review of methods for drug delivery, see, Langer, Science 249:1527-1533 (1990).

The pharmaceutical compositions can be administered for prophylactic and/or therapeutic treatments. Toxicity and therapeutic efficacy of the active ingredient can be determined according to standard pharmaceutical procedures in cell cultures and/or experimental animals, including, for example, determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit large therapeutic indices are preferred.

The data obtained from cell culture and/or animal studies can be used in formulating a range of dosages for humans. The dosage of the active ingredient typically lines within a range of circulating concentrations that include the $ED_{50}$ with low toxicity. The dosage can vary within this range depending upon the dosage form employed and the route of administration utilized.

The pharmaceutical compositions described herein can be administered in a variety of different ways. Examples include administering a composition containing a pharmaceutically acceptable carrier via oral, intranasal, rectal, topical, intraperitoneal, intravenous, intramuscular, subcutaneous, subdermal, transdermal, intrathecal, and intracranial methods.

For oral administration, the active ingredient can be administered in solid dosage forms, such as capsules, tablets, and powders, or in liquid dosage forms, such as elixirs, syrups, and suspensions. The active component(s) can be encapsulated in gelatin capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate. Examples of additional inactive ingredients that may be added to provide desirable color, taste, stability, buffering capacity, dispersion or other known desirable features are red iron oxide, silica gel, sodium lauryl sulfate, titanium dioxide, and edible white ink. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract. Liquid dosage forms for oral administration can contain coloring and flavoring to increase patient acceptance.

The active ingredient, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

The components used to formulate the pharmaceutical compositions are preferably of high purity and are substantially free of potentially harmful contaminants (e.g., at least National Food (NF) grade, generally at least analytical grade, and more typically at least pharmaceutical grade). Moreover, compositions intended for in vivo use are usually sterile. To the extent that a given compound must be synthesized prior to use, the resulting product is typically substantially free of any potentially toxic agents, particularly any endotoxins, which may be present during the synthesis or purification process. Compositions for parental administration are also sterile, substantially isotonic and made under GMP conditions.

The compositions of the invention may be administered using any medically appropriate procedure, e.g., intravascular (intravenous, intraarterial, intracapillary) administration, injection into the cerebrospinal fluid, intracavity or direct injection in the tumor. Intrathecal administration maybe carried out through the use of an Ommaya reservoir, in accordance with known techniques. (F. Balis et al., Am J. Pediatr. Hematol. Oncol. 11, 74, 76 (1989). For the imaging compositions of the invention, administration via intravascular injection is preferred for pre-operative visualization of the tumor. Post-operative visualization or visualization concurrent with an operation may be through intrathecal or intracavity administration, as through an Ommaya reservoir, or also by intravascular administration.

Where the therapeutic agents are administered in combination with treatment of brain tumors, one method for administration of the therapeutic compositions of the invention is by deposition into or near the tumor by any suitable technique, such as by direct injection (aided by stereotaxic positioning of an injection syringe, if necessary) or by placing the tip of an Ommaya reservoir into a cavity, or cyst, for administration. Alternatively, a convection-enhanced delivery catheter may be implanted directly into the tumor mass, into a natural or surgically created cyst, or into the normal brain mass. Such convection-enhanced pharmaceutical composition delivery devices greatly improve the diffusion of the composition throughout the brain mass. The implanted catheters of these delivery devices utilize highflow microinfusion (with flow rates in the range of about 0.5 to 15.0 µl/minute), rather than diffusive flow, to deliver the therapeutic composition to the brain and/or tumor mass. Such devices are described in U.S. Pat. No. 5,720,720, incorporated fully herein by reference.

The effective amount of a therapeutic composition to be given to a particular patient will depend on a variety of factors, several of which will be different from patient to patient. A competent clinician will be able to determine an effective amount of a therapeutic agent to administer to a patient to prevent or decrease ongoing neuroinflammation. Dosage of the agent will depend on the treatment, route of administration, the nature of the therapeutics, sensitivity of the patient to the therapeutics, etc. Utilizing $LD_{50}$ animal data, and other information, a clinician can determine the maximum safe dose for an individual, depending on the route of administration. Utilizing ordinary skill, the competent clinician will be able to optimize the dosage of a particular therapeutic composition in the course of routine clinical trials. The compositions can be administered to the subject in a series of more than one administration. For therapeutic compositions, regular periodic administration will sometimes be required, or may be desirable. Therapeutic regimens will vary with the agent, e.g. an NSAID such as indomethacin may be taken for extended periods of time on a daily or semi-daily basis, while more selective agents, such as antagonists of MCP-1, may be administered for more defined time courses, e.g. one, two three or more days, one or more weeks, one or more months, etc., taken daily, semi-daily, semiweekly, weekly, etc.

Formulations may be optimized for retention and stabilization in the brain. When the agent is administered into the cranial compartment, it is desirable for the agent to be retained in the compartment, and not to diffuse or otherwise cross the blood brain barrier. Stabilization techniques include cross-linking, multimerizing, or linking to groups such as polyethylene glycol, polyacrylamide, neutral protein carriers, etc. in order to achieve an increase in molecular weight.

Other strategies for increasing retention include the entrapment of the agent in a biodegradable or bioerodible implant. The rate of release of the therapeutically active agent is controlled by the rate of transport through the polymeric matrix, and the biodegradation of the implant. The transport of drug through the polymer barrier will also be affected by compound solubility, polymer hydrophilicity, extent of polymer crosslinking, expansion of the polymer upon water absorption so as to make the polymer barrier more permeable to the drug, geometry of the implant, and the like. The implants are of dimensions commensurate with the size and shape of the region selected as the site of implantation. Implants may be particles, sheets, patches, plaques, fibers, microcapsules and the like and may be of any size or shape compatible with the selected site of insertion.

The implants may be monolithic, i.e. having the active agent homogenously distributed through the polymeric matrix, or encapsulated, where a reservoir of active agent is encapsulated by the polymeric matrix. The selection of the polymeric composition to be employed will vary with the site of administration, the desired period of treatment, patient tolerance, the nature of the disease to be treated and the like. Characteristics of the polymers will include biodegradability at the site of implantation, compatibility with the agent of interest, ease of encapsulation, a half-life in the physiological environment.

Biodegradable polymeric compositions which may be employed may be organic esters or ethers, which when degraded result in physiologically acceptable degradation products, including the monomers. Anhydrides, amides, orthoesters or the like, by themselves or in combination with other monomers, may find use. The polymers will be condensation polymers. The polymers may be cross-linked or non-cross-linked. Of particular interest are polymers of hydroxy-aliphatic carboxylic acids, either homo- or copolymers, and polysaccharides. Included among the polyesters of interest are polymers of D-lactic acid, L-lactic acid, racemic lactic acid, glycolic acid, polycaprolactone, and combinations thereof. By employing the L-lactate or D-lactate, a slowly biodegrading polymer is achieved, while degradation is substantially enhanced with the racemate. Copolymers of glycolic and lactic acid are of particular interest, where the rate of biodegradation is controlled by the ratio of glycolic to lactic acid. The most rapidly degraded copolymer has roughly equal amounts of glycolic and lactic acid, where either homopolymer is more resistant to degradation. The ratio of glycolic acid to lactic acid will also affect the brittleness of in the implant, where a more flexible implant is desirable for larger geometries. Among the polysaccharides of interest are calcium alginate, and functionalized celluloses, particularly carboxymethylcellulose esters characterized by being water insoluble, a molecular weight of about 5 kD to 500 kD, etc. Biodegradable hydrogels may also be employed in the implants of the subject invention. Hydrogels are typically a copolymer material, characterized by the ability to imbibe a liquid. Exemplary biodegradable hydrogels which may be employed are described in Heller in: Hydrogels in Medicine and Pharmacy, N. A. Peppes ed., Vol. III, CRC Press, Boca Raton, Fla., 1987, pp 137-149.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration.

The methods are also useful in animal models or in vitro models for disease where drugs or therapies aimed at minimizing the negative influence of inflammation on neural stem/progenitor cell function can be discovered or optimized. Additional strategies for which this method may be useful include use for the development of viral vectors or synthetic gene delivery systems where the goals are to modify immune mechanisms and inflammatory effects on stem/progenitor cells. Such models would include genetic manipulation of cells or tissues with the result of minimizing or modifying inflammatory effects on neuroprogenitor/stem cell function.

Models of interest may include, without limitation, the use of animals and cells that have been genetically altered in the expression of pro-inflammatory chemokines and cytokines, e.g. knock-outs and knock-ins of MCP-1; IL-6; TNF-α; etc. In vitro models of interest include cultures and co-cultures in which one or more of astrocytes; microglial cells; neural progenitors; and vascular cells, e.g. endothelial cells, smooth muscle cells, etc.; are present, where the cells may be wildtype or genetically altered as described above. Such cultures find use in determining the effectiveness of candidate therapies and agents in reducing neural inflammation; in the screening of cell-cell interactions, and the like.

An embodiment of interest is the screening of candidate agents for the ability to downregulate or inhibit proinflammatory activity of neural cells. Such compound screening may be performed using an in vitro model, a genetically altered cell or animal, or purified protein corresponding to polypeptides identified herein as involved in the damaging effects of neuroinflammation, e.g. MCP-1; IL-6; TNF-α, etc. Of particular interest are screening assays for agents that have a low toxicity for normal human cells. A wide variety of assays may be used for this purpose.

For example, cell cultures modeling the interaction between neural progenitors and astrocytes may be exposed to inflammatory stimulus, such as LPS; exogenous cytokines, and the like, and the effect on neural progenitors monitored by growth, developmental commitment, expression of markers, phenotype, and the like. The cultures may include other cells, for example microglial cells. Candidate compounds are added to the cell cultures, and the effect in counteracting adverse effects of inflammation determined. As the chemokine MCP-1 is known to mediate certain of these effects, cells deficient, or alternatively constitutively expressing, MCP-1 may find use in such assays, particularly where microglial cells are present. Alternatively, cells, e.g. astrocytes, or cocultures comprising such cells, may be used to analyze compounds for an ability to inhibit expression of MCP-1. As the activation of PPARγ has been shown to ameliorate the effects of neuroinflammation, methods for screening candidate compounds for the capacity to activate PPARγ may likewise find use in the invention. Such methods may include, without limitation, the use of a reporter gene Inked to a PPAR expression vector and a PPAR response element; the use of fusion proteins including one or more PPAR domains and other protein interaction, reporter or coactivator domains; the use of nucleic acid vectors containing PPAR response elements alone or in conjunction with other protein binding elements; and cell lines or animals containing the above. Any methods known to the art of preparing these materials may be useful to the present invention. Agents that activate PPARγ may be further tested in in vitro or in vivo models to determine the effectiveness of the agent on neuroinflammation.

The term "agent" as used herein describes any molecule, e.g. protein or pharmaceutical, with the capability of inhibiting the adverse effects of neuroinflammation. It may not be required that the agent prevent inflammation, so long as the damaging effect on neural progenitors is inhibited.

Candidate agents encompass numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof. Generally a plurality of assay mixtures are run in parallel with different agent concentrations to obtain a differential response to the various concentrations. Typically one of these concentrations serves as a negative control, i.e. at zero concentration or below the level of detection.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs. Test agents can be obtained from libraries, such as natural product libraries or combinatorial libraries, for example.

Libraries of candidate compounds can also be prepared by rational design. (See generally, Cho et al., *Pac. Symp. Biocompat.* 305-16, 1998); Sun et al., *J. Comput. Aided Mol. Des.* 12:597-604, 1998); each incorporated herein by reference in their entirety). For example, libraries of phosphatase inhibitors can be prepared by syntheses of combinatorial chemical libraries (see generally DeWitt et al., *Proc. Nat. Acad. Sci. USA* 90:6909-13, 1993; International Patent Publication WO 94/08051; Baum, *Chem. & Eng. News,* 72:20-25, 1994; Burbaum et al., *Proc. Nat. Acad. Sci. USA* 92:6027-31, 1995; Baldwin et al., *J. Am. Chem. Soc.* 117:5588-89, 1995; Nestler et al., *J. Org. Chem.* 59:4723-24, 1994; Borehardt et al., *J. Am. Chem. Soc.* 116:373-74, 1994; Ohlmeyer et al., *Proc. Nat. Acad. Sci. USA* 90:10922-26, all of which are incorporated by reference herein in their entirety.)

A "combinatorial library" is a collection of compounds in which the compounds comprising the collection are composed of one or more types of subunits. Methods of making combinatorial libraries are known in the art, and include the following: U.S. Pat. Nos. 5,958,792; 5,807,683; 6,004,617; 6,077,954; which are incorporated by reference herein. The subunits can be selected from natural or unnatural moieties. The compounds of the combinatorial library differ in one or more ways with respect to the number, order, type or types of modifications made to one or more of the subunits comprising the compounds. Alternatively, a combinatorial library may refer to a. collection of "core molecules" which vary as to the number, type or position of R groups they contain and/or the identity of molecules composing the core molecule. The collection of compounds is generated in a systematic way. Any method of systematically generating a collection of compounds differing from each other in one or more of the ways set forth above is a combinatorial library.

A combinatorial library can be synthesized on a solid support from one or more solid phase-bound resin starting materials. The library can contain five (5) or more, preferably ten (10) or more, organic molecules that are different from each other. Each of the different molecules is present in a detectable amount. The actual amounts of each different molecule needed so that its presence can be determined can vary due to the actual procedures used and can change as the technologies for isolation, detection and analysis advance. When the molecules are present in substantially equal molar amounts, an amount of 100 picomoles or more can be detected. Preferred libraries comprise substantially equal molar amounts of each desired reaction product and do not include relatively large or small amounts of any given molecules so that the presence of such molecules dominates or is completely suppressed in any assay.

Combinatorial libraries are generally prepared by derivatizing a starting compound onto a solid-phase support (such as a bead). In general, the solid support has a commercially available resin attached, such as a Rink or Merrifield Resin. After attachment of the starting compound, substituents are attached to the starting compound. Substituents are added to the starting compound, and can be varied by providing a mixture of reactants comprising the substituents. Examples of suitable substituents include, but are not limited to, hydrocarbon substituents, e.g. aliphatic, alicyclic substituents, aromatic, aliphatic and alicyclic-substituted aromatic nuclei, and the like, as well as cyclic substituents; substituted hydrocarbon substituents, that is, those substituents containing non-hydrocarbon radicals which do not alter the predominantly hydrocarbon substituent (e.g., halo (especially chloro and fluoro), alkoxy, mercapto, alkylmercapto, nitro, nitroso, sulfoxy, and the like); and hetero substituents, that is, substituents which, while having predominantly hydrocarbyl character, contain other than carbon atoms. Suitable heteroatoms include, for example, sulfur, oxygen, nitrogen, and such substituents as pyridyl, furanyl, thiophenyl, imidazolyl, and the like. Heteroatoms, and typically no more than one, can be present for each carbon atom in the hydrocarbon-based substituents. Alternatively, there can be no such radicals or heteroatoms in the hydrocarbon-based substituent and, therefore, the substituent can be purely hydrocarbon.

Compounds that are initially identified by any screening methods can be further tested to validate the apparent activity. The basic format of such methods involves administering a lead compound identified during an initial screen to an animal that serves as a model for humans and then determining the effects of preventing cognitive damage resulting from neuroinflammation. The animal models utilized in validation studies generally are mammals. Specific examples of suitable animals include, but are not limited to, primates, mice, and rats.

EXPERIMENTAL

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

Example 1

Cranial radiation therapy causes a progressive decline in cognitive function that is inked to impaired neurogenesis.

Chronic inflammation accompanies radiation injury, indicating that inflammatory processes may contribute to neural stem cell dysfunction. The following data demonstrate that neuroinflammation alone inhibits neurogenesis and that inflammatory blockade with indomethacin, a common nor steroidal anti-inflammatory drug, restores neurogenesis following endotoxin-induced inflammation and augments neurogenesis following cranial irradiation.

To determine the effects of inflammation on adult hippocampal neurogenesis, bacterial lipopolysaccharide (LPS) was injected into adult female rats to induce systemic inflammation. The intraperitoneal administration of LPS causes a peripheral inflammatory cascade that is transduced to the brain via IL-1β from the cerebral vasculature and causes a strong upregulation of central pro-inflammatory cytokine production. Following LPS exposure, rats were treated systemically with bromo-deoxyuridine (BrdU) for 6 days to label proliferating cells within the hippocampus. Animals were then sacrificed on the $7^{th}$ day. The fate of the BrdU-labeled, proliferative cells was analyzed with immuno-fluorescent staining and confocal microscopy.

Using confocal analysis, it was found that peripheral LPS exposure resulted in a 240% increase in the density of activated microglia (CD68/ED1-positive) in the dentate gyrus (FIG. 1A-C, F). In normal animals, few ED1-positive cells are found. The neuroinflammation achieved in the LPS paradigm was accompanied by a failure to recruit proliferation within the perivascular space, as indicated by an increase in the average distance of dividing cells (FIG. 1B, C, H) as well as a 35% decrease in hippocampal neurogenesis (FIG. 1D, E, G), as determined by the proportion of non-microglial BrdU+ proliferative cells that co-express the early neuronal marker doublecortin (Dcx).

Inflammation in the central nervous system is effectively managed using steroidal anti-inflammatory drugs, yet it is clearly demonstrated in rodents that corticosteroids are potent inhibitors of neurogenesis and their use in the context of augmenting neurogenesis would be strongly contra-indicated. To determine if inflammatory effects could be countered pharmacologically, animals were treated concurrently with a single dose of intraperitoneal LPS and daily doses of the non-steroidal anti-inflammatory drug (NSAID) indomethacin (2.5 mg/kg, i.p., twice each day). The effect of peripheral LPS exposure on neurogenesis was completely blocked by systemic treatment with indomethacin while indomethacin alone had no effect on neurogenesis in control animals (FIG. 1G, H).

Neuroinflammation could inhibit neurogenesis by a variety of mechanisms, including stimulation of the HPA axis with subsequent elevation of gluccocorticoids, alterations in the relationships between progenitor cells and cells of the neurovasculature, or direct effects of activated microglia on the precursor cells. To determine the extent to which microglial activation might directly affect neural stem/progenitor cells, microglia were stimulated in vitro with LPS. LPS is a potent activator of microglia and up-regulates the elaboration of pro-inflammatory cytokines, including IL-6 and TNF-α. LPS-stimulated or resting microglia were then co-cultured with normal neural stem cells from the hippocampus under conditions that typically stimulate the differentiation of 30 to 40% of the progenitor cells into immature Dcx-expressing neurons (normalized to a value of 1 in FIG. 2A, control). Neurogenesis in the presence of microglia was assessed as the increase or decrease in Dcx-expressing cells relative to control. Co-culture with activated, but not resting, microglia decreased in vitro neurogenesis to approximately half of control levels (FIG. 2A). LPS added directly to precursor cells had no effect on neurogenesis.

To determine if this effect was due to soluble factors or due to cell-cell contact, hippocampal precursor cells were differentiated in the presence of media pre-conditioned by resting or activated microglia. A similar decrease in neurogenesis was found when precursor cells were exposed to the conditioned medium (CM) from activated microglia (FIG. 2A, C), indicating that activated microglia produce soluble anti-neurogenic factors.

Figure 5:
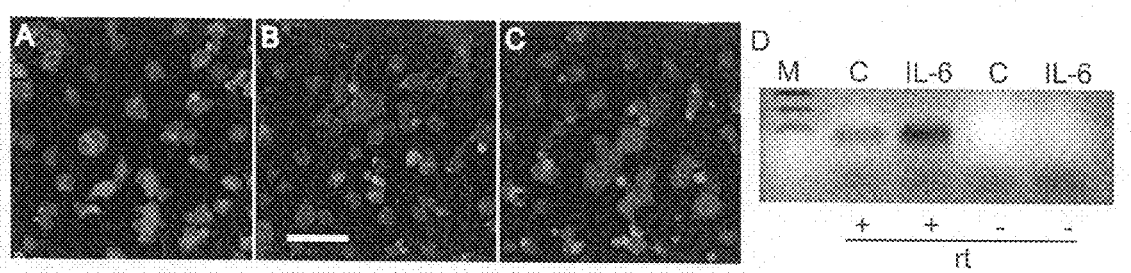
FIGS. 5A-5D Dcx staining and pyknotic TUNEL positive nuclei in treated NPC cultures. NPC cultures were allowed to differentiate normally (A) or in the presence of IL-6 (B) or microglial conditioned medium (C). Treatment with either IL-6 or CM results in decreased Dcx staining (blue) and increased incidence of TUNEL-positive nuclei or nuclear fragments (green), many of which are also immunoreactive for Dcx. Scale bar, 20 µm. D. Total RNA was collected from control cultures ("C")or cultures treated with IL-6 (IL-6) and evaluated for the presence of IL-6 receptor transcripts by RT-PCR+/−reverse transcriptase (rt). The 67 bp PCR product is easily detectable in control cultures and appears to be unregulated following IL-6 treatment. 100 bp ladder (M).

Activated microglia produce the potent pro-inflammatory cytokines interleukin-1β (IL-1β), tumor necrosis factor-α (TNF-α), interferon-γ (INF-γ) and interleukin-6 (IL-6). Progenitor cells were allowed to differentiate in the presence of each cytokine and the relative expression of Dcx was scored after 60 hours. Exposure to recombinant IL-6 (50 ng/ml) (FIG. 2A, D, E) or to TNF-α (20 ng/ml) decreased in vitro neurogenesis by approximately 50% while the effects of IL-1β or INF-γ were not significant. Addition of neutralizing anti-IL-6 antibody to CM from activated microglia was able to fully restore in vitro neurogenesis (FIG. 2A). This implicated IL-6 as a key inhibitor of neurogenesis in microglial CM. Although recombinant TNFα also suppressed neurogenesis, IL-6 blockade alone appeared sufficient to restore neurogenesis in the presence of microglial CM. In contrast to neurogenesis, gliogenesis was unaffected by IL-6 exposure as indicated by the lack of change in the number of cells expressing the astrocyte (glial fibrillary acidic protein, GFAP) or early oligodendrocyte (NG2) markers relative to control cultures (FIG. 2E). The hippocampal precursors used in this study do express the IL-6 receptor, as confirmed by RT-PCR (FIG. 5).

TUNEL labeling was used to determine the potential effects of microglial CM or IL-6 on cell death. Microglial CM and IL-6 significantly increased the fraction of TUNEL-positive apoptotic cells in each differentiating culture (Control, 0.013+/−0.007; CM, 0.092+/−0.023; IL-6, 0.068+/−0.005, mean+/−s.e.m., n≧3). Although this increase was substantial, there was no increase in the relative apoptotic index within doublecortin positive vs. negative cells indicating that cell death was unlikely to select specifically against newborn neurons in vitro (FIG. 2F). The fraction of TUNEL-positive cells that co-labeled with doublecortin was 0.92+/−0.11 for controls (almost all TUNEL-positive profiles are also immunoreactive for Dcx), 0.89+/−0.07 of TUNEL profiles were Dcx positive in cultures treated with microglial CM and 0.83+/−0.02 (mean+/−sem) in cultures treated with IL-6 (see also supplemental FIG. 1).

Mitotic index (fraction of cells labeled with BrdU in 24 hours) in stem cell cultures was unaffected either by CM from stimulated microglia or by IL-6 (92+/−2.8% in controls vs. 95+/−0.7% in CM or 95+/−1.7% in IL-6 treated cultures). When the subset of spontaneously forming immature neurons was independently evaluated, there was a subtle but non-significant trend to reduced BrdU labeling within the neuronal progeny (88+/−7.6% in controls vs. 82+/−1.6% in IL-6 treated cultures). Thus, the effect of IL-6 on in vitro neurogenesis appears to induce both a non-specific decrease in cell survival as well as decreased accumulation of neurons, most likely due to reduced neuronal differentiation rather than selective changes in the proliferation or death of neuroblasts or immature neurons. These findings, taken together with the effect of IL-6 over-expression in transgenic mice, implicate IL-6 as a regulator of hippocampal neurogenesis in neuroinflammation.

Signaling via gp130, the co-receptor of the IL-6 receptor, stimulates the Notch1 pathway, resulting in an increase in expression of the mammalian homolog of hairy-enhancer-of-split, Hes 1, transcription factor and antagonist of pro-neural basic helix-loop-helix (bHLH) genes and hippocampal neurogenesis during development. To determine if IL-6 treatment of adult stem cells leads to an increase in Hes 1 consistent with the reduction in neuronal cell fate, "real-time" quantitative RT-PCR was performed on total RNA extracted from neural precursors exposed for 60 hours to activated microglial CM or IL-6. Both CM and IL-6 caused a dramatic increase in Hes1 mRNA expression (3.2- and 7.7-fold increase respectively, relative to control).

Having demonstrated that neuroinflammation alone is sufficient to inhibit neurogenesis, the irradiation model was then used to determine the relative role of inflammation in this irradiation-induced deficit. Adult rats were treated with indomethacin beginning 2 days prior to 10 Gy cranial X-irradiation and continuing daily for 2 months thereafter. Because rats are more radio resistant than humans, 10 Gy approximates a clinically relevant dose and is below the threshold to cause demyelination or overt vasculopathy in rats. This dose of X-irradiation was previously shown to spare roughly 30% of the NPC proliferative activity but completely ablate the production of neurons. X-irradiation was limited to a 1.5 cm cylinder centered over the cranium (remaining body parts were shielded). One month later, BrdU was administered systemically and at 2 months post-irradiation, brain tissues were analyzed for hippocampal neurogenesis.

Figure 3:
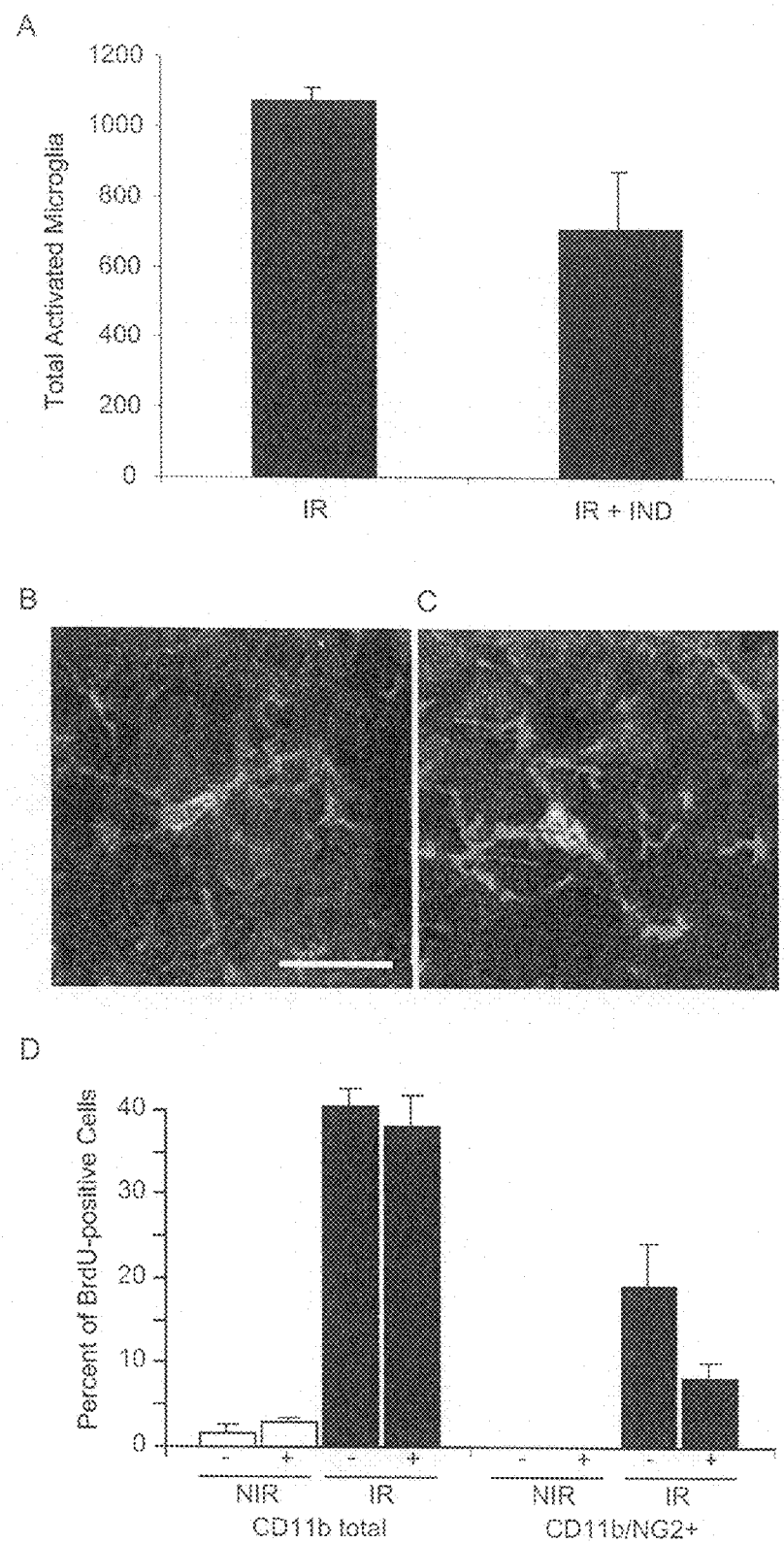
FIGS. 3A-3D Indomethacin decreases microglial inflammation following irradiation. Microglial proliferation and activation in non-irradiated (NIR) and irradiated (IR) hippocampi. Indomethacin (Ind, +/−2.5 mg/Kg) administered orally every 12 hours beginning the day before and for 2 months after irradiation. All groups received BrdU once a day for 6 days starting 4 weeks after irradiation. Animals were killed 2 months after irradiation). (A) Unbiased stereologic quantification of ED1-positive activated microglia per dentate gyrus demonstrates that indomethacin reduces the total number of activated (ED1-positive) microglia per dentate gyrus by roughly 35% (n=4 animals per group; Student's t test; $P<0.05$). (B,C) Examples of BrdU-labeled (red) microglia (CD11b, green) that are either negative (B) or positive for NG2 (blue, C). The NG2 epitope is known to be expressed by peripheral monocytes that are recruited into the brain during inflammation. Scale bar, 25 µm. (D) Quantification of microglia and invading peripheral monocytes in irradiated or non-irradiated animals concurrently treated with indomethacin (+/−). Irradiation caused a dramatic increase in proliferating microglia (CD11b/BrdU-double positive cells) in the granule cell layer and subgranule zone of irradiated animals relative to non-irradiated controls (n=4 animals per group; Student's t test; $P<0.000001$). Indomethacin had little effect on the relative fraction of BrdU-labeled cells that were microglia following radiation but significantly reduced the activation state (A) and the relative number of cells that were recruited from the periphery (NG2-positive/CD11b positive monocytes, $P<0.05$, Student's T test, n=4).
Figure 6:
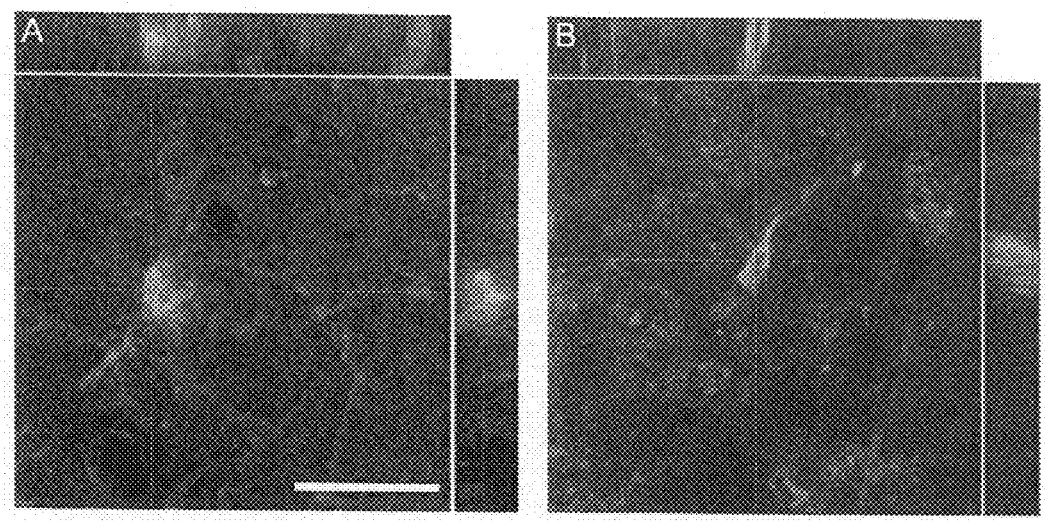
FIGS. 6A-6B Orthogonal projections of NG2-associated microglia in the irradiated brain. Microglia in irradiated or LPS treated animals frequently co-localize with NG2 proteoglycan. It is thought that NG2-positive, CDIIb-positive cells are peripheral monocytes recruited to the brain following injury. However, microglia are also known to promote myelination and colocalization of NG2 with CD11b can also occur when oligodendrocytes envelope activated microglia. Shown are two examples of NG2 co-localized with CD11b staining. In A, the NG2 staining (blue) is associated with the CD11b-positive microglial cell (green, BrdU in red) but appears to originate from neighboring oligodendrocyte processes. In B, the NG2 staining and CD11b staining tightly co-localize to the cytoplasm and membrane of an individual microglial cell. Quantification of NG2-positive microglia in FIG. 3D excluded microglia where NG2 immunoreactivity was clearly associated with an enveloping oligodendrocyte process. Scale bar, 20 µm.

Irradiation causes a striking inflammatory response characterized by the persistence of activated microglia (FIG. 3A-C) relative to the minimal levels in normal control animals. Unbiased stereologic quantification of CD68 (ED1)-positive activated microglia in irradiated animals revealed that indomethacin treatment caused a 35% decrease in activated microglia per dentate gyrus (FIG. 3A). Many of these microglia were proliferative and a large fraction of all dividing cells within the dentate gyrus were labeled for the monocyte/microglia marker CD11b, which labels both activated and resting microglia (FIG. 3D). A subpopulation of CD11b+ microglia co-expressed the marker NG2 (FIG. 3C, D and FIG. 6), which represents peripheral blood monocytes/microglia that contribute to chronic neuroinflammatory lesions within the brain. Indomethacin was particularly effective at decreasing this CD11b/NG2+ subpopulation of infiltrating, proliferating peripheral monocytes following irradiation (FIG. 3D), indicating an indomethacin-induced change in chemokine and/or integrin signaling that recruits trans-endothelial migration of immune cells following injury.

If inflammation were the primary cause of the lack of neurogenic signaling within the dentate subgranule zone, then inflammatory blockade would be expected to restore neurogenesis.

Confocal microscopy was used to analyze the proportion of proliferative (BrdU+) cells that co-express markers (FIG. 4A) for mature neurons (NeuN) (FIG. 4B), immature neurons (type III beta tubulin) (FIG. 4C), astrocytes (GFAP) (FIG. 4D) and immature oligodendrocytes (NG2+/CD11b−) (FIG. 4E). Indomethacin treatment in non-irradiated rats had no effect on cell fate relative to untreated, non-irradiated controls. Irradiation decreased the proportion of proliferative cells adopting a neuronal fate (FIG. 4A). Indomethacin treatment during and after irradiation exposure partially restored the relative proportion of proliferative cells adopting a neuronal fate relative to untreated, irradiated animals (37% vs. 15%, respectively; FIG. 4A-C).

Unbiased stereological quantification of total BrdU+ proliferative cells per neurogenic region (granule cell layer+ subgranule zone) of the dentate gyrus revealed no significant difference in overall proliferation between indomethacin-treated and untreated irradiated animals (958±136 proliferative cells vs. 828±135 proliferative cells, respectively; control animals exhibited 1938±429 proliferative cells per neurogenic region). Correcting the fraction of proliferative cells adopting a neuronal fate for the total number of proliferative cells yields a significant increase in total newborn hippocampal neurons in indomethacin-treated, irradiated animals compared with untreated, irradiated animals (360±68 newborn neurons vs. 125±25 newborn neurons, respectively; FIG. 4F). This is a substantial increase in neurogenesis but still only 20% to 25% of the neurogenesis observed in naïve animals (~1600 newborn neurons).

To describe further the relationship between microglial inflammation and neurogenesis, neurogenesis was plotted against activated microglial load for each irradiated animal (FIG. 4G). Neurogenesis and inflammation show a striking negative correlation (R=−0.93 for activated microglial loads above 1000 per dentate gyrus; activated microglial load was ~500 in controls.) indicating that the extent of inflammation has a direct titrating role on neurogenesis within the adult dentate gyrus.

The present data indicate that inflammation itself can suppress neurogenesis and that chronic inflammation following radiation treatment contributes to the neural stem cell dysfunction that is linked to a progressive decline in learning and memory. Chronic microglial activation and peripheral monocyte recruitment with the accompanying increase in local pro-inflammatory cytokine production, including IL-6, emerge as potent anti-neurogenic components of brain injury. Both IL-6 and the IL-6 receptor/gp130 complex are expressed in the postnatal hippocampus, and hippocampal expression of the IL-6 receptor increases following systemic challenge with LPS. The IL-6 family of cytokines, including ciliary neurotrophic factor (CNTF) and leukemia inhibitory factor (LIF), belong to a category of signaling molecules termed "neurokines". IL-6, like CNTF, promotes both astrogliogenesis and oligodendrogliogenesis, and it may be that IL-6 plays a role in inflammatory inhibition of neurogenesis by diverting stem cells into a glial program at the expense of neurogenesis. Gliogenesis is relatively well preserved in the irradiated microenvironment (FIG. 4A) and the in vitro data indicates that IL-6 inhibition of neurogenesis is primarily due to a blockade in neuronal differentiation rather than selective influences on cell death or proliferative activity.

Figure 7:
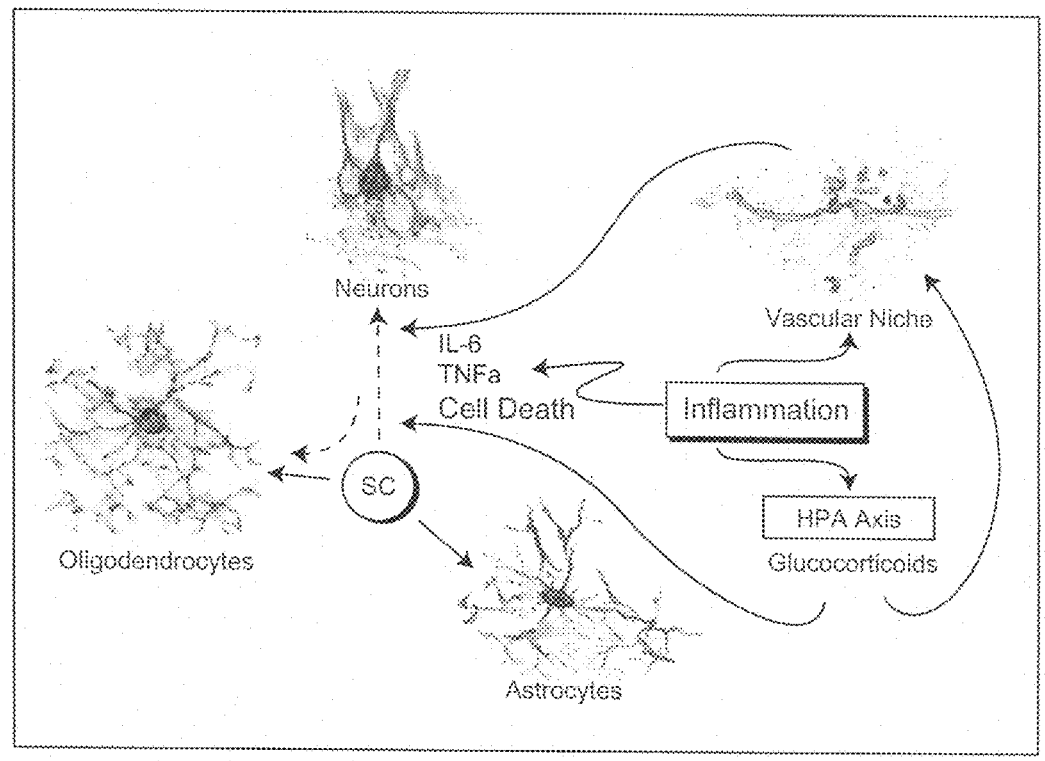
FIG. 7 Inflammation may inhibit neurogenesis by multiple mechanisms. Neural stem cells (SC) can differentiate into neurons, oligodendrocytes or astrocytes. Inflammation may disrupt neuronal differentiation by directly inhibiting neuronal fate choice and differentiation resulting in a diversion of cell fate into glial lineages (dashed arrows). This may be via gp130 mediated activation of Notch pathway genes, or indirectly by altering the interaction of neural progenitor cells with other cells of the local microenvironment such as cells of the vasculature within the subgranule zone (see FIG. 1B, C, H). The radiation-induced peripheral monocyte recruitment and its inhibition with indomethacin provide clear evidence that endothelial cell status is significantly modulated in inflammation and inflammatory blockade. Finally, inflammation is known to modulate the hypothalamic-pituitary-adrenal axis and a concurrent elevation in circulating glucocorticoid levels would feed back into the neurogenic regulatory mechanisms to suppress hippocampal neurogenesis.

Inflammatory blockade with indomethacin decreased microglial activation and this may account for part of the restorative effect of indomethacin treatment on neurogenesis following irradiation. However, inflammatory blockade is accompanied by a broad spectrum of effects that could influence neurogeneis in several ways (FIG. 7). Restoration of neurogenesis with inflammatory blockade may involve a reduction in newborn cell death, and/or by attenuation of HPA axis activation. The subsequent decrease in pro-inflammatory cytokines and cognate decrease in serum glucocorticoid levels may contribute to restored neurogenesis. In addition, the microvasculature of the hippocampus is strongly implicated as a critical element of the neurogenic microenvironment and both endotoxin and irradiation-induced inflammation disrupts the association of proliferating progenitor cells with micro-vessels. The recruitment of circulating inflammatory cells is highly dependent on the endothelial status and elaboration of chemokines. One of the most robust effects of indomethacin in the present paradigm is the reduction in peripheral monocyte recruitment indicating that the inflammatory status of endothelial cells (e.g., expression of chemokines and/or ICAM) may be normalized by indomethacin. Indeed, one known attribute of indomethacin treatment is the normalization of vascular permeability, which likely affects the neurogenic vascular microenvironment. Although IL-6 plays an important role, a narrow focus on IL-6 alone ignores the complexity of signaling that is altered in neuroinflammation and future experiments should address the more complex interactions of HPA axis, invading inflammatory cells, and alterations in the vascular niche of the hippocampal dentate gyrus.

Neuroinflammation and microglial pathology are associated with many diseases of cognition in which memory loss features prominently, such as Alzheimer's Disease, Lewy Body Dementia, and AIDS Dementia Complex. Further, serum IL-6 levels in humans correlate with poor cognitive performance and predict risk of dementia. Clinical treatment with indomethacin and other NSAIDs ameliorates the risk and/or progression of memory loss. Our findings may shed some light on the potential contribution of inflammation-induced neurogenic blockade to memory pathology and on the mechanism of the beneficial effects of NSAID treatment in certain dementias.

Microglial cytokines also increase cell death and one action of inflammatory blockade may simply be rescue of newborn neurons that have been endangered by the inflammatory environment. Neurogenesis induced by hippocampal seizure activity is accompanied by a striking increase in the apoptosis of newborn neurons. Inflammation accompanies the seizure activity and cell death can be attenuated, in part, by treatment with an alternative anti-inflammatory drug, minocycline.

Decreasing microglial activation accounts for at least part of the restorative effect of indomethacin treatment on neurogenesis following irradiation. However, inflammatory blockade is accompanied by a broad spectrum of effects that could influence neurogeneis in several ways. Restoration of neurogenesis with inflammatory blockade may involve attenuation of HPA axis activation. The subsequent decrease in pro-inflammatory cytokines and cognate decrease in serum glucocorticoids may contribute to restored neurogenesis. In addition, the microvasculature of the hippocampus is strongly implicated as a critical element of the neurogenic microenvironment and both endotoxin and irradiation-induced inflammation disrupts the association of proliferating progenitor cells with micro-vessels. The recruitment of circulating inflammatory cells is highly dependent on the endothelial status and elaboration of chemokines. One of the most robust effects of indomethacin in the present paradigm is the reduction in peripheral monocyte recruitment indicating that endothelial cell expression of chemokines and/or ICAM elaboration may be normalized by indomethacin. Indeed, one known attribute of indomethacin treatment is the normalization of vascular permeability, which likely has an impact on the neurogenic microenvironment.

Methods

Cell Culture:

Progenitor Cell Culture Adult hippocampus-derived neural precursor cells were isolated from adult rat hippocampus and cultured as previously described. Briefly, adult female Fisher-344 rats were deeply anesthetized with sodium pentobarbital and were dissected immediately. Hippocampi were enzymatically dissociated with papain (2.5 U/ml; Worthington, Freehold, N.J.)-dispase II (1 U/ml; Boehringer Mannheim, Indianapolis, Ind.)-DNase I (250 U/ml, Worthington) solution. Digested tissue was then washed with DMEM-10% fetal calf serum (FCS) and subsequently mixed with PBS-equilibrated Percoll solution to a final concentration of 35% Percoll. The Percoll solution was made by mixing nine parts of Percoll (Amersham Pharmacia Biotech, Uppsala, Sweden) with one part of 10× PBS. The cell suspension was then fractionated by centrifugation for 10 min at 1000×gravity. Floating myelin and tissue debris were discarded and the cell pellet re-suspended in 65% Percoll solution and fractionated again by centrifugation for 10 min at 1000×g. The floating neural precursors were collected, washed free of Percoll, and plated onto poly-L-ornithine/laminin-coated dishes in DMEM/F12 (1:1) containing 10% FCS medium for 24 hrs; then medium was replaced with serum-free growth medium consisting of DMEM/F12 (1:1) supplemented with N2 supplement (Life Technologies, Gaithersburg, Md.) and 20 ng/ml of human recombinant FGF-2 (Peprotech, Rocky Hill, N.J.). Cell lines were labeled via infection with replication deficient GFP-expressing recombinant retrovirus LZRS-CAMut4GFP. GFP-labeled cells were propagated in DMEM/F12 with 20 ng/ml bFGF, penicillin/streptomycin/amphotericin B (Life Technologies), and N2 supplement (Life Technologies). Plastic tissue culture dishes were coated with 10 mg/ml polyornithine in dH20 overnight under UV illumination, rinsed 2× with dH20, recoated with 5 mg/ml mouse laminin (Life Technologies), incubated overnight at 37° C., and frozen for long-term storage at −80° C. Cells were fed every 2-3 days by 75% solution exchange and split 1:4 every 6-7 days after brief trypsinization and centrifugation. Freezing was in DMEM/F12/10% DMSO/BIT supplement (Stem Cell Technologies), and thawing from storage was in DMEM/F12/BIT.

Microglia Culture BV-2 microglial cells were plated on uncoated plastic tissue culture plate and grown in DMEM:F12 (1:1) media with BIT supplement (Stem Cell Technologies).

Co-culture and production of conditioned media BV-2 murine microglia were stimulated with LPS (1 μg/ml, Sigma, St. Louis Mo.) for 12 hours. Control cultures were mock-stimulated with an equal volume of PBS. Cultures were then treated with trypsin, extensively washed and then re-plated with an equal number of GFP-positive hippocampal stem/progenitor cells on laminin-coated dishes (no LPS was present in the co-culture). Co-culture was done in differentiation media, DMEM:F12 (1:1) with BIT supplement, 1% fetal bovine serum, 100 nM all trans-retinoic acid, 2 ng/ml FGF-2 and 10 ng/ml NT3 for 60 hours. To prepare conditioned media from stimulated and non-stimulated microglia, microglia were treated with LPS or PBS (unstimulated controls) for 24 hours and then washed to remove LPS from stimulated cultures. Fresh differentiation medium was then incubated with the microglia overnight and then removed, sterile filtered and diluted with fresh differentiation media (1:1) prior to adding to neural stem/progenitor cell cultures. In a modified version of this experiment, a neutralizing anti-IL-6 antibody (1 ug/ml final concentration in culture medium, R&D systems, Minneapolis, Minn.) was added to the conditioned media from microglia. After 60 hrs, co-cultured or conditioned-media-treated stem/progenitor cells were fixed with 4% buffered paraformaldehyde and immunostained for doublecortin using goat anti-doublecortin (Dcx) (1:500, Santa Cruz Biotechnology, Santa Cruz, Calif.). DAPI was used to identify cell nuclei. Fluorescent photomicrographs were taken at systematically sampled positions within each well and changes in doublecortin expression relative to control cultures scored by unbiased quantification of the average signal intensity in positive cells (i.e., fluorescence intensity above a background threshold of Dcx fluorescence measured in undifferentated cells using Photoshop).

Recombinant cytokines Recombinant rat cytokines (R&D Systems, Minneapolis, Minn.), interleukin 1β (6-50 ng/ml), tumor necrosis factor α (2-20 ng/ml), interferon γ (1-5 ng/ml) and interleukin-6 (6-50 ng/ml) were added to hippocampal precursor cells cultured on laminin-coated plates in differentiation media, DMEM:F12 (1:1) with BIT supplement, 1% fetal bovine serum, 100 nM all trans-retinoic acid, 2 ng/ml FGF-2 and 10 ng/ml NT3 for 60 hours. Cells were immunostained for doublecortin, type III β-tubulin, GFAP, or NG2 and analyzed as above.

Proliferation and survival assays BrdU was added to the culture media from hour 24 to hour 48 of the 60 hour paradigm. Immunocytochemistry and confocal microscopy was then used to determine the fraction of GFP+ cells that labeled with BrdU, TUNEL, or type III β-tubulin or doublecortin. TUNEL staining was performed with Apoptag Red (Serologicals, Norcross, Ga.). The fraction of total (DAPI+) nuclei that were TUNEL+ were determined, as well as the fraction of doublecortin positive cells that were also TUNEL+.

Total RNA isolation, cDNA synthesis, and SYBR Green real-time quantitative RT-PCR. Total RNA was isolated from neural precursor cell cultures using RNeasy mini kit (Qiagen) and synthesis of cDNA was performed using the SuperScript First-strand Synthesis System for RT-PCR (Invitrogen). Quantitative SYBR Green real time PCR was carried out as described previously. Briefly, each 25 μl SYBR green reaction consisted of 5 μl of cDNA (50 ng/μl), 12.5 μl of 2× Universal SYBR Green PCR Master Mix (PerkinElmer Life Sciences) and 3.75 μl of 50 nM forward and reverse primers. Optimization was performed for each gene-specific primer prior to the experiment to confirm that 50 nM primer concentrations did not produce nonspecific primer-dimer amplification signal in no-template control tubes. Primer sequences were designed using Primer Express Software. Quantitative RT-PCR was performed on ABI 5700 PCR instrument (PerkinElmer Life Sciences) by using 3-stage program parameters provided by the manufacturer as follows; 2 min at 50° C., 10 min at 95° C., and then 40 cycles of 15 s at 95° C. and 1 min at 60° C. Specificity of the produced amplification product was confirmed by examination of dissociation reaction plots. A distinct single peak indicated that single DNA sequence was amplified during PCR. In addition, end reaction products were visualized on ethidium bromide-stained 1.4% agarose gels. Appearance of a single band of the correct molecular size confirmed specificity of the PCR. Each sample was tested in five copies with quantitative PCR, and samples obtained from three independent experiments were used to calculate the means and standard deviations. Primers were as follows (F=forward, R=reverse):

| GAPDH F | AAGAGAGAGGCCCTCAGTTGCT | (SEQ ID NO: 1) |
|---------|------------------------|----------------|
| GAPDH R | TTGTGAGGGAGATGCTCAGTGT | (SEQ ID NO: 2) |
| MASH1 F | GACAGGCCCTACTGGGAATG | (SEQ ID NO: 3) |
| MASH1 R | CGTTGTCAAGAAACACTGAAGACA | (SEQ ID NO: 4) |
| HES1 F | CGGCTTCAGCGAGTGCAT | (SEQ ID NO: 5) |
| HES1 R | CGGTGTTAACGCCCTCACA | (SEQ ID NO: 6) |
| HES5 F | GGAGGCGGTGCAGTTCCT | (SEQ ID NO: 7) |
| HES5 R | GGAGTGGTAAAGCAGCTTCATC | (SEQ ID NO: 8) |
| NEUROD F | GGACAGACGAGTGCCTCAGTTC | (SEQ ID NO: 9) |
| NEUROD R | TCATGGCTTCAAGCTCATCCTCCT | (SEQ ID NO: 10) |

Indomethacin administration. The non-streroidal anti-inflammatory drug indomethacin was selected as an anti-inflammatory agent for its potency, ability to penetrate the blood-brain-barrier (BBB), demonstrated efficacy in decreasing microglial inflammation in vitro and in vivo, and particular ability to decrease monocyte/microglial migration and elaboration of pro-inflammatory cytokines. Indomethacin inhibits cyclo-oxygenase (COX; type1>2), thereby decreasing production of the prostaglandin arachadonic acid metabolites that broadly contribute to microglial recruitment and activation. Additionally, indomethacin agonizes the transcription factor peroxisome proliferator-activator-γ (PPAR-γ) that inhibits the elaboration of pro-inflammatory cytokines in monocytes/microglia.

Adult female Fisher 344 rats (160-180 grams) were given indomethacin (Sigma, St Louis, Mo.) 2.5 mg/Kg, administered either i.p. (in 5% bicarbonate) or mixed into soft dog food (Pedigree, Kal Kan foods, Inc, Vernon, Calif.) every 12 hours for either 1 week (i.p administration paradigm) or two months (dog food paradigm), beginning the day before LPS exposure or irradiation and ending on the day of sacrifice. Control animals were given either vehicle (5% bicarbonate) injections i.p. or plain dog food. To ensure complete consumption of food and medication in the 2 month paradigm, rats were restricted to 80% of their ad lib intake. Rats continued to gain weight and exhibited normal grooming behavior throughout the two-month experiment. Serum indomethacin levels achieved with this paradigm ranged from 2.7 to 3.7 ug/ml (the human therapeutic index is 1.0 to 2.0 ug/ml).

LPS exposure. Bacterial lipopolysaccharide (LPS, Sigma, St Louis, Mo.) was administered in sterile saline by intraperitoneal injection at a dose of 1 mg/Kg one time. This caused mild sickness behavior (decreased grooming, decreased locomotor activity, increased piloerection) for approximately 2 days, resolving by the $3^{rd}$ day. The dose of LPS chosen causes mild sickness behavior in rats that resolves within 1-2 days; the dose of LPS used to induce endotoxic shock is 10-fold higher than that used in the present study.

Irradiation Adult female Fisher 344 rats were anesthetized with ketamine and xylazine and exposed to cranial irradiation using a Philips orthovoltage X-ray system operated at 200 kVp and 20 mA. A single dose of 10 Gy was delivered to the cranium of each rat with shielding of the body, neck, eyes and snout. Dosimetry was done using TLD dosimeters (K & S Associates, Nashville, Tenn.) buried in the hippocampi, cerebellum, mouth, eyes and ears of euthanized rats. The corrected dose rate was approximately 44.5 cGy/minute. Sham-irradiated controls for all experiments received anesthesia only.

BrdU injections and tissue preparation. Animals were injected intraperitoneally with BrdU once each day for 6 days. Animals were then anesthetized and sacrificed on the $28^{th}$ day after the initial BrdU injection by transcardial perfusion with 4% paraformaldehyde. Brains were removed and postfixed overnight and then equilibrated in phosphate buffered 30% sucrose. Free floating 40 μm sections were collected on a freezing microtome and stored in cryoprotectant as previously described.

Immunocytochemistry and immunofluorescent staining. Free floating sections were immunostained as previously described using the following primary antibodies and working concentrations: mouse anti-NeuN (1:4, gift from R. Mullen); guinea pig-anti GFAP (1:800, Harlan, Indianapolis, Ind.); mouse anti-type III βtubulin (Tuj-1, 1:500, Berkeley Antibody Co., Richmond, Calif.); rabbit anti-NG2 (1:200, Chemicon, Temecula, Calif.); mouse anti-rat CD11b (1:200, Serotec, Oxford, U.K.); mouse anti-ED-1 (1:100, Research Diagnostics Inc., Flanders, N.J.); biotinylated-*Lycopersicon esculentum* (tomato) lectin (1:200, Vector, Burlingame, Calif.).

Confocal microscopy. All confocal microscopy was performed using a Zeiss 510 confocal microscope. Appropriate gain and black level settings were determined on control tissues stained with secondary antibodies alone. Upper and lower thresholds were always set using the range indicator function to minimize data loss through saturation.

Cell counting and unbiased stereology. All counts were limited to the hippocampal granule cell layer proper and a 50 μm border along the hilar margin that included the neurogenic subgranule zone. The proportion of BrdU cells displaying a lineage-specific phenotype was determined by scoring the co-localization of cell phenotype markers with BrdU using confocal microscopy. Split panel and z-axis analysis were used for all counting. All counts were performed using multi-channel configuration with a 40× objective and electronic zoom of 2. When possible, 100 or more BrdU-positive cells were scored for each marker per animal. Each cell was manually examined in its full "z"-dimension and only those cells for which the nucleus was unambiguously associated with the lineage-specific marker were scored as positive. The total number of BrdU-labeled cells per hippocampal granule cell layer and subgranule zone was determined using diaminobenzadine stained tissues. In a separate series, the total number of ED1-labeled cells per dentate gyrus was also determined using diaminobenzadine stained tissue. Stained BrdU-positive nuclei or ED1-positive cells were scored under light microscopy using Microbrightfield Stereo Investigator software and the Fractionator method. Overestimation was corrected using the Abercrombie method for nuclei with empirically determined average diameter of 13 μm within a 40 μm section.

Example 2

Behavioral Aspects of Inflammation-induced Deficits

LPS-induced inflammatory response impairs performance in the Barnes maze. It has been reported previously that irradiation and LPS-induced inflammation impair performance in hippocampus-dependent spatial tasks. The present studies confirm that LPS treatment impaired recall of a goal position learned prior to LPS treatment. The Barnes maze is a 6-foot diameter bright white platform with 8 escape boxes under holes in the rim of the platform. All escape holes are blocked except one and the rat is initially placed in the goal box for familiarization. The rat is then placed in the center of the maze and is allowed to find its way back to the goal box to escape the aversive brightly lit platform. Learning is seen as a decrease in the distance traveled to reach the goal box with consecutive trials on a given day and in repeat sessions on sequential days. One measure of recall is to determine distance traveled when the animal is tested on the same task after a time delay or after experimental treatments.

To determine if there were differences in recall following LPS treatment, animals were trained on the Barnes maze for 5 consecutive days prior to LPS treatment. LPS was given on day 0 and animals tested for recall on day 7. Low-dose intraperitoneal LPS treatment makes animals feel mildly ill and they will reduce their water and food intake for a period of one or two days. There is a temporary weight loss that is fully recovered by day 7. Although all animals showed normal weights and were indistinguishable on independent measures of locomotor activity, there was a significant increase in distance traveled in LPS vs. vehicle groups indicating a measurable LPS effect in this paradigm. This deficit disappeared by two weeks but re-training animals to a new goal box position showed that LPS treatment two weeks prior still impaired the acquisition of a new task. The effects of indomethacin were tested on both acquisition and retention following LPS treatment or irradiation.

To determine if treatment with indomethacin influenced the LPS effects on learning and memory, animals were trained on the Barnes maze for 5 days prior to treatment with a single intraperitoneal injection of LPS. Animals were simultaneously treated with indomethacin twice daily (2.5 mg/kg), either in edible treats or by intraperitoneal injection in aqueous vehicle. Animals were weighed daily and after 7 days tested for memory retention on the Barnes maze. On days 8-11, animals were re-trained for their ability to learn the position of a new goal box in the Barnes maze. Animals were then tested on day 14 for the ability to remember the position of the second goal box. LPS caused a ~14% increase in the distance traveled to the goal box learned prior to LPS treatment, indicating impaired spatial memory. LPS caused a significant increase (~28%) in the distance traveled during day 8 trials used to learn the position of the new goal box (indicating impaired spatial learning) but all animals eventually learned the position of the goal box by day 11 (no difference in distance traveled between LPS and control groups).

Indomethacin treatment by intraperitoneal injection alone (in the absence of LPS) caused animals to perform more poorly in all tasks at all time points indicating a drug-induced impairment in both learning and memory (when administered by IP injection). In contrast, oral indomethacin treatment alone had no measurable effects on learning and memory at any timepoint indicating that oral administration was well tolerated.

Oral administration of indomethacin was able to completely reverse the effects of LPS for both memory retention and in learning the position of the second goal box. This indicates that indomethacin is able to block the effects of LPS that negatively affect learning and memory. This also indicates that intraperitoneal administration of indomethacin (while able to restore neurogenesis as measured in our prior work) is itself not well tolerated and negatively influences rat performance in learning and memory tasks. This is an important observation indicating that IP administration of drugs may cause sufficient stress to mask the behavioral effects being studied.

Morris Water Maze. The Morris water maze is a large 6' diameter pool of water in which a submerged 4" diameter platform is hidden just below the surface of the water. Rats placed into the pool will swim in an attempt to escape and will find the platform accidentally or, after 90 seconds of swimming will be placed on the platform and thereby learn the platform position. Improving recall of the platform position is represented in a shortening of the path the animal takes to reach the platform.

Prior to treatment, adult female rats are given a water maze baseline trial in which they are placed in the pool with no platform for 90 s to habituate to the environment and to measure individual variability in swimming ability (swim speed and swim distance) as well as quadrant biases. Animals are subsequently trained with an additional 4 trials/day over 4 days in which they are given 90 s to locate a platform hidden beneath the water. If unable to locate the platform, the animals are manually placed on the platform and allowed to sit for 20 seconds. Latency, path length and heading angle are the variables that are recorded using an HVS tracking system to establish a baseline measure how well each rat learns the location of the hidden platform as combined, these variables are considered to be valid and reliable measures of hippocampus-dependent learning in water maze tasks. In addition, "search error" (average distance from the platform during the trial) will be analyzed as it is a more sensitive measure of spatial learning than latency, swim path length and heading angle for spatial learning deficits in aged rats. On the 5th day of pre-training, the animals participate in a probe trial in which they are placed in the pool with no platform for 90 seconds to measure the strength of their spatial learning or retention of information about the location of the hidden platform. The fraction of time and fraction of swim path length spent in the platform quadrant indicates better retention of this information.

Animals are then entered in the radiation or LPS paradigms. At the end of the treatment strategies (2 weeks after LPS or 8 weeks after irradiation), the animals are again tested for spatial memory. First, animals are given a probe trial with no platform to measure quadrant swim speed, path length, and perseveration in the pre-test platform quadrant. Then, the animals are tested in using a reversal paradigm where the platform is placed in the opposite quadrant and animals trained as in the pre-test. Difficulty in acquiring the new platform position indicates either impaired acquisition or abnormal preservation (i.e., continued preference to search in the old platform quadrant even when the new platform position is presented to the animals. Differences in acquisition between pre- and post-experiment performances are evaluated for each animal and these differences contrasted between groups. As in the Barnes maze, a group size of 12 is sufficient to detect small changes in retention or acquisition.

The primary goal in these studies is to correlate neurogenesis to either acquisition or retention of a spatial memory. The Barnes maze testing provides a user-friendly paradigm (rats stay dry) and will be our primary analysis tool. The Morris water maze testing is done on subsets of animal groups to validate the Barnes maze data using a separate paradigm. Animals are scored for latency (total time to acquire the hidden platform or goal box), speed, path angle relative to the platform or goal box, and total path distance. In the probe trials (platform removed or goal box hidden), the total time and path distance within each quadrant will be scored. The four trials per day are binned into a daily block (average of 4 trials) and dependent variables (latency, path-length and average path-speed to reach the goal) will be analyzed using repeated-measures ANOVAs with the following conditions: 1. non-irradiated vs. irradiated; 2. irradiated vs. irradiated/indomethacin; 3. non-irradiated vs. irradiated/indomethacin. Identical analysis will be used in LPS paradigms. Similar analysis will be prepared for individual animals to determine the significance of changes observed between training session (days 1, 2, 3, 4) or between pre-experiment and post-experiment data for a given animal. A Newman-Keul strategy will be used for post hoc analysis.

These data demonstrate the effectiveness of anti-inflammatory agents in preventing cognitive defects associated with neuroinflammation. The effectiveness of the methods on the treatment of human subjects is similarly evaluated, through learning and memory tasks, and may be further evaluated using functional criteria known in the art, for example through the use of fMRI.

Example 3

The Chemokine Monocyte Chemoattractant Protein-1 (MCP-1) is Necessary for Irradiation-induced Inhibition of Neurogenesis Neuroinflammation inhibits adult hippocampal neurogenesis through both a specific block in neuronal differentiation and a generalized decrease in newborn cell survival. As shown above, anti-inflammatory therapy with the NSAID indomethacin restores neurogenesis following cranial radiation exposure. Because one of the most robust effects of indomethacin treatment was to decrease the number of infiltrating blood monocytes, the population of recruited monocytes/macrophage may be an important component of the neuroinflammatory response to irradiation, and recruited monocytes/macrophages may play a pivotal role in inflammatory inhibition of neurogenesis.

Monocyte chemoattractant protein-1 (MCP-1) is a CC family chemokine (i.e., chemoattractant cytokine), Rollins (1997) Blood 90, 909-928, that is produced by astrocytes and microglia in response to injury or inflammatory cytokines. MCP-1 is necessary for monocyte recruitment to sites of inflammation. The MCP-1 receptor, CCR2, is expressed by many cell types in the brain including monocytes, neural progenitor cells, smooth muscle and endothelial cells (see Banisadr et al. (2002) J. Neurochem. 81, 257-269).

Loss of MCP-1 function in mice may lead to a less severe defect in neurogenesis following irradiation. This may occur by reducing peripheral monocyte recruitment and/or by reducing the inflammation-induced changes to the stem cell's vascular microenvironment or via MCP-1 action on the precursor itself. The following data address this question, and demonstrate the important role of MCP-1 in mediating the adverse effects of neuroinflammation.

Methods

Adult mice were treated with 10 Gyx-irradiation limited to a 1 cm column centered over the cranium and allowed to recover for one month. The MCP–/– mice are as described by Lu et al. (1998) J. Exp. Med. 187:601-608; and the control wild-type mice are otherwise genetically matched to the knockout mice. 50 mg/kg BrdU was then administered daily for 6 days and animals allowed to survive for an additional 3 weeks. Brains were evaluated for neurogenesis 2 months after irradiation (one month after the initial BrdU injection). Neurogenesis was measured as surviving, BrdU-positive neurons in the dentate gyrus of the hippocampus.

Proliferative cell fate was determined using immunofluorescent-staining and confocal microscopy. The percent of BrdU-labeled cells that adopt a neuronal cell fate (NeuN plus Doublecortin) is shown in FIG. 8B. The total number of newborn neurons was also estimated by correcting the proportion of BrdU-labeled neurons for total number of BrdU-positive cells per hippocampal dentate gyrus (FIG. 8C).

Results

Both MCP-1–/– and wild type animals had a similar density of microglia in the hippocampus, demonstrating that MCP-1 is not necessary for developmental colonization of brain with microglial cells.

However, in the MCP-1–/– mice, the monocyte/microglia response after irradiation was attenuated relative to the wild type mice. Total microglial (Iba1+) cell density was reduced; and cell bodies were smaller, indicating decreased activation. Staining with a reagent specific for activated microglia (CD68+) showed a lowered density; and the staining intensity was reduced, indicating impaired microglial activation in MCP-1 null animals.

In normal adult rats, irradiation causes a 70% decrease in the number of newborn cells that accumulate in the hippocampus, although the number of progenitor cells that can be isolated from the irradiated hippocampus is not significantly different from that of a non-irradiated animal. This indicates a defect in either proliferation and/or survival of progenitor progeny after irradiation. MCP-1 could contribute to this defect by altering the precursor cells' local microenvironment, i.e., either by altering the vascular and astrocytic microenvironment of the precursor cells in the hippocampal subgranular zone and/or altering subsequent extravasation of monocytes into this vascular niche.

To determine if absence of MCP-1 influenced the severity of irradiation-induced precursor dysfunction in mice, the accumulation of BrdU-positive cells was evaluated in MCP-1 null animals vs. wild type controls. Using unbiased stereological quantification of total BrdU+ cells in the neurogenic region of the hippocampus (granule cell layer plus subgranular zone) an expected decrease was observed in the total number of BrdU+ cells in irradiated wild type mice at one month after BrdU labeling, indicating similar radiation response between mice and rats (55% decrease relative to non-irradiated wild type controls, FIG. 8A, P<0.05, n=3.) In stark contrast, MCP–/– mice exhibited normal levels of total BrdU+ cells following irradiation (FIG. 8A, n=3 per group.)

Wild type mice exhibited the expected decrease in the proportion of newborn cells that adopt a neuronal phenotype following irradiation relative to non-irradiated controls (FIG. 8B, P<0.05, n=3.). When corrected for total number of BrdU cells, the net loss of neurogenesis in wild type animals was greater than 75% (FIG. 1C, P<0.05, n=3).

There was no difference in neurogenesis in non-irradiated MCP-1–/– null vs. wild type mice, indicating that neurogenesis is normal in the absence of MCP-1 (FIG. 8B-C, P=0.26, n=3) Strikingly, between these two groups there was no detectable decrease in either the proportion of BrdU+ cells adopting a neuronal phenotype nor the total number of newborn neurons in MCP-1–/– mice following irradiation. These data demonstrate that neurogenesis was completely unaffected following irradiation of MCP-1 null animals (FIG. 8A-C), and therefore that MCP-1 activity is necessary for the detrimental effects of irradiation on adult hippocampal neurogenesis. The resistance of MCP-1–/– mice to the effects of irradiation on neurogenesis at two months following irradiation is a surprisingly robust finding, and speaks to either the importance of MCP-1 in inflammatory cell recruitment to brain and status of the precursor cell's microenvironment or to a possible direct effect of MCP-1 on neural precursor cells. Given this very robust effect, antagonists or inhibitors of MCP-1, which may include small molecule inhibitors, siRNAs, biologic effector molecules, and other modulators of MCP-1 or MCP-1 receptor (CCR2) action will have profound restorative effects on neurogenesis following irradiation.

Example 4

Absence of MCP-1 Protects Adult Neurogenesis from the Delayed Effects of Cranial Radiation Cranial irradiation reduces adult hippocampal neurogenesis through several mechanisms. Ionizing radiation induces an acute apoptosis in dividing progenitor cells thereby reducing the pool of mitotically active progenitor cells (Mizumatsu, S. et al. Extreme sensitivity of adult neurogenesis to low doses of X-irradiation. *Cancer Res.* 63, 4021-4027, 2003; Limoli, C. L. et al. Radiation response of neural precursor cells: linking cellular sensitivity to cell cycle checkpoints, apoptosis and oxidative stress. *Radiat. Res.* 161, 17-27, 2004). Subsequent changes to signaling within the progenitor cell microenvironment reduce the fraction of active cells that adopt a neuronal fate and also reduce the integration and long-term survival of those few neurons that are produced (Monje, M. L., Toda, H., & Palmer, T. D. Inflammatory blockade restores adult hippocampal neurogenesis. *Science* 302, 1760-1765, 2003; Ekdahl, C. T., Claasen, J. H., Bonde, S., Kokaia, Z., & Lindvall, O. Inflammation is detrimental for neurogenesis in adult brain. *Proc. Natl. Acad. Sci. U.S.A* 100, 13632-13637, 2003). Together, these effects can virtually eliminate neurogenesis in adult rats for several months following a single exposure to 10 Gy cranial X-irradiation. Rodents are more radio-resistant than humans and a 10 Gy dose is typically used to approximate a histological injury response that is similar to a 2 Gy dose in humans. Microglial recruitment and activation plays a significant role in this injury response and it has been demonstrated that the extent of microglial activation inversely correlates with neurogenesis (Monje et al., supra). The data below address the role of MCP-1 in initiating and maintaining this chronic microglial activation in the irradiated brain and the mechanism of the resulting effects upon neurogenesis.

Young adult BalbC mice and BalbC mice null for the MCP-1 protein (MCP-1−/−) according to Lu et al. (Lu, B. et al. Abnormalities in monocyte recruitment and cytokine expression in monocyte chemoattractant protein 1-deficient mice. *J. Exp. Med.* 187, 601-608, 1998; Muessel, M. J., Klein, R. M., Wilson, A. M., & Berman, N. E. Ablation of the chemokine monocyte chemoattractant protein-1 delays retrograde neuronal degeneration, attenuates microglial activation, and alters expression of cell death molecules. *Brain Res. Mol. Brain Res.* 103, 12-27, 2002) were treated with a single exposure to 10 Gy cranial irradiation and then allowed to recover for 4 weeks. BrdU was then injected once each day for 6 days (50 mg/kg, IP) to label dividing cells. Animals were then sacrificed 3 weeks after the last BrdU injection (2 months after irradiation). Tissues were immunostained for BrdU to detect newborn cells, Iba-1 to identify all monocyte/microglia lineage cells, and FA-11 (CD68) to monitor monocyte activation state (FIG. 9B-G). CD68 is a lysosome-associated epitope that is upregulated in activated macrophages and microglia 29, 30. The fraction of BrdU-positive cells that co-labeled for Iba-1 was determined by confocal microscopy (FIG. 9B, b). Cranial irradiation in wild type animals was accompanied by a continuing proliferative recruitment of monocytes/microglia, even 4 weeks after irradiation (elevated from 4±1% (n=9) in wild type controls to 31±6% ($p<0.001$, n=9) in irradiated wild type animals, FIG. 9E). In contrast, the absence of MCP-1 completely normalized the chronic post injury elevation in monocyte proliferation.

Figure 13:
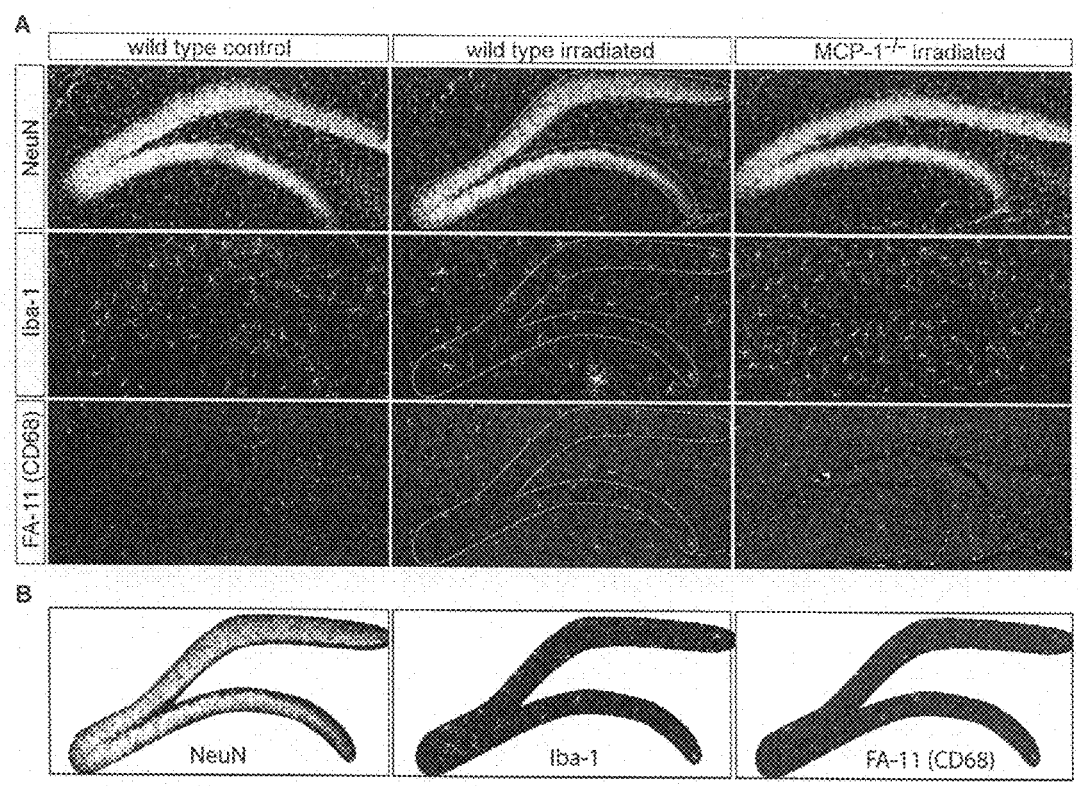

Image analysis of Iba-1 staining was also used to quantify the relative density of Iba-1-positive monocytes/microglia arborization within the dentate gyrus and subgranular layer (FIG. 9C, D, F, G, and FIG. 13). Microglial staining was present at similar densities in wild type and MCP-1−/− animals before irradiation and treatment did not significantly increase Iba-1 staining density in either wild type or MCP-1−/− animals (FIG. 9F). In contrast, the intensity of FA-11/CD68 staining increased by 1.8 fold ($p<0.05$) in wild type animals following radiation but showed no significant increase in MCP-1−/− animals ($p>0.05$, n=5), indicating that the absence of MCP-1 reduced both proliferative response and the level of chronic microglial activation normally seen following cranial irradiation (FIG. 9G).

Figure 10:
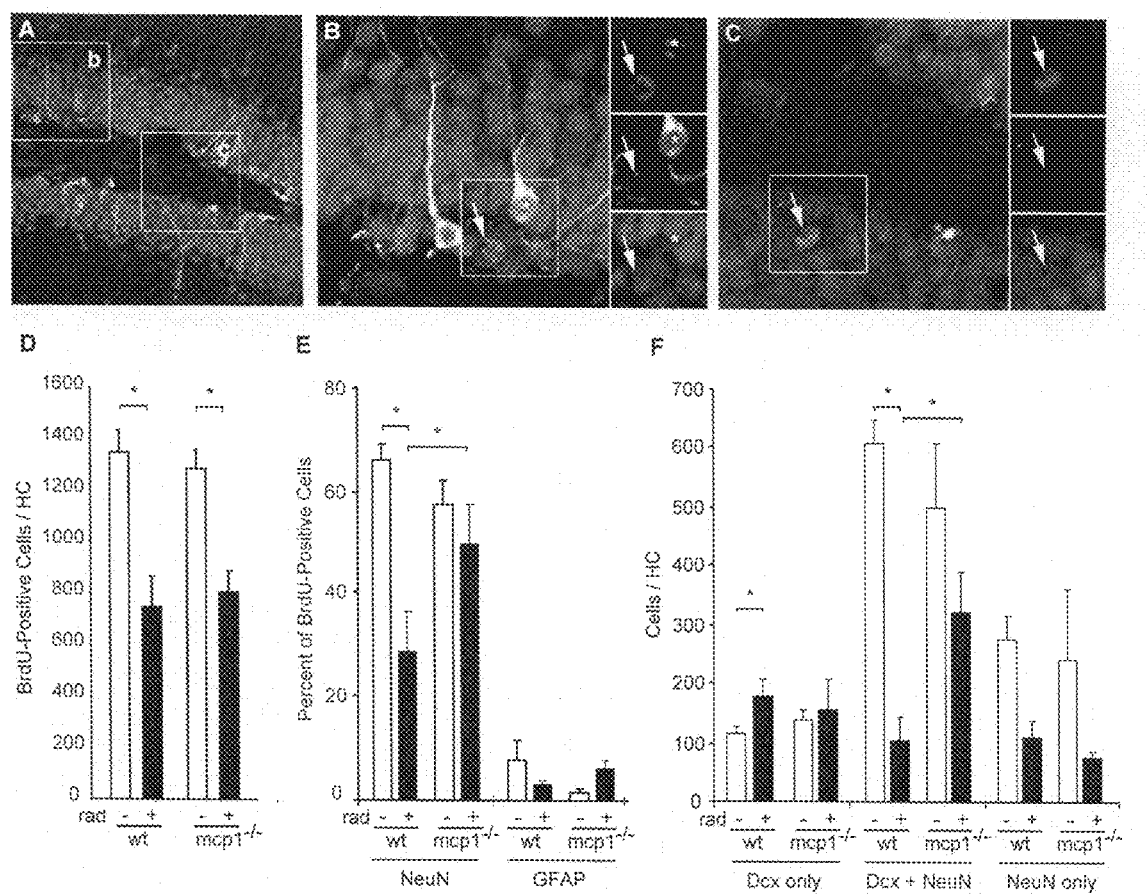
Figure 11:
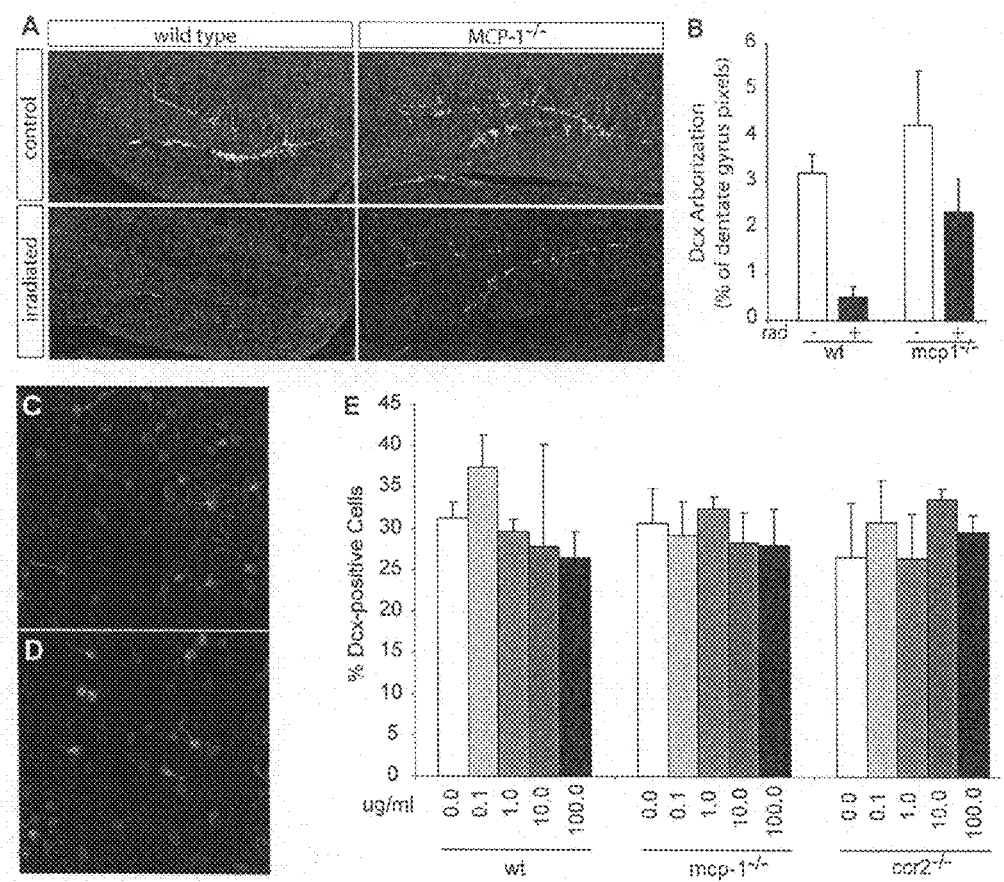

To determine if the attenuation of microglial recruitment was accompanied by a normalization in neurogenesis, brain sections were stained for BrdU, NeuN (a marker for mature neurons)and glial fibrillary acidic protein (GFAP), a cytoskeletal protein expressed by astrocytes and the stem cell population within the hippocampus (FIG. 10). Stereological estimates of total BrdU-positive cells per hippocampus showed that irradiation reduced the net production of newborn cells in the hippocampal dentate gyrus from 1349±87 cells in wild type control animals to 747±120 cells following irradiation ($p<0.001$, n=9, FIG. 10D). Similarly, MCP-1−/− IR animals show a 37% decrease ($p=0.05$, n=5) in the total number of proliferating cells from 1286±71 cells non-irradiated animals to 806±81 cells following irradiation, thus indicating that the absence of MCP-1 did not protect from the radiation-induced depression of newborn cells. In contrast, the absence of MCP-1 did prevent deficits in neurogenesis by normalizing the proportion of newborn cells that adopted a neuronal fate (FIG. 10E). In wild type animals, irradiation was accompanied by a 56% decrease ($p<0.001$) in the fraction of long-term surviving NeuN-labeled cells while irradiation had no effect on neuronal fate in MCP-1−/− animals. This indicates that neurogenic signaling within the hippocampal progenitor microenvironment is normalized in MCP-1−/− animals within one month of cranial irradiation.

To determine if the attenuation of microglial recruitment was accompanied by a normalization in neurogenesis, brain sections were stained for BrdU, NeuN (a marker for mature neurons)31 and glial fibrillary acidic protein (GFAP), a cytoskeletal protein expressed by astrocytes and the presumptive stem cell population within the hippocampus (FIG. 10). Stereological estimates of total BrdU-positive cells per hippocampus showed that irradiation reduced the net production of newborn cells in the hippocampal dentate gyrus from 1349±87 cells in wild type control animals to 747±120 cells following irradiation ($p<0.001$, n=9, FIG. 10D). Similarly, MCP-1−/− IR animals show a 37% decrease ($p=0.05$, n=5) in the total number of proliferating cells from 1286±71 cells non-irradiated animals to 806±81 cells following irradiation, thus indicating that the absence of MCP-1 did not protect from the radiation-induced depression of newborn cells. In contrast, the absence of MCP-1 did prevent deficits in neurogenesis by normalizing the proportion of newborn cells that adopted a neuronal fate (FIG. 10E). In wild type animals, irradiation was accompanied by a 56% decrease ($p<0.001$) in the fraction of long-term surviving NeuN-labeled cells while irradiation had no effect on neuronal fate in MCP-1−/− animals. Thus, neurogenic signaling within the hippocampal progenitor microenvironment is normalized in MCP-1−/− animals within one month of cranial irradiation.

The dramatic loss of Dcx positive arborization in irradiated animals, along with the increase in Dcx-alone BrdU-positive cells indicates that a component of the inflammatory cascade mediated by MCP-1 specifically blocks the maturation of newborn neurons at a very early stage, i.e., prior to arborization. To determine if MCP-1 was acting directly on neural progenitor cells to mediate these effects, brains from wild type, MCP-1$^{-/-}$, or CCR2$^{-/-}$ mice were enzymatically dissociated and neurosphere cultures established in growth medium (Neurobasal-A, B27 supplement, 10 ng/ml EGF, 20 ng/ml FGF-2). Neurospheres were dissociated at passage 2-3 and plated as monolayers on laminin coated dishes and then induced to differentiate by replacing growth medium with differentiation medium (Neurobasal-A, B27, 1 ng/ml FGF-2, 100 nM all-trans retinoic acid, 10 ng/ml BDNF, 10 ng/ml NT3). Increasing concentrations of recombinant mouse MCP-1 (rmMCP-1) were added to the medium and cells were allowed to differentiate for 5 days. Cells were then fixed and stained for Dcx (FIG. 11C-C). Within 5 days of differentiation, a proportion of cells became positive for Dcx. Comparison of cultures from wild type vs. MCP-1- or CCR2-null animals showed that baseline differentiation was not affected by the absence of endogenous MCP-1 or its receptor CCR2. Similarly, addition of rmMCP-1 up to a final concentration of 100 ug/ml had no effect on the number of neurons produced. Neither was the extent of arborization influenced by the addition of rmMCP-1 (FIG. 11E). This indicated that that the MCP-1-dependent neurogenic blockade was not due to the direct actions of MCP-1 on neural progenitor cells but was instead due to the indirect modification of non-progenitor cells and/or cell-derived growth/trophic factors that occupy the progenitor cell microenvironment in the hippocampus.

Figure 12:
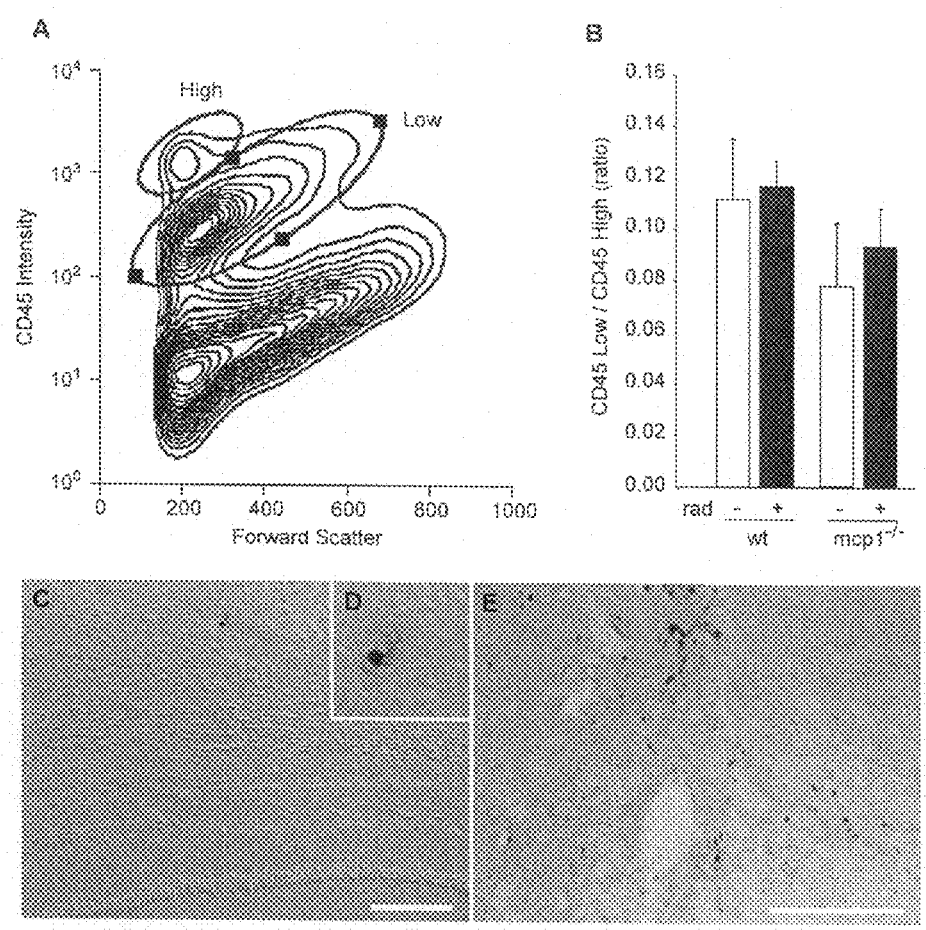

MCP-1 is best known for its role in recruiting circulating macrophages to sites of tissue injury and while MCP-1$^{-/-}$ mice are known to have a defect in monocyte extravasation and amplification in peripheral tissues, there is little known about the recruitment of peripheral macrophages following cranial irradiation or the role that MCP-1 plays in this process. To determine if recruitment of peripheral macrophages to the irradiated brain might contribute to the alterations in the progenitor microenvironemt, irradiated and control brains were harvested one week after 10 Gy irradiation and enzymatically dissociated into single cells. Percoll was used to enrich for leucocytes and eliminate mature neurons, glia, and myelinated neuropil. The remaining cells were stained for CD45 to identify all immune cells and CD11b to identify monocytes. Prior reports have shown that peripheral macrophages can be distinguished from resident microglia by elevated CD45 expression. Flowcytometric analysis of cells isolated from irradiated wild type or MCP-1$^{-/-}$ animals showed that there was no difference in the proportion of CD45 low vs. high monocytes following irradiation in either genotype indicating that CD45-high macrophages are not recruited to the brain in significant numbers during the week following irradiation (FIG. 12A, B).

Figure 14:
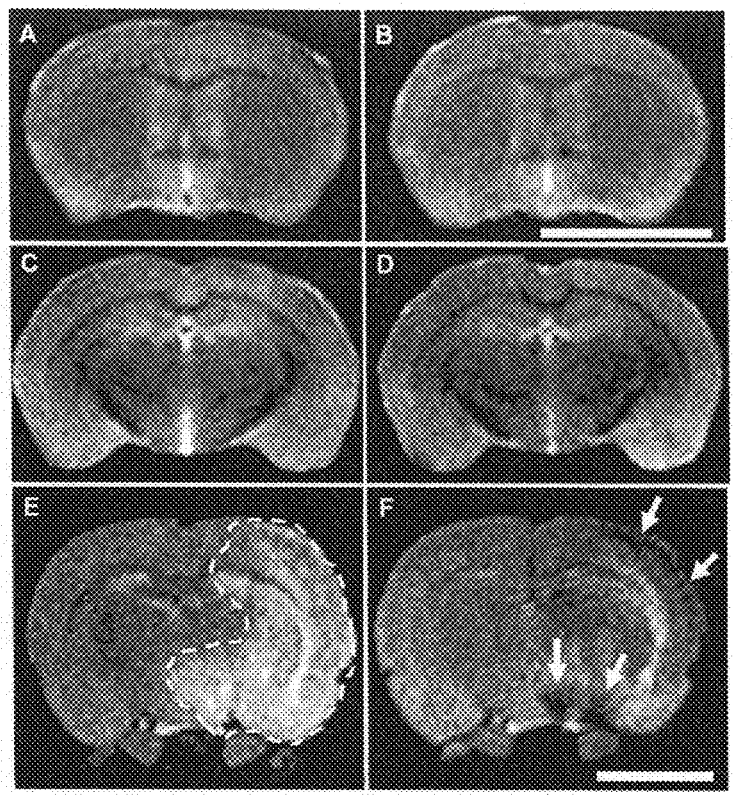

A second method was also used to determine if peripheral macrophages could be detected in the brain following irradiation. Wild type and MCP-1$^{-/-}$ animals were irradiated with a single 10 Gy cranial dose that was restricted to one hemisphere with lead shielding. On day 4 or 6 after irradiation, animals were injected intravenously with a single bolus of dextran-coated super-paramagnetic iron nano-particles (Combidex, 1 mg/kg in saline), which are rapidly phagocytized by circulating monocytes. The animals were then subjected to magnetic resonance imaging on day 7 to determine if iron-mediated hypo-intense areas could be detected within the column of irradiation in the irradiated hemisphere (FIG. 14). Brains were subsequently harvested and evaluated histologically with Prussian blue staining for iron-loaded macrophages. As a positive control for tissue injury and macrophage recruitment, tissues from rats that had been subjected to an acute focal ischemia 4 days prior to evaluation were also examined (FIG. 12C-E). Although labeled macrophages were aggressively recruited to areas of focal ischemic injury, there was no recruitment of labeled macrophages in either wild type or MCP-1$^{-/-}$ animals following irradiation.

In combination, the present data indicates that there are two neurogenic deficits induced by cranial irradiation. First, the number of surviving newborn cells remains substantially reduced by irradiation through the two-month time point evaluated in the present study; the absence of MCP-1 has no effect on this loss. Second, MCP-1 is necessary for creating a microenvironment that chronically inhibits neurogenesis by a blockade to neuronal maturation and arborization.

Our results in vitro indicate that the MCP-1 effects on neurogenesis are not mediated by direct activation of the CCR2 receptor on progenitor cells but rather through an indirect effect of MCP-1 on other cell types within the neurogenic niche of the hippocampus. Earlier work has suggested peripheral macrophages may play a role in mediating these effects (Monje et al., supra) but our current studies show that a single exposure to ionizing radiation does not significantly recruit peripheral macrophages in this model at the acute time points studied. The conclusion is that MCP-1 mediates one or more changes in local cell signaling that inhibits newborn neuron arborization and maturation through changes in the interactions between progenitors and those cells present within the local microenvironment.

Microglia therefore remain prime candidates for mediating the blockade to neuronal maturation but the MCP-1 receptor, CCR2 (a pertussis toxin-sensitive heterotrimeric G-protein-coupled receptor) is expressed by virtually all cell types in the CNS, including neural progenitor cells, astrocytes, and endothelial cells. Both neurons and neural progenitors have been shown to respond to MCP-1, as assessed by calcium imaging or directed migration. Biological and small molecule CCR2 antagonists are increasingly entering the clinical arena for a broad range of non-CNS inflammatory or cancer indications and it is likely that one or more of these molecules will be effective at normalizing progenitor cell function. MCP-1 antagonists can be added to a growing arsenal of agents that attenuate cognitive decline following therapeutic irradiation or other forms of CNS injury or disease that are accompanied by inflammatory disruption of neurogenesis.

Methods

Irradiation. MCP-1$^{-/-}$ and CCR2$^{-/-}$ animals were kindly provided B. J. Rollins and E. Mocarski. Age matched congenic wild type control BALB/c mice were purchased from Jackson Laboratories. 2-3 month old adult male mice were anesthetized with ketamine and xylazine and exposed to cranial irradiation using a Philips orthovoltage X-ray system operated at 200 kVp and 20 mA. On Day 0, a single dose of 10 Gy was limited to the cranium of each mouse with lead shielding of the body, neck, eyes, ears and snout. Dosimetry was using TLD dosimeters (K & S Associates, Nashville, Tenn.) buried in the hippocampi of euthanized mice confirmed a total 10 Gy dose at hippocampal depth. The dose rate was approximately 78.0 cGy/minute. Sham-irradiated controls for all experiments received anesthesia only.

BrdU injections and tissue preparation. Animals were injected intraperitoneally with BrdU once per day for 6 days (50 mg/kg total dose using a 10 mg/ml solution in saline, Sigma) on days 28-33 after irradiation. Animals were maintained for an additional month and then anesthetized and sacrificed two months (day 56) after irradiation by transcardial perfusion with 4% paraformaldehyde. Brains were removed, postfixed overnight, and then equilibrated in phosphate buffered 30% sucrose. Free floating 40 um sections were collected on a freezing microtome and stored in tissue cryoprotectant solution at −20° C. until used.

Immunohistochemistry. Free floating sections were immunostained as previously described in using the following primary antibodies and working concentrations: mouse anti-NeuN (1:500, Chemicon, Temecula, Calif.); goat anti-doublecortin (1:500, Santa Cruz Biotechnology, Santa Cruz, Calif.); rabbit anti-Iba-1 (1:1500, Wako, N.J.); rat anti-BrdU (1:500, Accurate Chemical, Westbury, N.Y.); rat anti-CD68 (Fa-11; 1:40, Serotec, Raleigh, N.C.); guinea pig anti-GFAP (1:750, Advanced Immunochemicals, California); mouse anti-APC (1:100, Calbiochem, San Diego, Calif.), biotinylated tomato lectin (*Lycopersicon esculentum*) (1:200, Vector Laboratories, Burlingame, Calif.). Minimally cross-reactive secondary antibodies produced in donkeys to recognize the appropriate primary antibody species and isotype were purchased from Jackson ImmunoResearch (West Grove, Pa.). For animals injected with Combidex®, iron detection was achieved using the standard Prussian blue reaction (2% hydrochloric acid and 2% potassium-ferricyanide in distilled water).

Flow cytometry. Mice were anesthetized with ketamine and xylazine. Brains were removed and rinsed with PBS. Whole brains were mechanically minced and enzymatically dissociated using a mixture of papain (Worthington, Lakewood, N.J.), neutral protease dispase II (Roche, Indianapolis, Ind.), and DNAse (Worthington) as previously described. After1 hour dissociation at 37° C., single cell suspensions were fractionated over a step-gradient of Percoll and a monocyte-enriched fraction was collected at the interface between 25% and 70% Percoll solutions in PBS. Cells were washed twice in media consisting of DMEM/F12 and 10% heat inactivated FCS. Cells were stained live using FITC-anti mouse CD45 (1:500) and PE-anti mouse CD11b (1:500) (BD Pharmingen, San Diego, Calif.) for 10 min at 4° C. Subsequently, cells were washed 3 times in PBS and fixed with 2% Paraformaldehyde for 5 minutes. Becton Dickinson FACScan and CELLQuest software were used for cell analysis and data acquisition. FlowJo software was used for postacquisition analysis.

Confocal microscopy. All confocal microscopy was performed using a Zeiss LSM 510 Meta confocal microscope. Appropriate gain and black level settings were determined on control tissues stained with secondary antibodies alone. Upper and lower thresholds were always set using the range indicator function to minimize data loss through under or over saturation.

Cell quantification and unbiased stereology. All counts were limited to the hippocampal granule cell layer proper and a 50 um border along the hilar margin that included the neurogenic subgranule zone. The proportion of BrdU cells displaying a lineage-specific phenotype was determined by scoring the co-localization of cell phenotype markers with BrdU using confocal microscopy. Split panel and z-axis orthogonal projections were used for all counting to minimize false positives. All counts were performed using multi-channel configuration with a 40× objective and electronic zoom of 2. When possible, 100 or more BrdU-positive cells were scored for each marker per animal. Each cell was manually examined in its full "z"-dimension and only those cells for which the nucleus was unambiguously associated with the lineage-specific marker were scored as positive. The total number of BrdU-labeled cells per hippocampal granule cell layer and subgranule zone was determined using immuno detection of BrdU followed by HRP-coupled secondary antibodies and diaminobenzadine stain (Vector Laboratories). Stained BrdU-positive nuclei were scored under light microscopy using Microbrightfield Stereo Investigator software and a modification of the di-sector method where random grid placement provided provided systematic and unbiased sampling of BrdU cell density within the dentate gyrus. Nuclei at both cut surfaces were scored and over estimation was corrected using the Abercrombie method for nuclei with empirically determined average diameter of 13 um within a 40 um section. All analyses were performed by investigators blinded to sample identity and treatment group.

Pixel Intensity and Staining Density Analysis. Low magnification images of the dentate gyrus were collected on the confocal microscope with a 10× objective using care to first establish gain and offset settings that ensured all pixels within any given section fell within the photomultiplier detection range (no undersaturated or oversaturated pixels in any tissue section). Images were then collected from all tissues without altering confocal settings. In each image, the dentate gyrus and subgranular zone were outlined and the total number of pixels within the outlined region were recorded. Pixels positive above background for a given marker were subsequently selected and the number of positive pixels within the outlined region of interest also recorded to determine the % dentate area occupied by positive staining. Average pixel intensity for all positive pixels was also recorded to document relative abundance of the detected epitope in immuno-positive cells. Unlike enzyme linked detection systems that deposit insoluble substrates to an opaque endpoint, fluorescent immunological detection reactions that are allowed to reach equilibrium will produce fluorescent signals that are directly proportional to the abundance of the detected epitope.

Combidex® and MRI imaging. Combidex® (ferumoxtran-10, Advanced Magnetics, Inc.) is a lyophilized powder consisting of ultrasmall superparamagnetic iron oxide (SPIO) particles coated with low-molecular-weight dextran. Particle diameter in solution is 170 to 210 Å (17-21 nm). After reconstitution in sterile saline the contrast agent was administered intravenously in a single dose by injection through the tail vein (300 umol of iron per kilogram of body weight). Injections were performed 4 or 6 days after radiation and MR imaging performed on the $7^{th}$ day. High-resolution MR images of the perfused brains were acquired on a 4.7 T/40 cm horizontal animal scanner system (Inova, Varian, Palo Alto, Calif.). First a preliminary scout scan was acquired in the transverse and sagittal planes with a 2D sequential spin echo pulse sequence. This initial localizer scan was used to standardize head tilt and rotation. Subsequently a coronal T2-weighted spin-echo (TRITE 2000/45 ms, Avg. 6, FOV 30 mm, Matrix 256) and aT2*-weighted sequence (3D gradient echo sequence: TR/TE 400/5 ms, Avg. 8, FOV 40 mm, Matrix 256) were acquired.

Middle cerebral artery occlusion (MCAO)As a positive control for peripheral macrophage recruitment, Sprague-Dawley rats (Charles River, Wilmington, Mass.) were evaluated following an experimental focal cerebral ischemic event. Male animals weighing 280-320 g were anesthetized with 2.5% isoflurane in an oxygen/air mixture. Temperature, EKG and respiration rate were monitored throughout the surgery. The common carotid (CCA), external carotid and pterygopalatine arteries were exposed and ligated on the left side. The left internal carotid artery (ICA) was transiently occluded with a microsurgical clip, and an arteriotomy was made in the CCA. A 3.0-monofilament suture (Ethicon, Sommerville, N.J.) with a rounded tip was inserted into the CCA and advanced through the ICA to the ostium of the middle cerebral artery (MCA) to occlude the MCA (MCAO). The suture was left in place for 2 hours, and then removed to allow reperfusion. Combidex injections were administered 3 days after MCAO and 24 h before MR imaging.

Progenitor Cell Culture and Differentiation Whole brains from PO mouse pups were enzymatically digested with a mixture of papain, neutral protease, and DNAse. Neurospheres were cultured on uncoated plates with medium containing Neurobasal A (Gibco), L-glutamine, PSF, B-27 without vitamin A, 40 ng/ml FGF-2, and 40 ng/ml EGF. Cultures were passaged in parallel when reaching confluence and total viable cell counts were made using a hemocytometer to score trypan blue-excluding cells at each passage. Cells were induced to differentiate by plating dissociated cells into laminin-coated multi-chamber tissue culture slides (Nunc) in differentiation media, Neurobasal A, B-27 without vitamin A, 1% fetal bovine serum, 100 nM all trans-retinoic acid, 1 ng/ml FGF-2, 10 ng/ml BDNF, and 10 ng/ml NT3. Murine recombinant monocyte chemoattractant protein-1 (mrMCP-1; 0-100 nM; Peprotech, Rocky Hill, N.J.) was added to some wells and cells allowed to differentiate for 5 days. During this period, cells were fed every other day with fresh media and mrMCP-1. Cells were then fixed with 4% PFA and stained. Confocal photomicrographs (40× zoom of 1) were taken at systematically sampled intervals along a diagonal path through each well, collecting 5 fields per well. Total nuclei per sample site was scored using DAPI, neurons were scored on the basis of Dcx immunoreactivity. No significant differences were detected in either growth or differentiation between wild type and MCP-1$^{-/-}$ or CCR2$^{-/-}$ mice Statistics. All experiments were analyzed using ANOVA. Due to the unequal number of animals in the groups, Spjotvoll/Stoline test was used for posthoc analysis. However, if the groups violated the assumption of homogeneity of variance by Kruskal-Wallis, the Welch's t test was used.

Example 5

PPAR-γ activation protects adult neurogenesis from the effects of LPS-induced inflammation. Vaccinations and over the counter/antiviral drugs primarily shorten, rather than prevent, the course of acute symptomology in healthy adults. These acute symptoms typically subside within 3-7 days, but some evidence suggests that malaise and cognitive impairment can persist long after the symptoms subside. Influenza infection or the cytokines it induces impair memory, attention and executive function in symptomatic humans and one study has shown that attention is impaired for at least two weeks following a mild viral challenge. Cancer patients undergoing chemotherapeutic regimens and multiple sclerosis patients who experience flu-like responses from recombinant cytokine treatment can also develop a syndrome of subjective memory loss, depression and impaired motor and executive function suggesting that these effects may also be influenced by inflammatory mechanisms.

Understanding and attenuating persistent cognitive impairment associated with a virus-induced inflammatory response using the appropriate treatment would provide clear benefit but the effects of transient illness on cognition have been difficult to study in human populations due to variations in virus strain and symptom severity. To circumvent problems with experimental control some groups have utilized a mild gram-negative bacterial lipopolysaccharide (LPS) challenge in humans to study the effects of viral-like illness on cognition. LPS is a bacterial immunogen that mimics influenza by inducing fever, malaise and increased cytokine production. For example, mild LPS challenge is associated with impaired verbal and non-verbal memory in symptomatic humans. In rodents, LPS induces sickness behavior, neuroinflammation and is also known to impair adult hippocampal neurogenesis, a phenomenon that correlates with hippocampus-dependent learning and memory.

The data described herein address the use of intraperitoneal injection of LPS in mice to model the potential long-term effects of inflammation on hippocampal neurogenesis and spatial learning and/or memory. In rodents, systemic LPS administration activates an acute-phase innate immune response that activates immune cells and an elaboration of pro-inflammatory cytokines. In mammals (including humans), the cytokine cascade includes elevated tumor necrosis factor-α (TNF-α), interleukin-1β (IL-1β) and IL-6 as well as hypothalamic-pituitary-adrenal axis activation. This systemic response is thought to be transduced to the brain via interleukin-1β (IL-1β) where it upregulates the central synthesis and release of pro-inflammatory cytokines likely by activating NFκB. The present study demonstrates that this transient flu-like illness is accompanied by decreased neurogenesis and a delayed mild memory deficit that can persist for up to 12 weeks after illness.

Results

Figure 15:
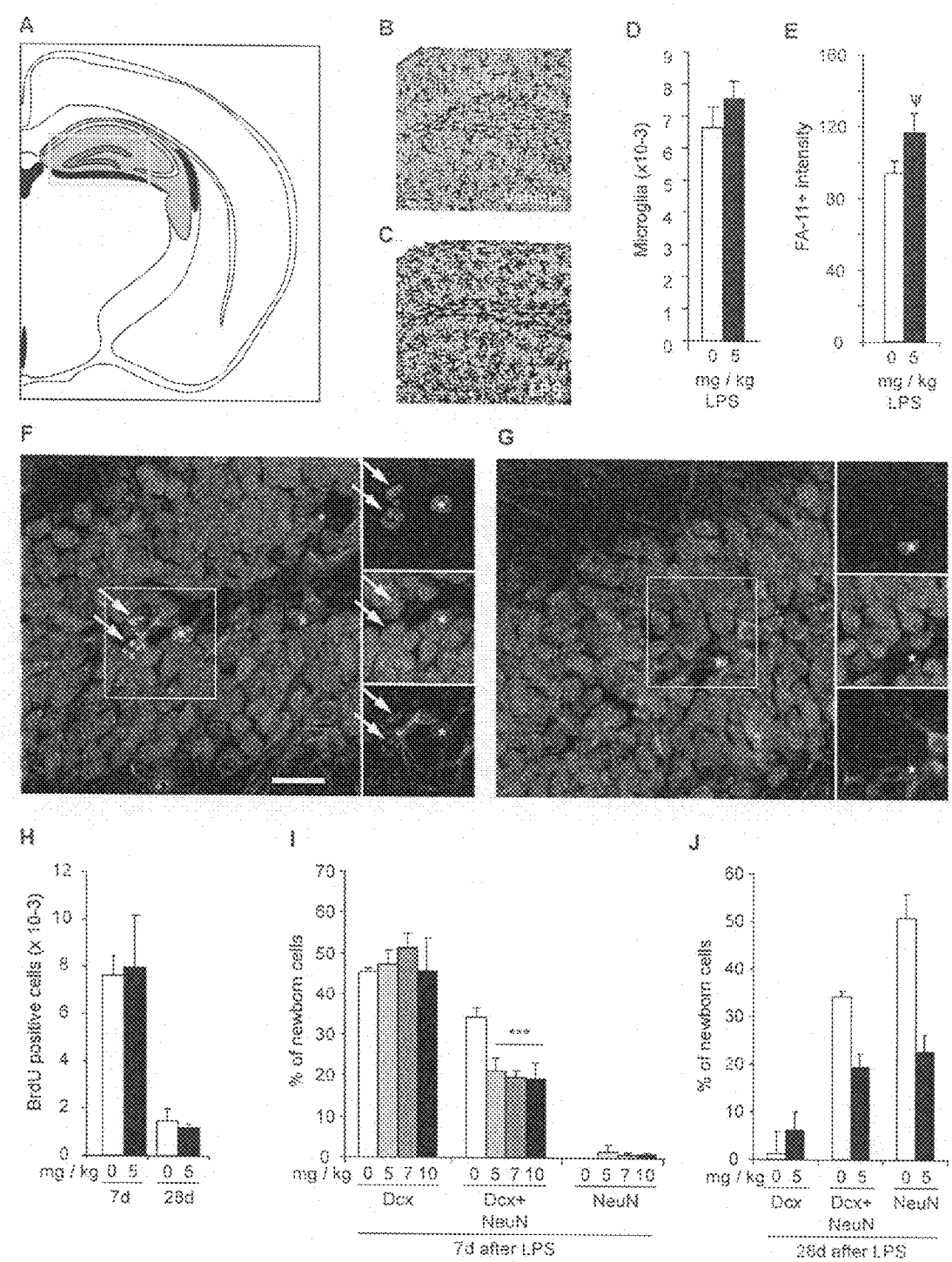

LPS induces inflammation in the brain and reduces neurogenesis. New neurons are added throughout life to the granule cell layer of the mammalian hippocampal dentate gyrus. The progenitor cells that divide to produce new neurons, astrocytes and oligodendrocytes are located within a discrete lamina located between the granule cell layer proper and the hilus (FIG. 15A.). New neurons rapidly extend axons (within 4-10 days) and exhibit electrophysiological and morphological properties similar to mature granule neurons (within 4 weeks) to integrate into part of a circuitry essential for short term acquisition and storage of spatial and temporal information. It has previously been shown that a single intraperitoneal injection of e. coli lipopolysaccharide (LPS) produces a robust microglial response that is associated with ablated hippocampal neurogenesis in the week following injection.

To investigate whether an LPS challenge produces more chronic effects on neurogenesis, adult female C57Bl/6 mice were injected intraperitoneally (i.p.) with 0, 5, 7.5 and 10 mg/kg of LPS and subcutaneously with sterile saline to prevent dehydration. Mice were then injected once daily over the next 6 days with the cell synthesis marker bromodeoxyuridine (BrdU; 50 mg/kg) to label dividing progenitor cells. Histology was performed on sections from mice that were perfused on Day 7 or Day 28. The number of BrdU-labeled (new) or IBA-1-labeled (monocyte/microglial) cells was estimated through hippocampal sets stereologically using enzyme substrate immunohistochemistry and light microscopy and BrdU-labeled cell phenotypes and IBA-1-labeled activation was determined using immunofluorescence and confocal microscopy.

The microglial response that was observed previously in the week following LPS treatment persisted in the brains of adult female mice for at least 4 weeks after a single LPS challenge in the current study. Although total IBA-1 positive cell number was similar in the dentate gyri of vehicle- and LPS-treated mice (FIG. 15B, C and D) 4 weeks after LPS injection, the activation (FA-11/CD68) intensity on IBA-1 positive cells was 1.25-fold higher in the dentate gyri of LPS-treated mice (FIG. 15E). In naïve animals, most newborn cells acquire a neuronal phenotype (FIG. 15F). Consistent with our previous work, the production of newborn neurons was significantly decreased in the dentate gyri of LPS-treated mice (FIGS. 15F to 15J). LPS did not influence neurogenesis by decreasing the proliferative activity of progenitor cells or the survival of progenitor cells/progeny as the total number of BrdU positive cells was similar between vehicle- and LPS-treated groups at both 6 and 28 d after injection (FIG. 15H). However, LPS-treatment did significantly block the ability of progenitor cells to generate neurons. Doublecortin (DCX) protein is expressed by neuroblasts that begin to express neuronal nucleii (NeuN) protein, a marker of mature neurons, as they migrate deeper into the granule cell layer and begin to arborize. As the newborn neurons mature, DCX is downregulated to undetectable levels but NeuN expression persists. LPS treatment significantly impacts transition state neurons; the percentage of BrdU positive (new) colabeled with DCX/NeuN in the dentate gyri of mice was reduced by ≈41% (independent of LPS dose used) in the week following LPS challenge (FIG. 15I). This ablation of neurogenesis was still apparent 4 weeks after LPS challenge, however both transition state and mature neurons were depleted at this time point. BrdU-positive cells colabeled with DCX/NeuN were reduced by ≈44% and BrdU positive cells colabeled with NeuN were reduced ≈57% in the dentate gyri of LPS-relative to vehicle-treated mice (FIG. 15J). The overall effect of this maturational blockade measured 4 weeks after LPS challenge is a 45-55% reduction in the net number of new neurons.

LPS-induced transient illness is associated with mild but persistent memory impairment. Hippocampal neurogenesis, a phenomenon that persists throughout life in men and mice alike, has been linked to learning and memory by several groups. Manipulations that chronically deplete hippocampal neurogenesis produce concomitant impairments in cognition, particularly hippocampus-dependent memory. In addition to the acute sickness behavior that LPS produces in rodents and in humans (fever, lethargy, reduced food and water intake, weight loss and poor grooming behavior), it is herein demonstrated that LPS substantially decreases the number of maturing/mature neurons that integrate into hippocampal circuitry in the weeks following injection. To determine whether LPS-induced illness affects learning and/or memory during either the acute recovery phase or in asymptomatic mice, a single 0 or 5 mg/kg injection of LPS was administered with daily subcutaneous saline injections over 4 days to maintain hydration and their behavior examined in locomotor chambers and/or the Morris water maze task either in the week following treatment or beginning 4 weeks after treatment when the decrease in net neurogenesis is most apparent.

Figure 16:
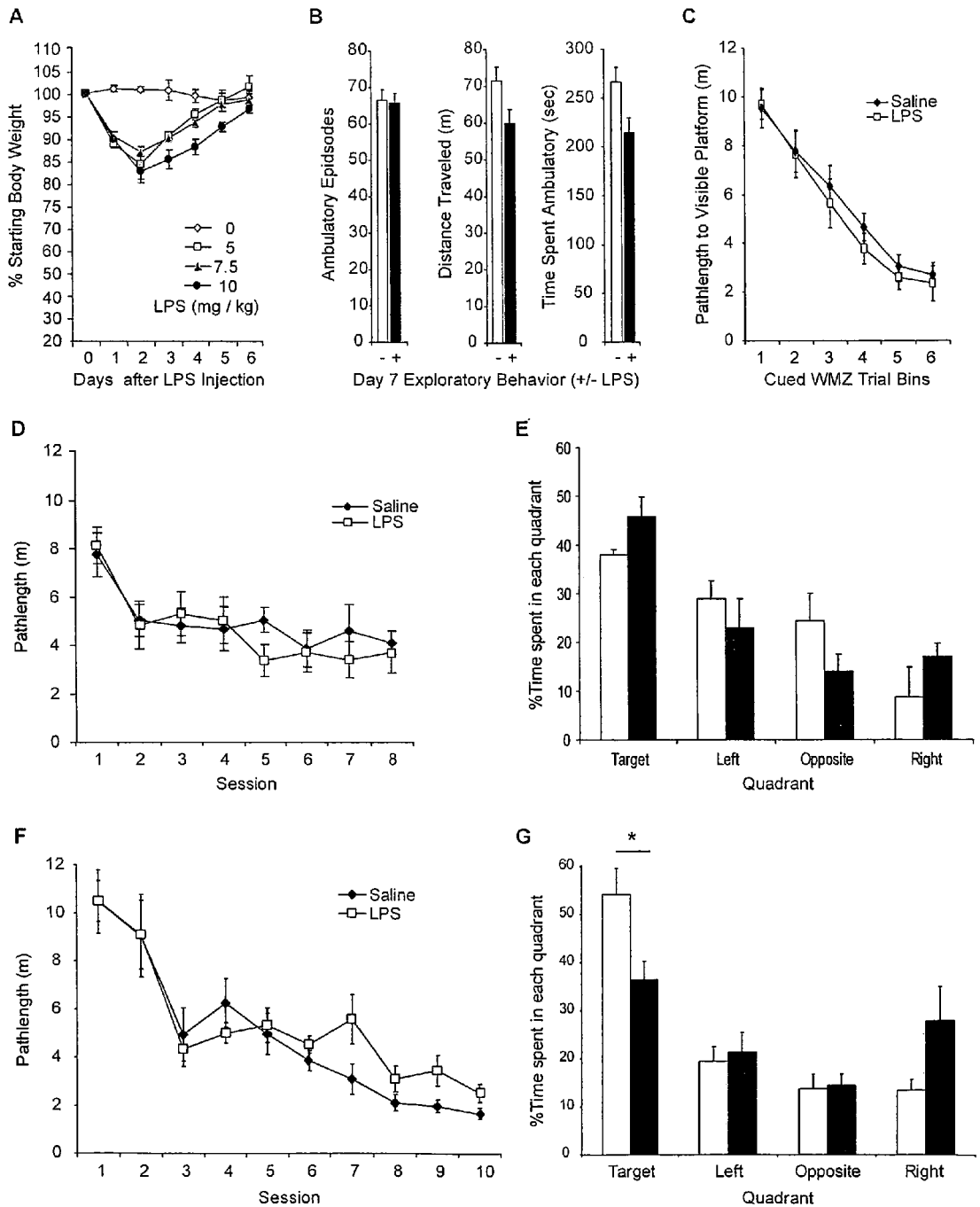

Sickness behavior. Within 1-2 hrs of LPS treatment, the mice exhibited hunching behavior and sweaty fur and exhibited significant weight loss indicative of anorexia. An LPS titration using doses from 5-10 mg/kg shows that even at the lowest dose tested, mice lose roughly 20% body weight but weight loss is transient and is fully restored by day 6 (FIG. 16A). Because the 7.5 and 10 mg/kg doses only prolonged recovery but did not potentiate the effect of LPS on neurogenesis (FIGS. 15I and 15J) behavioral testing was conducted only on mice treated with the 0 mg/kg vs 5 mg/kg dose of LPS. In the next 72 hrs, the mice exhibited lethargy and low mobility in their home cages. These effects are largely reversed by Day 4 but careful analysis of exploratory behavior in locomotor chambers shows that mice are still significantly affected by the prior illness (FIG. 16B). Although LPS-treated exhibited the same motivation to explore a novel chamber environment over a 30 min session (both initiated the same number of explorations), they exhibited significantly shorter exploration times and distances relative to vehicle-treated mice (FIG. 16B), indicative of a malaise similar to that reported in humans with influenza infection. Therefore, our LPS challenge produced many of the sickness behaviors associated with influenza infection.

Spatial ability during acute phase recovery. Mice were first trained to locate a visible platform located in a water maze devoid of extramaze cues, beginning Day 4 post-LPS challenge. On Day 7, the mice were trained on hidden platform trials until they located the platform in under 15 s averaged over a 5-trial session (8 sessions). Once this learning criterion was attained, a probe trial was given in which the platform was removed from the pool and then reversal training trials in which the platform was placed in the quadrant opposite to the original training quadrant commenced. Numerous extramaze cues were identically situated while hidden platform, probe and reversal trials were conducted. Control and LPS-treated mice exhibited similar swim speeds and required the same number of sessions to reach training criterion on the visible platform version of the water maze task (FIG. 16C) as controls, suggesting that in this task LPS-treated mice did not exhibit sensorimotor, motivation or associative learning deficits (FIG. 16C). Control and LPS-treated mice were equally efficient at learning (on training trials; FIG. 16d) and remembering (on a probe trial; FIG. 16E) the position of a hidden underwater escape platform relative to spatial cues placed within the testing room (FIG. 16D). Both training and probe trial performance in this task are dependent upon hippocampal integrity.

Spatial ability in asymptomatic mice. Mice began hidden platform trials on Day 28 and training commenced until they were able to locate the platform in under 15s averaged over a session of 6 trials (10 sessions). One week after achieving criterion on training trials, a probe trial was given, followed by reversal training trials. Finally visible platform trials were conducted in the absence of extramaze cues. When training trials commenced 4 weeks after an LPS challenge, LPS-treated mice spent a significantly smaller amount of time searching the pool quadrant that housed the platform on training trials than control mice (FIG. 16G, despite learning the location of the platform as well as control mice on training trials (FIG. 16F). Because there is a 45-55% reduction in the number of neurons (FIGS. 15H, 15I and 15J) being integrated into the hippocampal circuitry of LPS-treated mice relative to control mice at the time that training trials commence (4 weeks), our finding indicates that reduction in neurogenesis is associated with reduced memory function (FIGS. 16F and G). Importantly, all mice readily acquired the location of a new platform position on reversal trials, suggesting that probe trial performance was indicative of mnemonic ability rather than an artifact of perseveration.

Illness-induced deficits in neurogenesis can be attenuated with appropriately targeted NSAIDs. It has previously been shown that the effects of acute-phase inflammatory response on neurogenesis can be attenuated with the administration of the broad spectrum NSAID, indomethacin. NSAIDs are thought to be therapeutic in a number of neuroinflammatory models because they inhibit cyclooxygenases (COXs; constitutive COX-1 and inducible COX-2) which control the production of prostaglandins. In response to pathogen or cytokine challenge, arachadonic acid is translocated into the cell by several phospholipases $A_2$ ($PLA_2$) where it is converted by COXs to $PGG_2$, by COX peroxidase activity to $PGH_2$ and then by tissue specific synthases to pro-inflammatory prostaglandins ($PGD_2$, $PGE_2$ and $PGF_{2\alpha}$), prostacyclins and thromboxanes which stimulate the production of pro-inflammatory cytokines and participtate in microglial activation. In addition, some NSAIDs activate central peroxisome proliferator-activated receptors-γ (PPAR-γ) to inhibit the production of COX-2 and the transcriptional activity of NFκB. Therefore, indomethacin could protect hippocampal neurogenesis from the deleterious effect of LPS through its inhibitory action on COXs (type1>type2) or by activating PPARγ.

Although effective at controlling neuroinflammation, indomethacin and other broad spectrum NSAIDs that inhibit Cox-1 are associated with reduced platelet production and gastric mucosal insufficiencies. The propensity of NSAIDs to induce ulceration and bleeding often outweigh the anti-inflammatory benefits. In fact, the current study reduced the dose of indomethacin used relative to previous work with rats from 5 mg/kg BID to 1 mg/kg BID because the higher dose produced 100% mortality in mice (FIG. 19). NSAIDs that more selectively target Cox-2, such as roficoxib and celecoxib, are well tolerated and have been widely used as alternatives to broad spectrum NSAIDs for controlling inflammation. In addition, the selective agonism of PPAR-γ is an effective anti-inflammatory strategy, e.g., through administration of thiazolidinediones such as rosiglitazone or pioglitizone. Here, the question is addressed of whether the broad spectrum NSAID indomethacin or the more selective COX-2 inhibitor celecoxib or PPAR-γ activator rosiglitazone can protect hippocampal neurogenesis and/or hippocampus-dependent cognition from the effects of LPS. Mice were started on a 16 day preventative course of oral NSAID and then challenged with a single IP injection of LPS (5 mg/kg) and then BrdU (50 mg/kg) over 6 days beginning 2 h after LPS. The mice were either perfused 28 days after LPS injection, or trained and tested in the Morris water maze.

Figure 17:
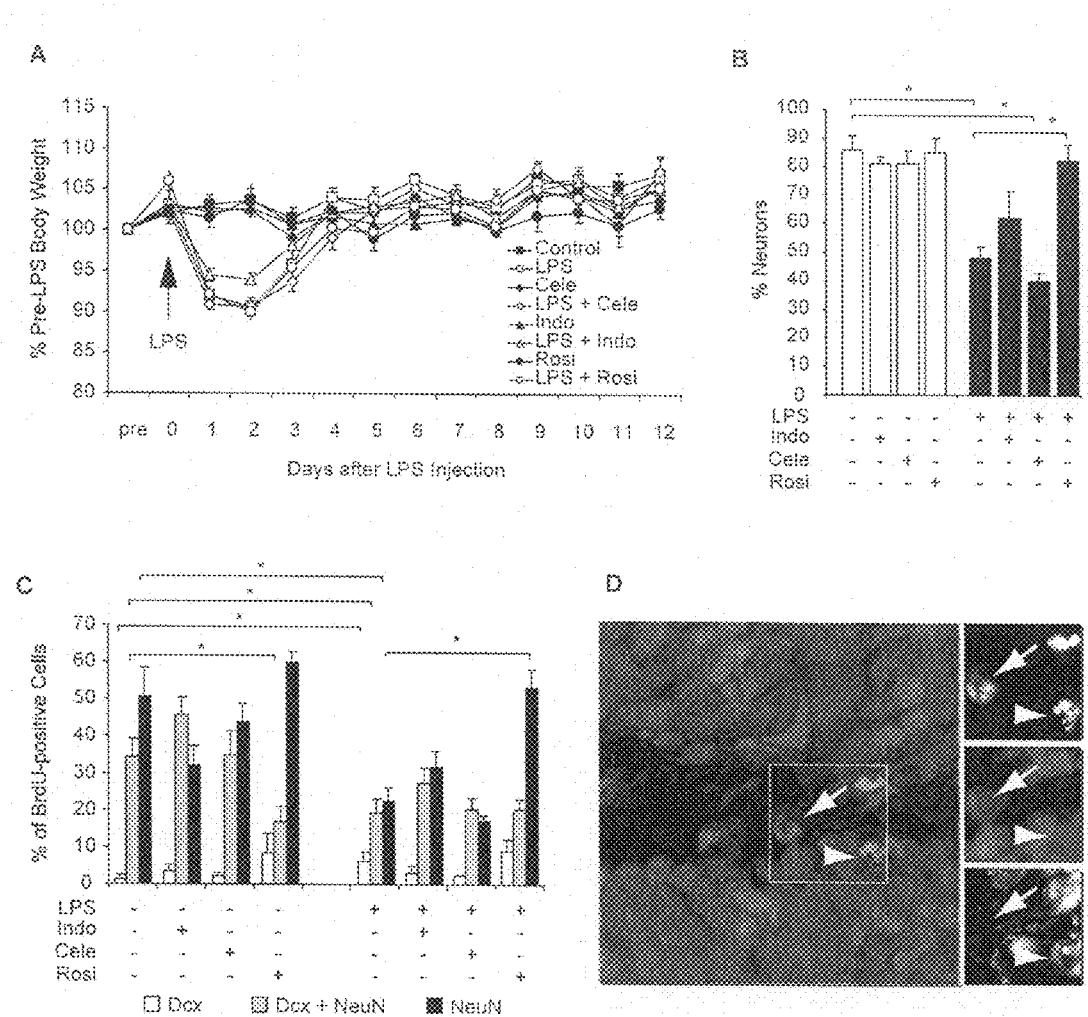

All LPS-treated mice exhibited overt sickness behavior and weight loss following LPS injection. These effects were not significantly attenuated by the administration of indomethacin (Indo), Celebrex (Cele) or Rosiglitizone (Rosi) (FIG. 17A). The fraction of cells born on days 0-6 that adopted a neuronal fate (DCX and/or NeuN expression) by Day 28 was significantly reduced in the dentate gyri of LPS-treated mice. The broad spectrum NSAID indomethacin attenuated, but did not completely reverse this deficit. Celebrex had no protective effect on neurogenesis in LPS-treated mice. However, rosiglitizone completely prevented the LPS-induced deficit in hippocampal neurogenesis (FIG. 17B). Most 3-4 week old (BrdU-labeled) neurons matured into NeuN expressing cells (mature neurons) in the dentate gyri of control mice but many of the NeuN positive cells retained DCX expression (Dcx+NeuN) indicating that they were still transitioning or maturing. Very few new (BrdU positive) cells remained exclusively positive for immature neuronal marker DCX. Transient illness significantly shifted the ratio of immature (DCX) to transition-state (Dcx+NeuN) to mature (NeuN) neurons (FIG. 17C). The fraction of cells that retained an immature phenotype tended to be higher while the fraction of transition-state and mature neurons was significantly lower in the dentate gyri of LPS-treated mice versus controls. The broad spectrum NSAID indomethacin partially reversed the effects of LPS by attenuating the reduction of transition state and mature neurons. The COX-2 inhibitor Celebrex conferred no protection against the effects of LPS on neurogenesis. The PPAR-γ activator rosiglitazone, however, completely rescued neurogenesis from the effects of LPS. FIG. 17D depicts representative examples of DCX positive immature neurons, DCX/NeuN positive transition state neurons and NeuN positive mature neurons.

No significant differences across the 10 sessions of learning trials were observed, with the exception of a slight but significant increased distance swum to the hidden platform mice treated with Celebrex alone over the first training session (FIG. 18A). Transient illness did significantly impair probe trial performance. LPS-treated mice spent significantly less time in the quadrant that housed the platform over training trials relative to controls. Both Indomethacin and Rosiglitazone treatment reversed the effects of LPS on probe trial performance. Surprisingly, mice treated with Celebrex alone performed as badly as LPS-treated mice on the probe trial (FIG. 18B).

Combined, our data indicate that the acute-phase innate inflammatory response induced during transient illness is accompanied by decreased hippocampal neurogenesis and a delayed impairment in spatial memory. These deficits can be partially prevented by a broad spectrum NSAIDs such as indomethacin or a more selective modulator of PPAR-γ activity, such as rosiglitizone. Importantly, the use of Cox-2 selective inhibitors do not appear to be effective in this model and may themselves impact spatial learning memory when administered in the absence of an inflammatory challenge.

Methods

Subjects. All mice used as subjects in this study were treated in accordance with the policies set forth by the Stanford Animal Care and Use Committee and NIH regarding the ethical use of animals for experimentation. CB57Bl/6 mice (7 wks old upon arrival from -Taconic) were housed in groups of 4-5 in autoclaved shoebox cages under standard conditions and were given free access to autoclaved Prolab Mouse 3000 chow (PMI Nutrition International, St. Louis, Mo.) and autoclaved tap water. One week after arrival, vehicle- and NSAID-treated mice were given an intraperitoneal (i.p.) injection of sterile saline or lipopolysaccharide (LPS; 5 mg/kg at a concentration of 1 mg/ml isotonic saline; Sigma Aldrich, St. Louis, Mo.) to induce transient illness (Day 0) and daily subcutaneous (s.c.) isotonic saline (0.5 ml) injections (Days 0-3) to prevent illness-induced dehydration. The cell synthesis marker bromodeoxyuridine (BrdU; Sigma Aldrich, St. Louis, Mo.) was injected i.p. (50 mg/kg at a concentration of 10 mg/ml in freshly prepared isotonic saline) once per day for 6 days to label dividing cells, beginning Day 0 (2 h after LPS). The mice were anesthetized with ketamine/xylazine and killed at Days 7 or 28 (to assess hippocampal neurogenesis during illness and just before behavioral testing, respectively) or Day 80 (to measure hippocampal neurogenesis following behavioural testing) by perfusion with 4% paraformaldehyde. Brains were post-fixed overnight in perfusate, microtome sectioned at 40 μm through the hippocampus and stored in tissue cryoprotectant solution at −20° C. until processed immunohistochemically.

NSAID treatment. One half of the saline- and LPS-treated mice were fed non-steroidal anti-inflammatory drug (NSAID), in low fat strawberry milk, twice per day for two weeks following LPS injection (Days 0-13). The mice were initially introduced to low fat strawberry milk (Berkeley Farms, Calif.; 200 μl per animal) in their home cages, four days before LPS was injected (Days 4 and −3) and were then placed in a PVC tube (10-cm diameter×18-cm height), twice per day (12 h apart) beginning two days before LPS was injected (Days −2 and −1) until they consumed a 100 μl volume of low fat strawberry milk. Beginning the day before LPS was injected (Day −1 through Day 13), the broad spectrum NSAID indomethacin (5 mg/kg or 2 mg/kg, BID; Sigma Aldrich, St. Louis Mo.), the cyclo-oxygenase-1 (COX-1) inhibitor SC-566 (3 mg/kg, BID; Cayman Chemical, Ann Arbor Mich.) the COX-2 inhibitor celecoxib (30 mg/kg, BID; Pfizer, New York, N.Y.) or the peroxisome proliferator-activated receptor-γ (PPARγ) agonist rosiglitazone (20 mg/kg, BID; Stanford Pharmacy, Stanford, Calif.) was added to the milk. All NSAIDs were dissolved in 50 μl ethanol per ml milk and doses were delivered in 100 μl of milk. The NSAID feedings given just before and just after LPS injection were administered in low fat chocolate milk (Berkeley Farms, Calif.), to reduce the probability that mice would associate the mild illness induced by LPS with strawberry milk flavor.

Indomethacin was chosen as the broad spectrum NSAID because of its ability to cross the blood brain barrier, potency in reducing microglial inflammation in vitro and in vivo and its ability to protect hippocampal neurogenesis in models of inflammation. Indomethacin inhibits both monocyte/microglial recruitment and activation. First, indomethacin antagonizes COX expression (type 1>2) which diminishes production of prostaglandin arachadonic acid metabolites that broadly contribute to microglial recruitment and activation. Second, indomethacin agonizes the transcription factor PPAR-γ to inhibit the elaboration of pro-inflammatory cytokines in monocytes/microglia.

Behavioral testing. Locomotor activity was measured in 17×17 inch chambers lined with three 16-beam infrared arrays in photocell boxes (MED Associates, Inc., St. Albans, Vt.). The mice were placed into the chambers and their locomotor activity was recorded for 20 minutes 4 days after LPS was injected (on Day 4). A 50 msec scanning rate was used for measuring beams broken. Distance traveled was analyzed for estimates of locomotion based on the movement of a given distance and resting delay (movement in a given period) using Open Field Activity software (MED Associates, Inc., St. Albans, Vt.).

Hippocampus-dependent learning and memory was assessed in the standard Morris water maze task. All hippocampus-dependent training and testing was conducted in a black circular tank (170 cm diameter×43 cm height) filled water made opaque using white non-toxic Tempra paint (Rich Art Color Co. Inc, Northvale, Calif.; training and testing). A platform (13 cm diameter×28.5 cm height) was hidden 1 cm below the water surface for platform shaping and training trials. Time and distance traveled in the pool was recorded using Videotrack Automated Behavioral Analysis System (Viewpoint Life Sciences Inc., Otterburn Park, Quebec).

Platform shaping began three days before platform training (Days 25-27). In the absence of extra-maze cues, mice were released from random points in the pool (filled with clearwater) near the platform and gently guided to the platform. Shaping trials continued until the mouse remained on the platform for 15 s over 3 consecutive trials on each of the three sessions.

Platform Training began 4 weeks (Day 28) after LPS was injected. In the presence of extra-maze cues, the mice were released from the middle of the east, south, or west quadrant, facing the pool wall, and were given 120 s to find the platform hidden beneath opaque water in the center of the north quadrant. If the mice did not locate the platform in 120 s or less, they were guided gently to the platform and removed after 10 s to a warmed holding cage. Sessions of 6 training trials (inter-trial interval of approximately 30 min) were conducted daily until all the mice located the platform in an average of 15 s or less within a session. Mice that did not reach criterion by Session 10 were excluded from the probe trial testing. Pathlength and latency were analyzed as measures of learning, swim speed was analyzed as a measure of sensorimotor ability and % time spent in outer annulus was analyzed as a measure of anxiety.

Probe Trial Testing was conducted at 1 week after mice reached criterion in the platform training phase of the experiment. The room setup was identical for platform training and probe trials, with the exception that the platform was removed from the pool during probe trials. The mice were given a single trial in which they were released from the center of the pool and then after 3 minutes were removed from the location that held the platform during training trials. Percent time and distance spent in each quadrant were analyzed as measures of memory, swim speed and total distance swum were analyzed as measures of sensorimotor ability and % time and distance spent in the outer annulus were analyzed as measures of anxiety. After the last probe trial, we ran four daily sessions of reversal trials (4 trials per session) in which mice were given 120 s to locate the platform hidden beneath opaque water in the south quadrant to better interpret whether probe trial performance was indicative of memory or perseveration. Good probe trial performance was interpreted as good memory if good reversal learning was also exhibited. A visible platform session (2 trials) was administered after the final reversal trial to further test sensorimotor ability. Reversal and visible platform trial performance was scored identically to platform training performance.

Histology and Immunohistochemistry. Free floating sections were immunostained as described previously using the following primary antibodies and working concentrations: rat anti-bromodeoxyuridine (1:500; Accurate, Westbury, N.J.) goat anti-doublecortin (1:500; Santa Cruz, Calif.), rabbit anti-IBA4 (1:2000; WAKO, Los Angeles, Calif.), rabbit anti-FA-11 (CD68; 1:200; Serotec, Raleigh, N.C.), guinea pig anti-GFAP (1:750; Harlan, Indianapolis, Ind.), rabbit anti-NG2 (1:2000; a gift from W. Stallcup), mouse anti-NeuN (1:500; Chemicon; Temeculah, Calif.). Tissue was incubated in all primary antibodies overnight (and in anti-BrdU for 48 h) at 4° C. Phenotyping sets were incubated in minimally cross-reactive secondary IGg conjugated fluorophores (1:500; Jackson Immunoresearch, West Grove, Pa.) overnight at 4° C. and coverslipped under PVA-DABCO. Stereology sets were incubated for 4 hrs at room temperature in minimally cross-reactive biotinylated secondary antibodies (1:500; Jackson Immunoresearch, West Grove, Pa.) and then revealed using diaminobenzidine or alkaline phosphatase, dehydrated and coverslipped under permount.

Cell Counting and Unbiased Stereology. BrdU-labeled cells were phenotyped and total BrdU-labeled and IBA4-labeled cell numbers stereologically estimated if they were located in the hippocampal granule cell layer proper and subgranular zone (the neurogenic zone that includes a 50 μm border between the hilus and granule cell layer). BrdU-labeled cells were phenotyped on immunofluorescent stained sections that were anatomically matched using a Zeiss 510 Meta confocal microscope using a multi-channel configuration with a 40× objective and electronic zoom of 2.3. Appropriate gain and black level was set using control sections stained with secondary antibodies alone. A BrdU-labeled cell was scored as co-labeled when a full "z-dimension" scan revealed its nucleus was unambiguously associated with a lineage specific marker. Proportions of BrdU-labeled cells co-labeled with lineage specific markers were determined by scoring at least 50 cells per mouse and 100 cells when possible. Activated microglia were analyzed on sections stained with anti-FA-11 and anti-IBA4 by taking a single confocal scan using a 10× objective at the z-stack of the section exhibiting the strongest anti-IBA4 signal (anti-FA-11 signal was set for the series by optimizing gain and black level on a section with median FA-11 stain intensity). The total number of BrdU-labeled and of IBA4-labeled cells was estimated on diaminobenzidine and alkaline phosphatase stained sections, respectively under light microscopy (Nikon Eclipse E600) using Microbrightfield Stereo Investigator software (Williston, Vt.) and the fractionator method.

Data analysis. All behavioral and histological analyses were conducted by experimenters blind to treatment group mice were assigned to. Statistical analyses were performed using Statistica software (Tulsa, Okla.). In experiment 1, the dependent variables were analyzed with students t-tests using treatment (vehicle and LPS) as the independent variable. In repeated measures comparisons conducted for experiment 1, the dependent variables were each analyzed using an analysis of variance (ANOVA) with treatment (vehicle and LPS) as the independent variables. In all other experiments, the dependent variables were each analyzed using an analysis of variance (ANOVA) with treatment (vehicle, SC-566, celecoxib and rosiglitazone) as the independent variable. Statistically significant effects revealed by the ANOVA were explored using Newman Keuls post hoc tests. All statistical tests set $\alpha$ to 0.05.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

It is to be understood that this invention is not limited to the particular methodology, protocols, cell lines, animal species or genera, and reagents described, as such may vary. It is also to be understood that the terminology used herein is for the purpose of describing particular embodiments only, and is not intended to limit the scope of the present invention, which will be limited only by the appended claims.

As used herein the singular forms "a", "and", and "the" include plural referents unless the context clearly dictates otherwise. All technical and scientific terms used herein have the same meaning as commonly understood to one of ordinary skill in the art to which this invention belongs unless clearly indicated otherwise.

What is claimed is:

1. A method of screening a candidate agent for activity in reducing loss of neurogenesis resulting from neuroinflammation, the method comprising:
    contacting a model for neuroinflammation with a candidate agent,
    measuring monocyte chemoattractant protein-1 (MCP-1) activity, and
    determining the effectiveness of said agent in reducing loss of neurogenesis;
    wherein a determination that an agent inhibits MCP-1 or MCP-1 receptor (CCR2) activity is a determination that the agent will have activity in reducing loss of neurogenesis.

2. The method of claim 1, wherein the model of neuroinflammation is an animal model, selected from a rodent challenged with LPS; and a rodent subjected to cranial irradiation.

3. The method of claim 2, wherein said measuring is performed with central nervous system tissue.

4. A method of screening a candidate agent for activity in reducing loss of neurogenesis resulting from neuroinflammation, the method comprising:
    contacting a model for neuroinflammation with a candidate agent,
    measuring the activity of peroxisome proliferator-activator-γ (PPAR-γ), and
    determining the effectiveness of said agent on reducing loss of neurogenesis,
    wherein a determination that an agent enhances activity of PPAR-γ is a determination that the agent will have activity in reducing loss of neurogenesis.

5. The method of claim 4, wherein the model of neuroinflammation is an animal model, selected from a rodent challenged with LPS; and a rodent subjected to cranial irradiation.

6. The method of claim 5, wherein said measuring is performed with central nervous system tissue.

* * * * *